US012807606B2

(12) United States Patent
Orsi et al.

(10) Patent No.: US 12,807,606 B2
(45) Date of Patent: Nov. 24, 2026

(54) SUBSTITUTED HETEROCYCLIC CSNK1 INHIBITORS

(71) Applicants: The Broad Institute, Inc., Cambridge, MA (US); Bayer Aktiengesellschaft, Leverkusen (DE); Dana-Farber Cancer Institute, Inc., Boston, MA (US)

(72) Inventors: Douglas Orsi, Watertown, MA (US); Florence F. Wagner, Cambridge, MA (US); Steven Corsello, Boston, MA (US); Mrinal Shekhar, Quincy, MA (US); Katarzyna Handing, Framingham, MA (US); Steven James Ferrara, Winchester, MA (US); David McKinney, Cambridge, MA (US); Volker Schulze, Hohen Neuendorf (DE); Anne Mengel, Berlin (DE); Adelaide Clara Faria Alvares De Lemos, Berlin (DE); Sven Christian, East Boston, MA (US); Ulf Bömer, Glienicke (DE); Roman Hillig, Berlin (DE); Christian Lechner, Berlin (DE); Jérémie Xavier Mortier, Berlin (DE); Stefan Kaulfuss, Berlin (DE); Rajesha Rupaimoole, N Billerica, MA (US); Philip Lienau, Berlin (DE); Krzysztof Brzezinka, Berlin (DE); Markus Berger, Berlin (DE)

(73) Assignees: The Broad Institute, Inc., Cambridge, MA (US); Bayer Aktiengesellschaft, Leverkusen (DE); Dana-Farber Cancer Institute, Inc., Boston, MA (US)

( * ) Notice: Subject to any disclaimer, the term of this patent is extended or adjusted under 35 U.S.C. 154(b) by 113 days.

(21) Appl. No.: 18/833,767

(22) PCT Filed: Jan. 27, 2023

(86) PCT No.: PCT/US2023/011694
§ 371 (c)(1),
(2) Date: Jul. 26, 2024

(87) PCT Pub. No.: WO2023/147015
PCT Pub. Date: Aug. 3, 2023

(65) Prior Publication Data

US 2025/0188075 A1 Jun. 12, 2025

Related U.S. Application Data

(60) Provisional application No. 63/303,637, filed on Jan. 27, 2022.

(51) Int. Cl.

| | |
|---|---|
| ***C07D 471/04*** | (2006.01) |
| ***A61K 31/444*** | (2006.01) |
| ***A61K 31/498*** | (2006.01) |
| ***A61K 31/519*** | (2006.01) |

(Continued)

(52) U.S. Cl.
CPC .......... *C07D 471/04* (2013.01); *A61K 31/444* (2013.01); *A61K 31/498* (2013.01); *A61K 31/519* (2013.01); *C07D 487/04* (2013.01); *C07D 519/00* (2013.01)

(58) Field of Classification Search
CPC .. C07D 471/04; C07D 487/04; C07D 519/00; A61K 31/444; A61K 31/498; A61K 31/519
See application file for complete search history.

(56) References Cited

U.S. PATENT DOCUMENTS 8,084,395 B2 12/2011 Selles et al.
8,546,413 B2 10/2013 Marchionni et al.
12,227,501 B2 2/2025 Schulze et al.

(Continued)

FOREIGN PATENT DOCUMENTS

WO WO-99/20624 A1 4/1999
WO WO-2005/013986 A1 2/2005

(Continued)

OTHER PUBLICATIONS

Bibian, Mathieu, et al. Development of highly selective casein kinase 1delta/1epsilon (CK1delta/epsilon) inhibitors with potent antiproliferative properties. Bioorganic & medicinal chemistry letters, 2013, 23.15: 4374-4380.

(Continued)

*Primary Examiner* — Brandon J Fetterolf
(74) *Attorney, Agent, or Firm* — Foley Hoag LLP; David P. Halstead; David S. Surry

(57) ABSTRACT

The invention relates to a compound represented by formula (I) or a pharmaceutically acceptable salt thereof, and associated methods of treating cancer.

(I)

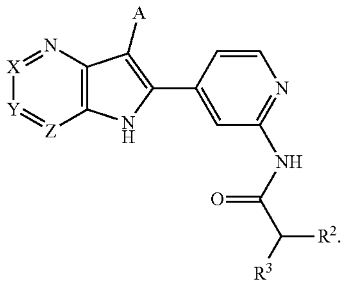

22 Claims, No Drawings

(51) Int. Cl.

| | |
|---|---|
| ***C07D 487/04*** | (2006.01) |
| ***C07D 519/00*** | (2006.01) |

(56) References Cited

U.S. PATENT DOCUMENTS

| | | | | |
|---|---|---|---|---|
| 12,565,496 | B2 | | 3/2026 | Schulze et al. |
| 2004/0209897 | A1 | | 10/2004 | Vernier et al. |
| 2016/0176871 | A1 | * | 6/2016 | Fink et al. |
| 2023/0046077 | A1 | | 2/2023 | Schulze et al. |
| 2023/0322767 | A1 | | 10/2023 | Schulze et al. |
| 2023/0339939 | A1 | | 10/2023 | Schulze et al. |
| 2023/0365554 | A1 | | 11/2023 | Schulze et al. |
| 2023/0391769 | A1 | | 12/2023 | Schulze et al. |

FOREIGN PATENT DOCUMENTS

| | | | | |
|---|---|---|---|---|
| WO | WO-2007/067506 | A2 | | 6/2007 |
| WO | WO2008132434 | A2 | * | 11/2008 |
| WO | WO-2010/046215 | A2 | | 4/2010 |
| WO | WO-2010/070237 | A1 | | 6/2010 |
| WO | WO-2010/070238 | A1 | | 6/2010 |
| WO | WO-2011/053476 | A1 | | 5/2011 |
| WO | WO-2015/073763 | A1 | | 5/2015 |
| WO | WO-2015/195880 | A1 | | 12/2015 |
| WO | WO-2016/100166 | A1 | | 6/2016 |
| WO | WO-2016/120196 | A1 | | 8/2016 |
| WO | WO-2017/079558 | A1 | | 5/2017 |
| WO | WO-2020/161257 | A1 | | 8/2020 |
| WO | WO-2022/023337 | A1 | | 2/2022 |
| WO | WO-2022/023339 | A1 | | 2/2022 |
| WO | WO-2022/023340 | A1 | | 2/2022 |
| WO | WO-2022/023341 | A1 | | 2/2022 |
| WO | WO-2023/147015 | A1 | | 8/2023 |

OTHER PUBLICATIONS

Golub et al., "Molecular classification of cancer: class discovery and class prediction by gene expression monitoring." Science 286 (1999): 531-537.

Huart, Anne-Sophie, et al. A Casein kinase 1/Checkpoint kinase 1 pyrazolo-pyridine protein kinase inhibitor as novel activator of the p53 pathway. Bioorganic & medicinal chemistry letters, 2013, 23.20: 5578-5585.

International Search Report and Written Opinion for Application No. PCT/US2023/011694 dated Apr. 27, 2023.

International Search Report and Written Opinion for International Application No. PCT/EP2021/070992 dated Nov. 3, 2021.

International Search Report and Written Opinion for International Application No. PCT/EP2021/070994 dated Oct. 27, 2021.

International Search Report and Written Opinion for International Application No. PCT/EP2021/070996 dated Nov. 19, 2021.

International Search Report and Written Opinion for International Application No. PCT/EP2021/070998 dated Oct. 20, 2021.

International Search Report for International Application No. PCT/EP2020/053020 dated May 6, 2020.

Jaras, Marcus, et al. Csnk1a1 inhibition has p53-dependent therapeutic efficacy in acute myeloid leukemia. Journal of Experimental Medicine, 2014, 211.4: 605-612. DOI: <10.1084/jem.20131033>. Published: Mar. 10, 2014.

Knippschild, Uwe, et al. The CK1 family: contribution to cellular stress response and its role in carcinogenesis. Frontiers in oncology, 2014, 4: 96. Published: May 19, 2014.

Lala et al., "Role of nitric oxide in tumor progression: lessons from experimental tumors." Cancer and Metastasis Reviews 17 (1998): 91-106.

Medlineplus, "Cancer" (2007): 10 pages.

Shanware, Naval P., et al. Non-specific in vivo inhibition of CK1 by the pyridinyl imidazole p38 inhibitors SB 203580 and SB 202190. BMB reports, 2009, 42.3: 142. doi: 10.5483/bmbrep.2009.42.3.142. Published: Mar. 31, 2009.

Meanwell, "Fluorine and fluorinated motifs in the design and application of bioisosteres for drug design." Journal of Medicinal Chemistry 61 (2018): 5822-5880.

Supplementary European Search Report for EP Application No. 23747628.8 dated Jan. 2, 2026.

* cited by examiner

SUBSTITUTED HETEROCYCLIC CSNK1 INHIBITORS

RELATED APPLICATIONS

This application is a US § 371 National Stage of International Application No. PCT/US23/11694, filed Jan. 27, 2023, which claims the benefit of U.S. Provisional Application No. 63/303,637, filed Jan. 27, 2022, the content of each of which is hereby incorporated by reference in its entirety.

BACKGROUND OF THE INVENTION

One of the most fundamental characteristics of cancer cells is their ability to sustain chronic proliferation whereas in normal tissues the entry into and progression through the cell division cycle is tightly controlled to ensure a homeostasis of cell number and maintenance of normal tissue function. Loss of proliferation control was emphasized as one of the six hallmarks of cancer (Hanahan D and Weinberg R A, Cell 100, 57, 2000; Hanahan D and Weinberg R A, Cell 144, 646, 2011).

The members of the casein kinase 1 (CSNK1) family are highly conserved and are expressed in many eukaryotes ranging from yeast to humans. Mammalian CSNK1 isoforms (α, β, γ, δ, ε) and their splice variants are involved in diverse cellular processes including membrane trafficking, circadian rhythm, cell cycle progression, chromosome segregation, apoptosis and cellular differentiation. Mutations and deregulation of CSNK1 expression and activity have been linked to proliferative diseases such as cancer (Knippschild, Onkologie 2005, 28, 508-514).

CSNK1 substrates are enzymes, transcription factors, splice factors, cytoskeleton proteins, receptors, membrane-associated proteins and cell signaling proteins. Since recognition motifs for CSNK1 are found on most cellular proteins, more than 140 in vitro and in vivo substrates have been reported thus far (Knippschild et al., Front Oncol. 2014 May 19; 4:96). Several known substrates especially of the CSNK1α and δ isoforms, are involved in oncogenic signaling pathways as Wnt/β-catenin (β-catenin; disheveled (DVL); adenomatous polyposis coli (APC); nuclear factor of activated Tcells, cytoplasmic 3 (NFATC3)), p53 (p53; p53/E3 ubiquitin-protein ligase Mdm2 (MDM2)), PI3K/AKT (forkhead box protein O1 (Foxo1)), death receptor signaling (Fas-associated death domain protein (FADD); and BH3-interactive domain death agonist (BID)) (Schittek and Sinnberg Molecular Cancer 2014, 13:231). A distinctive feature of CSNK1 family members is their exclusive need of ATP to phosphorylate their substrates and their independency of other co-factors.

CSNK1α plays a role in the mitotic spindle formation during cell division and in DNA repair mechanisms, and participates in RNA metabolism. Antibodies specific for CSNK1α block cell cycle progression during M phase in mouse oocytes, which indicates that CSNK1α is required for proper cell cycle progression in these cells. CSNK1α can be found at the centrosomes, microtubule asters and the kinetochore. Similarly, CSNK1α regulates apoptotic signaling pathways, however, there seems to be cell type-specific differences. CSNK1α has been shown to have an anti-apoptotic function in the extrinsic apoptosis pathway. Its inhibition increased Fas-induced apoptosis in Hela cells, whereas the overexpression of CSNK1α delayed cell death, caused by the phosphorylation of BID, prevented the caspase 8 dependent cleavage of BID. In addition, CSNK1α inhibits TRAIL induced apoptosis by modification of the TNF receptor or FADD at the death-inducing signaling complex (DISC). Therefore, downregulation of CSNK1α leads to an enhancement of TRAIL-induced cell death. Likewise, CSNK1α promotes cell survival by interacting with the retinoid X receptor (RXR). Downregulation of CSNK1α enhances the apoptotic effect of RXR agonists (Schittek and Sinnberg, Molecular Cancer 2014, 13, 231).

Knockdown or downregulation of CSNK1α in the intestinal epithelium of mice, in human colon cancers or in leukemia cells triggers p53 activation. Similarly, one study showed that CSNK1α stably associates with MDM2, stimulates MDM2-p53 binding, and cooperates with MDM2 to inactivate p53. These data suggest that inhibition of CSNK1α activity increases p53 activity. The knockdown of CSNK1α induces p53 transcriptional activity by reducing the inhibitory effect of MDM2 for p53 since MDM2 phosphorylation is necessary for interaction with p53 (Schittek and Sinnberg, Molecular Cancer 2014, 13, 231).

Ribosomal protein S6 (RPS6) is a critical component of the 40S ribosomal subunit that mediates translation initiation. RPS6 activity is regulated by phosphorylation by CSNK1a, which phosphorylates serine residue 247, enhancing the phosphorylation of upstream sites (Hutchinson et al., JBC, 2011, 286, 10, 8688). CSNK1α inhibition leads to dramatic reduction in RPS6 phosphorylation and activation of p53, resulting in selective elimination of solid tumor and AML cells. Pharmacological inhibition of CSNK1α in p53 wt colon and lung carcinoma as well as in AML induces p53 accumulation along with apoptosis. Targeting of CSNK1α provides a potential approach to the therapeutic activation of p53 in AML, a disorder predominantly associated with non-mutated p53 (Jaras et al., J. Exp. Med. 2014, 211, 4, 605).

CSNK1α is an essential participant in the aberrant NF-kB activity required for ABC DLBCL subtype survival. CSNK1α knockdown is specifically lethal to ABC DLBCL cells (Bidere, Nature, 458, 5 Mar. 2009). Pharmacological inhibition of CSNK1α will specifically kill ABC-DLBCL due to the blocking of the CARD11-Bcl-10-MALT1 complex (CBM complex).

Thus, pharmacological inhibition of CSNK1α represents a new approach for the treatment of proliferative disorders, including solid tumors such as carcinomas, sarcomas, leukaemias and lymphoid malignancies or other disorders, associated with uncontrolled cellular proliferation.

Due to the fact that especially cancer disease, being expressed by uncontrolled proliferative cellular processes in tissues of different organs of the human- or animal body is still not considered to be a controlled disease in that sufficient drug therapies do not already exist, there is a strong need to provide further new therapeutically useful drugs, preferably those inhibiting new targets and providing new therapeutic options.

Therefore, inhibitors of Casein kinase 1 alpha and/or delta represent valuable compounds as single agent therapies that in some instances, can complement other therapeutic options either as single agents or in combination with other drugs.

SUMMARY OF THE INVENTION

The invention provides compounds represented by formula (I) or a pharmaceutically acceptable salt thereof:

(I)

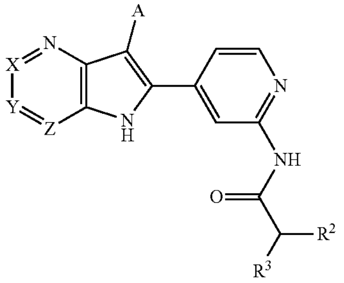

wherein,

A is aryl or heteroaryl;

X, Y, and Z are each independently N or $CR^1$, wherein at most of one of X, Y and Z is N;

each $R^1$ is independently H, alkyl, alkoxy, haloalkoxy, halo, nitrile, amino, or aminoalkyl;

$R^2$ is haloalkyl, aryl or hydrogen; and $R^3$ is optionally substituted heteroaryl.

Another aspect of the invention provides a method of treating a hyperproliferative disease or disorder responsive to induction of cell death comprising administering a compound or pharmaceutical composition of the present invention.

The compounds represented by formula (I) inhibit Casein kinase 1 alpha and/or Casein kinase 1 delta and/or Casein kinase 1 gamma.

The compounds of the present invention have surprising and advantageous properties. In particular, compounds of the present invention have surprisingly been found to effectively inhibit Casein kinase 1 alpha and/or Casein kinase 1 delta and/or Casein kinase 1 gamma, and exhibit improved solubility.

In certain embodiments, compounds of the present invention display an $IC_{50}$ below 100 nM in a CSNK1A1 kinase assay in the presence of 1 μM ATP.

In certain embodiments, compounds of the present invention display an $IC_{50}$ below 125 nM in a CSNK1A1 kinase assay in the presence of 1 mM ATP.

DESCRIPTION OF THE INVENTION

Compounds

The invention provides compounds represented by formula (I) or a pharmaceutically acceptable salt thereof:

(I)

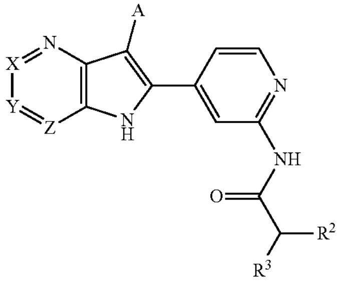

wherein,

A is aryl or heteroaryl;

X, Y and Z are each independently N or $CR^1$, wherein at most of one of X, Y and Z is N;

each $R^1$ is independently H, alkyl, alkoxy, haloalkoxy, halo, nitrile, amino, or aminoalkyl;

$R^2$ is haloalkyl, aryl or hydrogen; and $R^3$ is optionally substituted heteroaryl.

In certain embodiments, X, Y and Z are each $CR^1$.

In certain embodiments, each $R^1$ is H.

In certain embodiments, A is heteroaryl. In other embodiments, A is 5-membered heteroaryl. In other embodiments, A is 6-membered heteroaryl.

In certain embodiments, A is pyridyl.

In certain embodiments, A is

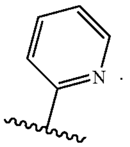 [SMILES: *c1ccccn1]

In certain embodiments, the compound is represented by formula (IA):

(IA)

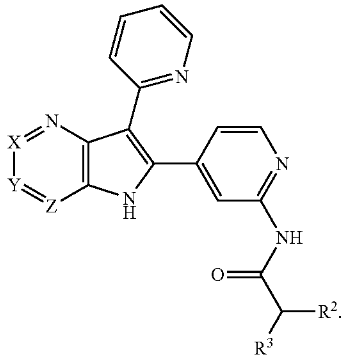

In certain embodiments, the compound is represented by formula (II):

(II)

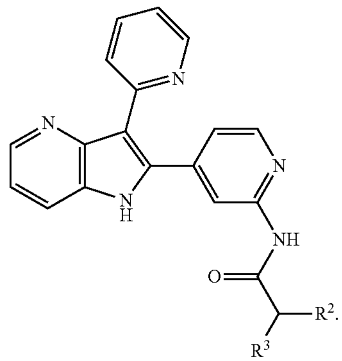

In certain embodiments, $R^2$ is haloalkyl. In other embodiments, $R^2$ is $C_1$-$C_3$ fluoroalkyl. In other embodiments, $R^2$ is 2,2-difluoroethyl. In other embodiments, $R^2$ is hydrogen. In other embodiments, $R^2$ is fluorophenyl. In other embodiments, $R^2$ is 4-fluorophenyl. In certain embodiments, $R^3$ is a 5-membered heteroaryl. In other embodiments, $R^3$ is a 6-membered heteroaryl. In other embodiments, $R^3$ is a fused [5.6] heteroaryl. In other embodiments, $R^3$ is a fused [6.6] heteroaryl.

In certain embodiments, $R^3$ comprises at least one N.

In certain embodiments, $R^3$ comprises at least two heteroatoms.

In certain embodiments, $R^3$ is a substituted heteroaryl.

In certain embodiments, $R^3$ is substituted with one or more groups independently selected from alkyl, haloalkyl, hydroxy, alkoxy, haloalkoxy, halo, amino, and aminoalkyl.

In certain embodiments, $R^3$ is substituted with one or more groups independently selected from $C_{1-4}$ alkyl, cycloalkyl and $C_{1-2}$ haloalkyl.

In certain embodiments, $R^3$ is substituted with one or more groups independently selected from methyl, isopropyl, cyclopropyl, trifluoromethyl and 2,2-difluoroethyl.

In certain embodiments, the compound is selected from:

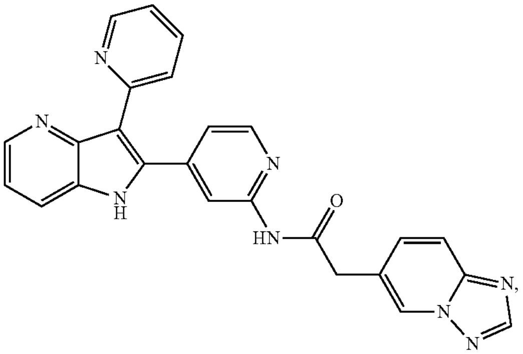

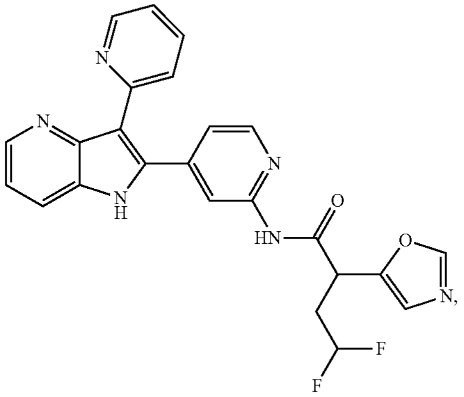

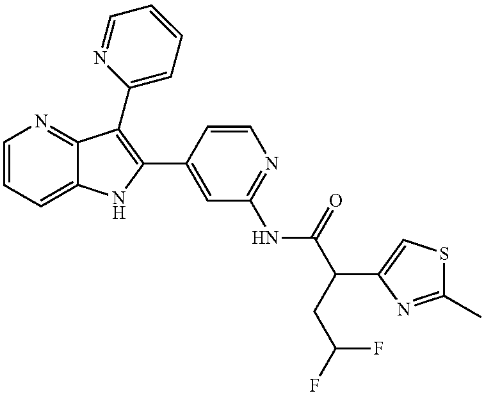

,

-continued

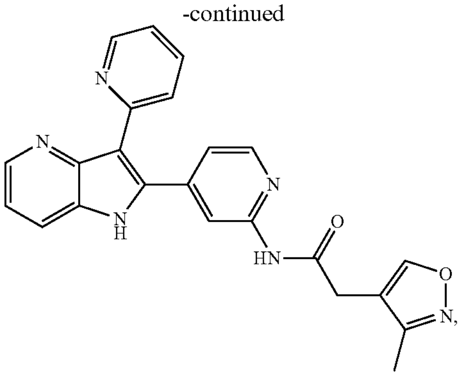

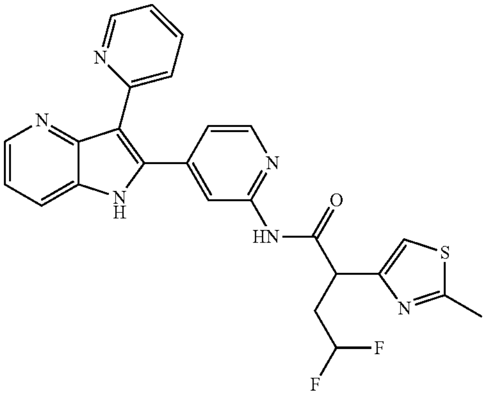

,

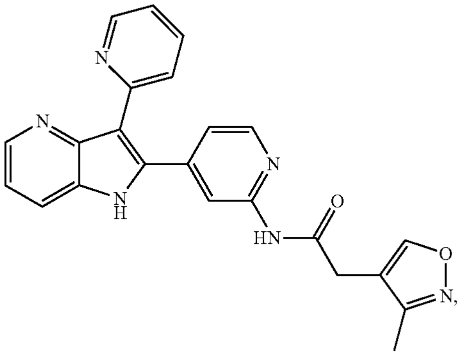

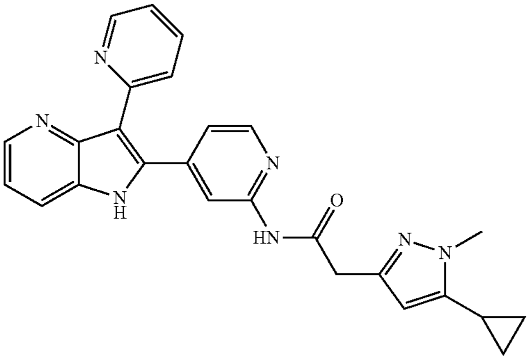

,

-continued
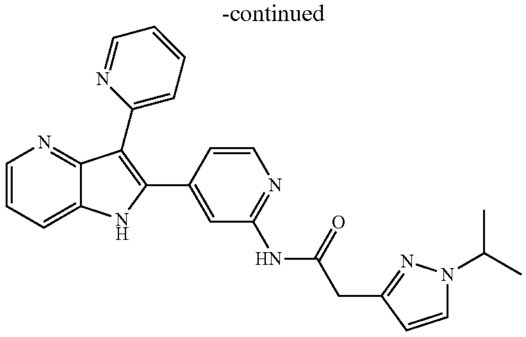
,
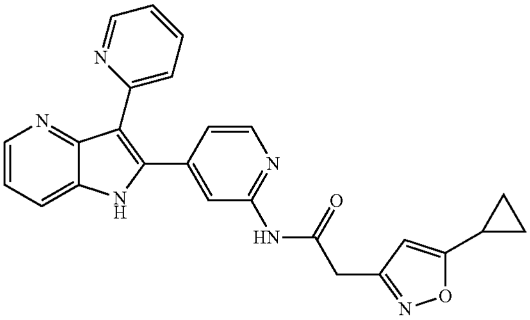
,
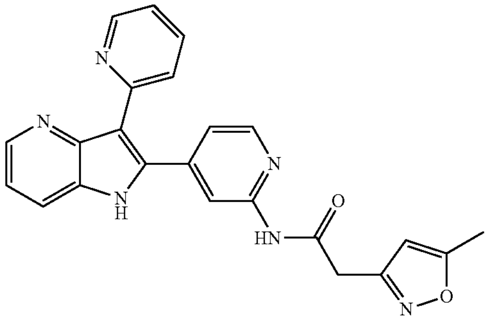
,
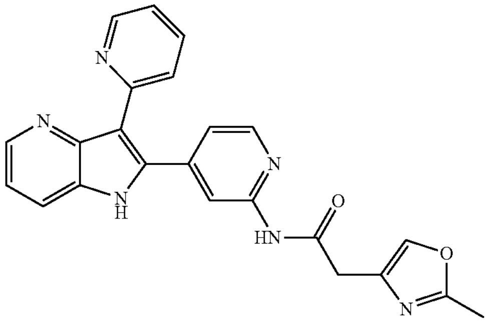
,
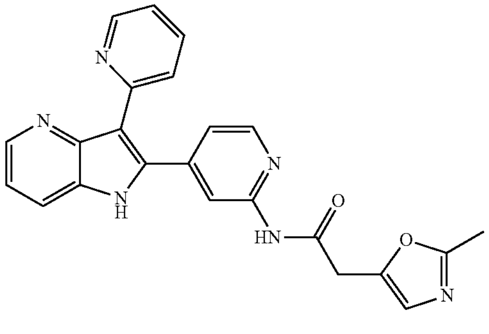
,
-continued
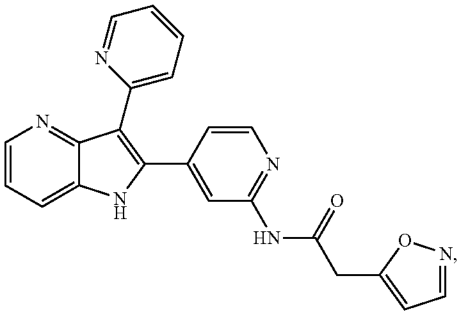
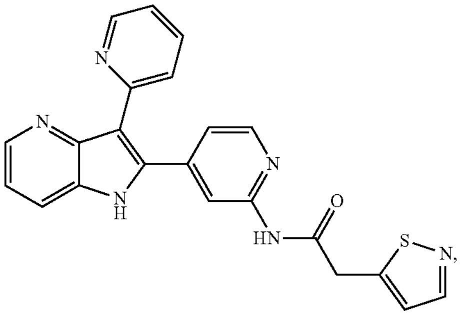
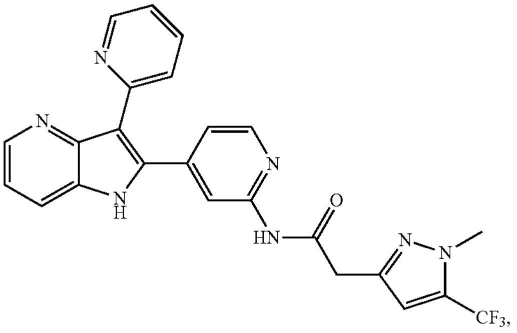
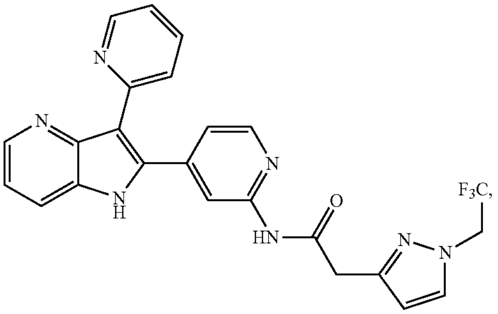
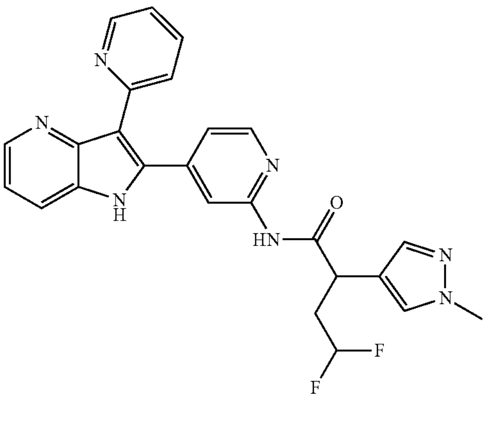
, -continued
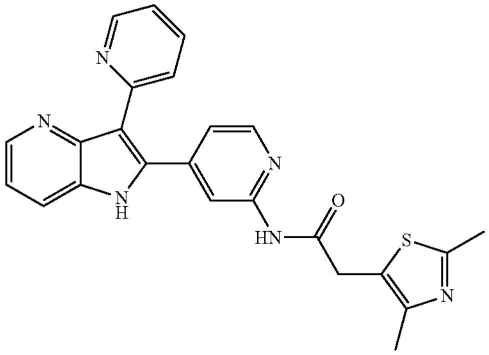
,
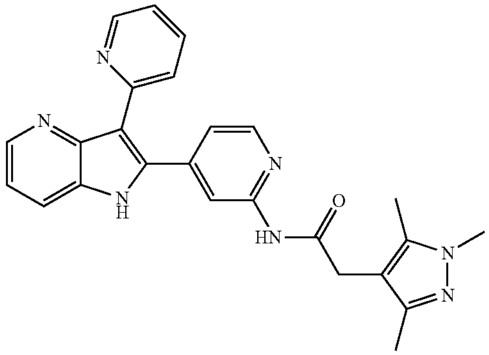
,
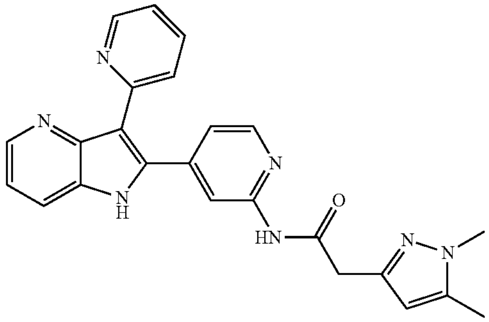
,
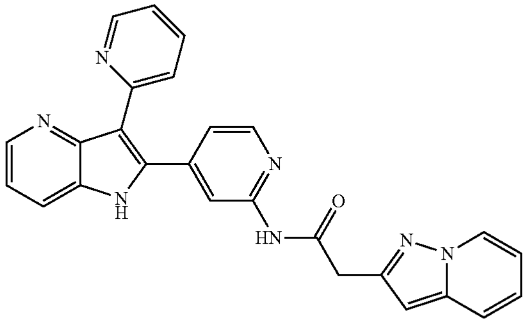
,
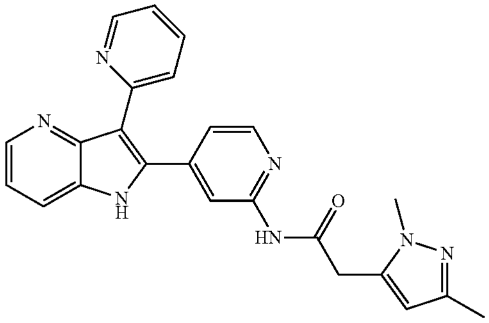
,
-continued
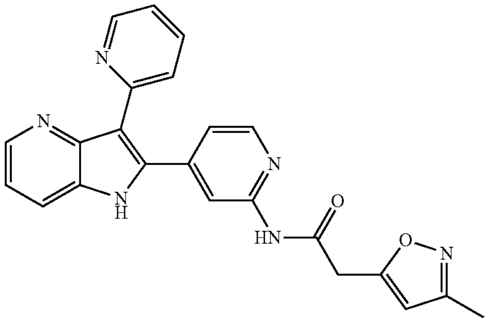
,
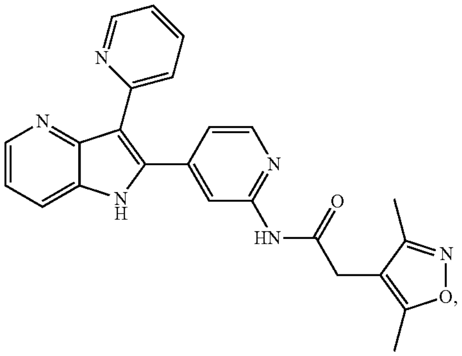
,
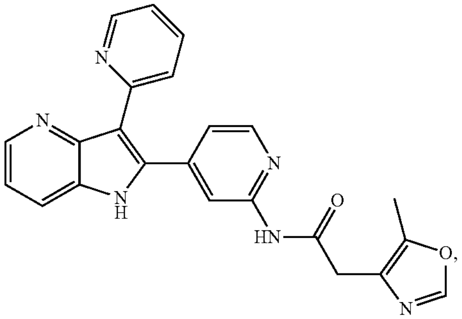
,
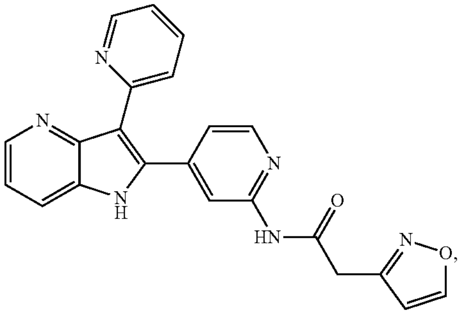
,
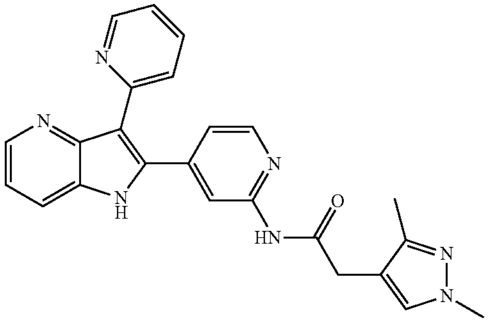
, -continued
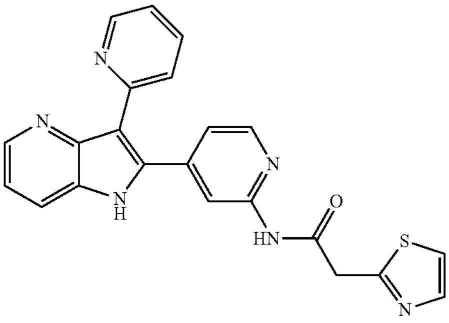
,
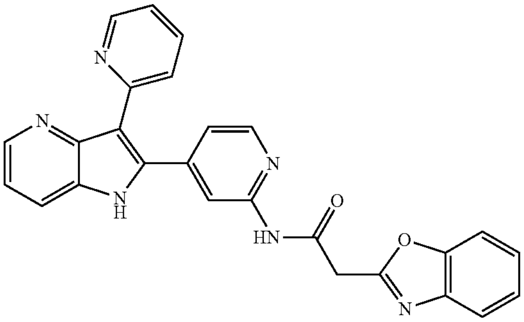
,
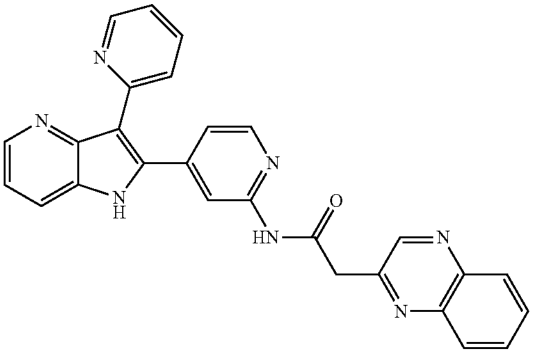
,
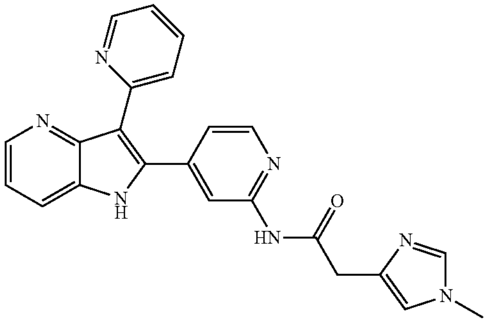
,
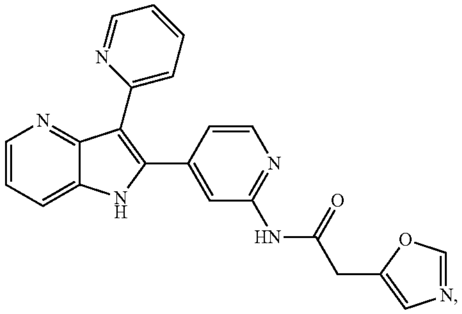
,
-continued
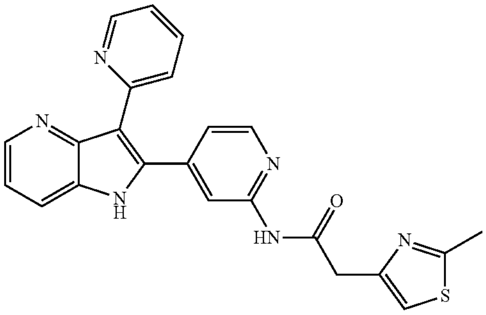
,
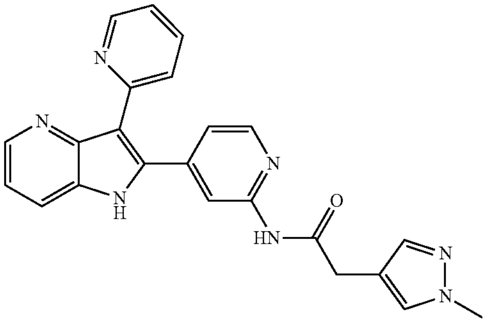
,
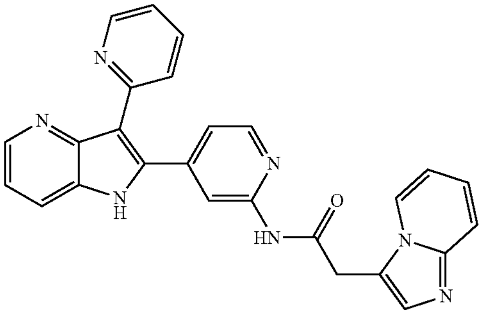
,
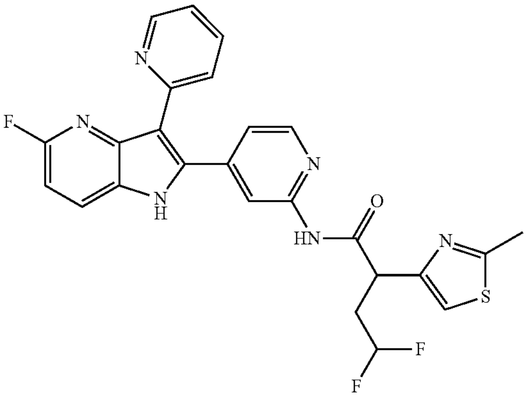
, -continued
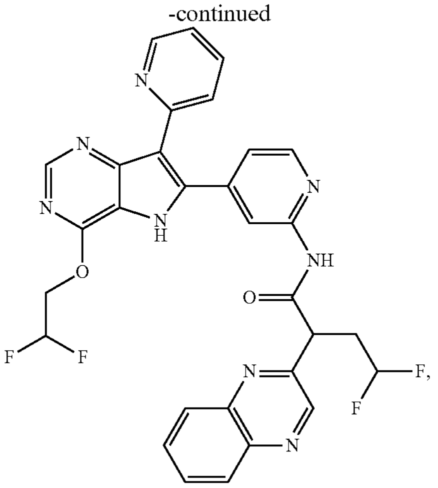
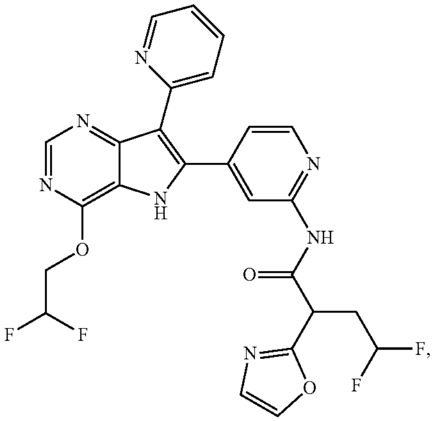
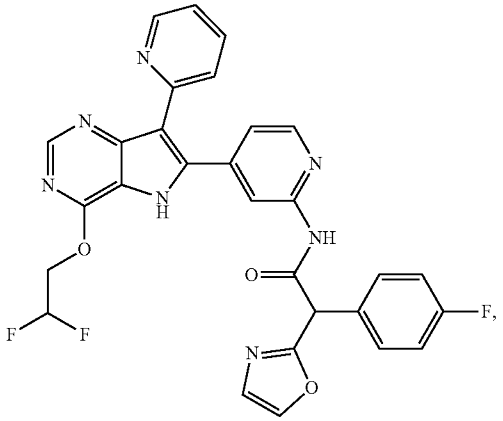
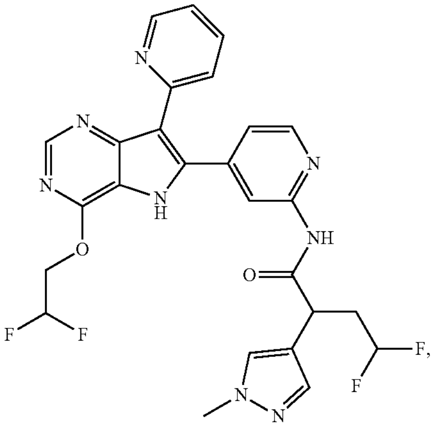
-continued
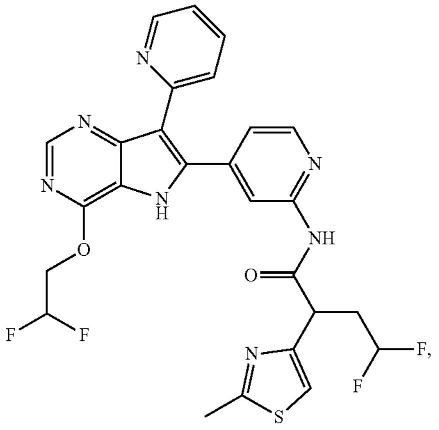
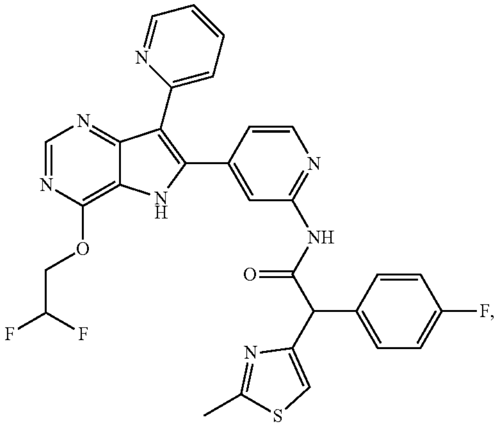
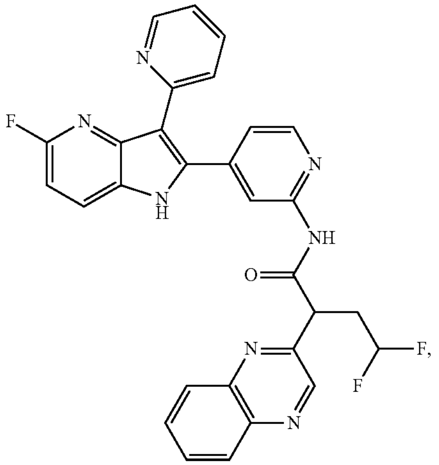

-continued

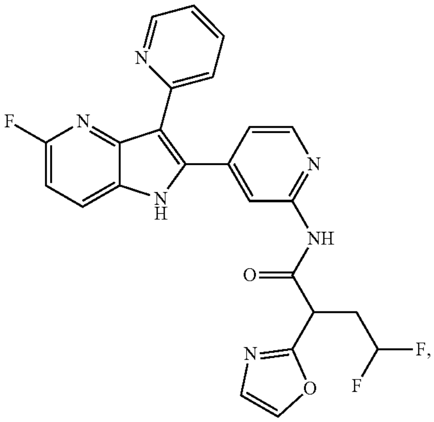

,

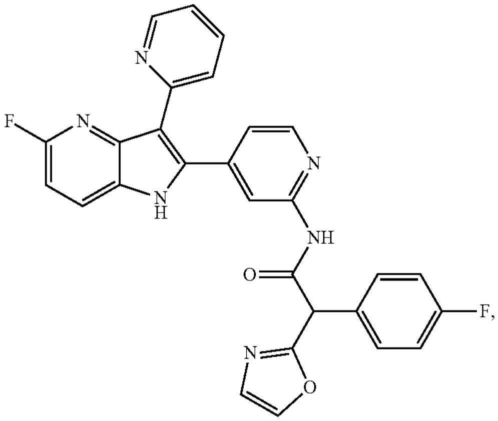

,

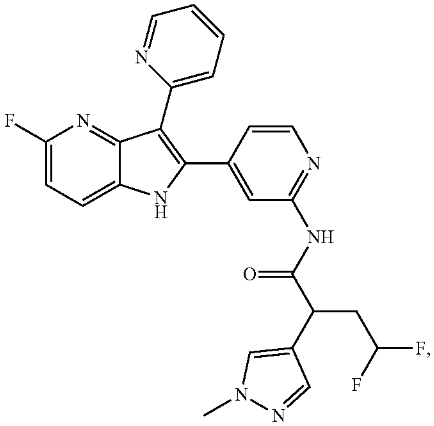

,

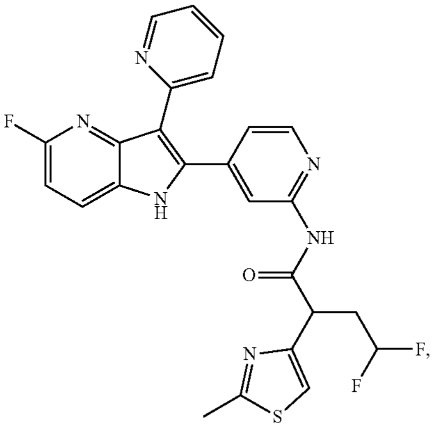

, and

-continued

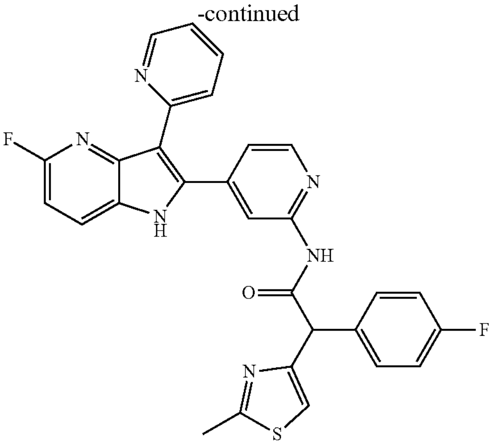

or a pharmaceutically acceptable salt thereof.

Methods of Treatment

The present invention provides a method of treating a hyperproliferative disease or disorder responsive to induction of cell death comprising administering a compound or pharmaceutical composition of the present invention.

In certain embodiments, the hyperproliferative disease or disorder responsive to induction of cell death is a haematological tumor, solid tumor, or metastases thereof.

In certain embodiments, the haematological tumor is a lymphoma or metastases thereof.

In certain embodiments, the lymphoma is diffuse large B-cell lymphoma or metastases thereof.

In certain embodiments, the solid tumor is a cervical tumor, a lung tumor, a colon tumor, or metastases thereof.

In certain embodiments, the lung tumor is a lung carcinoma or metastases thereof.

In certain embodiments, the colon tumor is a colorectal carcinoma or metastases thereof.

In certain embodiments, the solid tumor is a head and neck squamous cell carcinoma or metastases thereof.

In certain embodiments, the solid tumor is a gastric tumor or metastases thereof.

In certain embodiments, the solid tumor is a esophageal tumor or metastases thereof.

In certain embodiments, the solid tumor is a bladder tumor or metastases thereof.

In certain embodiments, wherein the solid tumor is a urinary tract tumor or metastases thereof.

Hyper-Proliferative Disorders

The present invention relates to a method for using the compounds of the present invention and compositions thereof, to treat mammalian hyper-proliferative disorders. Compounds can be utilized to inhibit, block, reduce, decrease, etc., cell proliferation and/or cell division, and/or produce cell death e.g. apoptosis. This method comprises administering to a mammal in need thereof, including a human, an amount of a compound of this invention, or a pharmaceutically acceptable salt, isomer, polymorph, metabolite, hydrate, solvate or ester thereof; etc. which is effective to treat the disorder.

Hyper-proliferative disorders include but are not limited, e.g., psoriasis, keloids, and other hyperplasias affecting the skin, benign prostate hyperplasia (BPH), solid tumours, such as cancers of the breast, respiratory tract, brain, reproductive organs, digestive tract, urinary tract, eye, liver, skin, head and neck, thyroid, parathyroid and their distant metastases. Those disorders also include lymphomas, sarcomas, and leukaemias.

Examples of breast cancer include, but are not limited to invasive ductal carcinoma, invasive lobular carcinoma, ductal carcinoma in situ, and lobular carcinoma in situ.

Examples of cancers of the respiratory tract include, but are not limited to small-cell and non-small-cell lung carcinoma, as well as bronchial adenoma and pleuropulmonary blastoma.

Examples of brain cancers include, but are not limited to brain stem and hypothalamic glioma, cerebellar and cerebral astrocytoma, medulloblastoma, ependymoma, as well as neuroectodermal and pineal tumour.

Tumours of the male reproductive organs include, but are not limited to prostate and testicular cancer. Tumours of the female reproductive organs include, but are not limited to endometrial, cervical, ovarian, vaginal, and vulvar cancer, as well as sarcoma of the uterus.

Tumours of the digestive tract include, but are not limited to anal, colon, colorectal, oesophageal, gallbladder, gastric, pancreatic, rectal, small-intestine, and salivary gland cancers.

Tumours of the urinary tract include, but are not limited to bladder, penile, kidney, renal pelvis, ureter, urethral and human papillary renal cancers.

Eye cancers include, but are not limited to intraocular melanoma and retinoblastoma.

Examples of liver cancers include, but are not limited to hepatocellular carcinoma (liver cell carcinomas with or without fibrolamellar variant), cholangiocarcinoma (intrahepatic bile duct carcinoma), and mixed hepatocellular cholangiocarcinoma.

Skin cancers include, but are not limited to squamous cell carcinoma, Kaposi's sarcoma, malignant melanoma, Merkel cell skin cancer, and non-melanoma skin cancer.

Head-and-neck cancers include, but are not limited to laryngeal, hypopharyngeal, nasopharyngeal, oropharyngeal cancer, lip and oral cavity cancer and squamous cell. Lymphomas include, but are not limited to AIDS-related lymphoma, non-Hodgkin's lymphoma, cutaneous T-cell lymphoma, Burkitt lymphoma, Hodgkin's disease, and lymphoma of the central nervous system.

Sarcomas include, but are not limited to sarcoma of the soft tissue, osteosarcoma, malignant fibrous histiocytoma, lymphosarcoma, and rhabdomyosarcoma.

Leukemias include, but are not limited to acute myeloid leukemia, acute lymphoblastic leukemia, chronic lymphocytic leukemia, chronic myelogenous leukemia, and hairy cell leukemia.

These disorders have been well characterized in humans, but also exist with a similar etiology in other mammals, and can be treated by administering pharmaceutical compositions of the present invention.

Kinase Disorders

The present invention also provides methods for the treatment of disorders associated with aberrant mitogen extracellular kinase activity, including, but not limited to stroke, heart failure, hepatomegaly, cardiomegaly, diabetes, Alzheimer's disease, cystic fibrosis, symptoms of xenograft rejections, septic shock or asthma.

Effective amounts of compounds of the present invention can be used to treat such disorders, including those diseases (e.g., cancer) mentioned in the Background section above. Nonetheless, such cancers and other diseases can be treated with compounds of the present invention, regardless of the mechanism of action and/or the relationship between the kinase and the disorder.

The phrase "aberrant kinase activity" or "aberrant tyrosine kinase activity," includes any abnormal expression or activity of the gene encoding the kinase or of the polypeptide it encodes. Examples of such aberrant activity, include, but are not limited to, over-expression of the gene or polypeptide; gene amplification; mutations which produce constitutively-active or hyperactive kinase activity; gene mutations, deletions, substitutions, additions, etc.

The present invention also provides for methods of inhibiting a kinase activity, especially of mitogen extracellular kinase, comprising administering an effective amount of a compound of the present invention, including salts, polymorphs, metabolites, hydrates, solvates, prodrugs (e.g.: esters) thereof, and diastereoisomeric forms thereof. Kinase activity can be inhibited in cells (e.g., in vitro), or in the cells of a mammalian subject, especially a human patient in need of treatment.

Angiogenic Disorders

The present invention also provides methods of treating disorders and diseases associated with excessive and/or abnormal angiogenesis.

Inappropriate and ectopic expression of angiogenesis can be deleterious to an organism. A number of pathological conditions are associated with the growth of extraneous blood vessels. These include, e.g., diabetic retinopathy, ischemic retinal-vein occlusion, and retinopathy of prematurity (Aiello et al. New Engl. J. Med. 1994, 331, 1480; Peer et al. Lab. Invest. 1995, 72, 638), age-related macular degeneration (AMD) (Lopez et al. Invest. Opththalmol. Vis. Sci. 1996, 37, 855), neovascular glaucoma, psoriasis, retrolental fibroplasias, angiofibroma, inflammation, rheumatoid arthritis (RA), restenosis, in-stent restenosis, vascular graft restenosis, etc. In addition, the increased blood supply associated with cancerous and neoplastic tissue, encourages growth, leading to rapid tumour enlargement and metastasis. Moreover, the growth of new blood and lymph vessels in a tumour provides an escape route for renegade cells, encouraging metastasis and the consequence spread of the cancer. Thus, compounds of the present invention can be utilized to treat and/or prevent any of the aforementioned angiogenesis disorders, e.g., by inhibiting and/or reducing blood vessel formation; by inhibiting, blocking, reducing, decreasing, etc. endothelial cell proliferation or other types involved in angiogenesis, as well as causing cell death, e.g., apoptosis, of such cell types.

Preferably, the diseases of said method are haematological tumours, solid tumour and/or metastases thereof.

The compounds of the present invention can be used in particular in therapy and prevention, e.g., prophylaxis, especially in therapy of tumour growth and metastases, especially in solid tumours of all indications and stages with or without pre-treatment of the tumour growth.

Pharmaceutical Compositions

The present invention also provides a pharmaceutical composition comprising a compound of the present invention and a pharmaceutically acceptable excipient The compositions and methods of the present invention may be utilized to treat an individual in need thereof. In certain embodiments, the individual is a mammal such as a human, or a non-human mammal. When administered to an animal, such as a human, the composition or the compound is preferably administered as a pharmaceutical composition comprising, for example, a compound of the invention and a pharmaceutically acceptable carrier. Pharmaceutically acceptable carriers are well known in the art and include, for example, aqueous solutions such as water or physiologically buffered saline or other solvents or vehicles such as glycols, glycerol, oils such as olive oil, or injectable organic esters. In preferred embodiments, when such pharmaceutical compositions are for human administration, particularly for invasive routes of administration (i.e., routes, such as injection or implantation, that circumvent transport or diffusion through an epithelial barrier), the aqueous solution is pyrogen-free, or substantially pyrogen-free. The excipients can be chosen, for example, to effect delayed release of an agent or to selectively target one or more cells, tissues or organs. The pharmaceutical composition can be in dosage unit form such as tablet, capsule (including sprinkle capsule and gelatin capsule), granule, lyophile for reconstitution, powder, solution, syrup, suppository, injection or the like. The composition can also be present in a transdermal delivery system, e.g., a skin patch. The composition can also be present in a solution suitable for topical administration, such as a lotion, cream, or ointment.

A pharmaceutically acceptable carrier can contain physiologically acceptable agents that act, for example, to stabilize, increase solubility or to increase the absorption of a compound such as a compound of the invention. Such physiologically acceptable agents include, for example, carbohydrates, such as glucose, sucrose or dextrans, antioxidants, such as ascorbic acid or glutathione, chelating agents, low molecular weight proteins or other stabilizers or excipients. The choice of a pharmaceutically acceptable carrier, including a physiologically acceptable agent, depends, for example, on the route of administration of the composition. The preparation or pharmaceutical composition can be a self-emulsifying drug delivery system or a self-micro-emulsifying drug delivery system. The pharmaceutical composition (preparation) also can be a liposome or other polymer matrix, which can have incorporated therein, for example, a compound of the invention. Liposomes, for example, which comprise phospholipids or other lipids, are nontoxic, physiologically acceptable and metabolizable carriers that are relatively simple to make and administer.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

A pharmaceutical composition (preparation) can be administered to a subject by any of a number of routes of administration including, for example, orally (for example, drenches as in aqueous or non-aqueous solutions or suspensions, tablets, capsules (including sprinkle capsules and gelatin capsules), boluses, powders, granules, pastes for application to the tongue); absorption through the oral mucosa (e.g., sublingually); subcutaneously; transdermally (for example as a patch applied to the skin); and topically (for example, as a cream, ointment or spray applied to the skin). The compound may also be formulated for inhalation. In certain embodiments, a compound may be simply dissolved or suspended in sterile water. Details of appropriate routes of administration and compositions suitable for same can be found in, for example, U.S. Pat. Nos. 6,110,973, 5,763,493, 5,731,000, 5,541,231, 5,427,798, 5,358,970 and 4,172,896, as well as in patents cited therein.

The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient that can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an active compound, such as a compound of the invention, with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules (including sprinkle capsules and gelatin capsules), cachets, pills, tablets, lozenges (using a flavored basis, usually sucrose and acacia or tragacanth), lyophile, powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. Compositions or compounds may also be administered as a bolus, electuary or paste.

To prepare solid dosage forms for oral administration (capsules (including sprinkle capsules and gelatin capsules), tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; (10) complexing agents, such as, modified and unmodified cyclodextrins; and (11) coloring agents. In the case of capsules (including sprinkle capsules and gelatin capsules), tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions, such as dragees, capsules (including sprinkle capsules and gelatin capsules), pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms useful for oral administration include pharmaceutically acceptable emulsions, lyophiles for reconstitution, microemulsions, solutions, suspensions, syrups and elixirs. In addition to the active ingredient, the liquid dosage forms may contain inert diluents commonly used in the art, such as, for example, water or other solvents, cyclodextrins and derivatives thereof, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Dosage forms for the topical or transdermal administration include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

The ointments, pastes, creams and gels may contain, in addition to an active compound, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an active compound, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the active compound in the proper medium. Absorption enhancers can also be used to increase the flux of the compound across the skin. The rate of such flux can be controlled by either providing a rate controlling membrane or dispersing the compound in a polymer matrix or gel.

The phrases “parenteral administration” and “administered parenterally” as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion. Pharmaceutical compositions suitable for parenteral administration comprise one or more active compounds in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle.

Injectable depot forms are made by forming microencapsulated matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissue.

For use in the methods of this invention, active compounds can be given per se or as a pharmaceutical composition containing, for example, 0.1 to 99.5% (more preferably, 0.5 to 90%) of active ingredient in combination with a pharmaceutically acceptable carrier.

Methods of introduction may also be provided by rechargeable or biodegradable devices. Various slow-release polymeric devices have been developed and tested in vivo in recent years for the controlled delivery of drugs, including proteinaceous biopharmaceuticals. A variety of biocompatible polymers (including hydrogels), including both biodegradable and non-degradable polymers, can be used to form an implant for the sustained release of a compound at a particular target site.

Actual dosage levels of the active ingredients in the pharmaceutical compositions may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound or combination of compounds employed, or the ester, salt or amide thereof, the route of administration, the time of administration, the rate of excretion of the particular compound(s) being employed, the duration of the treatment, other drugs, compounds and/or materials used in combination with the particular compound(s) employed, the age, sex, weight, condition, general health and prior medical history of the patient being treated, and like factors well known in the medical arts.

A physician or veterinarian having ordinary skill in the art can readily determine and prescribe the therapeutically effective amount of the pharmaceutical composition required. For example, the physician or veterinarian could start doses of the pharmaceutical composition or compound at levels lower than that required in order to achieve the desired therapeutic effect and gradually increase the dosage until the desired effect is achieved. By "therapeutically effective amount" is meant the concentration of a compound that is sufficient to elicit the desired therapeutic effect. It is generally understood that the effective amount of the compound will vary according to the weight, sex, age, and medical history of the subject. Other factors which influence the effective amount may include, but are not limited to, the severity of the patient's condition, the disorder being treated, the stability of the compound, and, if desired, another type of therapeutic agent being administered with the compound of the invention. A larger total dose can be delivered by multiple administrations of the agent. Methods to determine efficacy and dosage are known to those skilled in the art (Isselbacher et al. (1996) Harrison's Principles of Internal Medicine 13 ed., 1814-1882, herein incorporated by reference).

In general, a suitable daily dose of an active compound used in the compositions and methods of the invention will be that amount of the compound that is the lowest dose effective to produce a therapeutic effect. Such an effective dose will generally depend upon the factors described above.

If desired, the effective daily dose of the active compound may be administered as one, two, three, four, five, six or more sub-doses administered separately at appropriate intervals throughout the day, optionally, in unit dosage forms. In certain embodiments of the present invention, the active compound may be administered two or three times daily. In preferred embodiments, the active compound will be administered once daily.

The patient receiving this treatment is any animal in need, including primates, in particular humans; and other mammals such as equines, cattle, swine, sheep, cats, and dogs; poultry; and pets in general.

In certain embodiments, compounds of the invention may be used alone or conjointly administered with another type of therapeutic agent. For example, the compounds of the invention may be used conjointly with a chemotherapeutic or anti-cancer agent including, but not limited to 131I-chTNT, abarelix, abiraterone, aclarubicin, adalimumab, ado-trastuzumab emtansine, afatinib, aflibercept, aldesleukin, alectinib, alemtuzumab, alendronic acid, alitretinoin, altretamine, amifostine, aminoglutethimide, hexyl aminolevulinate, amrubicin, amsacrine, anastrozole, ancestim, anethole dithiolethione, anetumab ravtansine, angiotensin II, antithrombin III, aprepitant, arcitumomab, arglabin, arsenic trioxide, asparaginase, atezolizumab, axitinib, azacitidine, basiliximab, belotecan, bendamustine, besilesomab, belinostat, bevacizumab, bexarotene, bicalutamide, bisantrene, bleomycin, blinatumomab, bortezomib, buserelin, bosutinib, brentuximab vedotin, busulfan, cabazitaxel, cabozantinib, calcitonine, calcium folinate, calcium levofolinate, capecitabine, capromab, carbamazepine carboplatin, carboquone, carfilzomib, carmofur, carmustine, catumaxomab, celecoxib, celmoleukin, ceritinib, cetuximab, chlorambucil, chlormadinone, chlormethine, cidofovir, cinacalcet, cisplatin, cladribine, clodronic acid, clofarabine, cobimetinib, copanlisib, crisantaspase, crizotinib, cyclophosphamide, cyproterone, cytarabine, dacarbazine, dactinomycin, daratumumab, darbepoetin alfa, dabrafenib, dasatinib, daunorubicin, decitabine, degarelix, denileukin diftitox, denosumab, depreotide, deslorelin, dianhydrogalactitol, dexrazoxane, dibrospidium chloride, dianhydrogalactitol, diclofenac, dinutuximab, docetaxel, dolasetron, doxifluridine, doxorubicin, doxorubicin+estrone, dronabinol, eculizumab, edrecolomab, elliptinium acetate, elotuzumab, eltrombopag, endostatin, enocitabine, enzalutamide, epirubicin, epitiostanol, epoetin alfa, epoetin beta, epoetin zeta, eptaplatin, eribulin, erlotinib, esomeprazole, estradiol, estramustine, ethinylestradiol, etoposide, everolimus, exemestane, fadrozole, fentanyl, filgrastim, fluoxymesterone, floxuridine, fludarabine, fluorouracil, flutamide, folinic acid, formestane, fosaprepitant, fotemustine, fulvestrant, gadobutrol, gadoteridol, gadoteric acid meglumine, gadoversetamide, gadoxetic acid, gallium nitrate, ganirelix, gefitinib, gemcitabine, gemtuzumab, Glucarpidase, glutoxim, GM-CSF, goserelin, granisetron, granulocyte colony stimulating factor, histamine dihydrochloride, histrelin, hydroxycarbamide, I-125 seeds, lansoprazole, ibandronic acid, ibritumomab tiuxetan, ibrutinib, idarubicin, ifosfamide, imatinib, imiquimod, improsulfan, indisetron, incadronic acid, ingenol mebutate, interferon alfa, interferon beta, interferon gamma, iobitridol, iobenguane (123I), iomeprol, ipilimumab, irinotecan, Itraconazole, ixabepilone, ixazomib, lanreotide, lansoprazole, lapatinib, Iasocholine, lenalidomide, lenvatinib, lenograstim, lentinan, letrozole, leuprorelin, levamisole, levonorgestrel, levothyroxine sodium, lisuride, lobaplatin, lomustine, lonidamine, masoprocol, medroxyprogesterone, megestrol, melarsoprol, melphalan, mepitiostane, mercaptopurine, mesna, methadone, methotrexate, methoxsalen, methylaminolevulinate, methylprednisolone, methyltestosterone, metirosine, mifamurtide, miltefosine, miriplatin, mitobronitol, mitoguazone, mitolactol, mitomycin, mitotane, mitoxantrone, mogamulizumab, molgramostim, mopidamol, morphine hydrochloride, morphine sulfate, nabilone, nabiximols, nafarelin, naloxone+pentazocine, naltrexone, nartograstim, necitumumab, nedaplatin, nelarabine, neridronic acid, netupitant/palonosetron, nivolumab, pentetreotide, nilotinib, nilutamide, nimorazole, nimotuzumab, nimustine, nintedanib, nitracrine, nivolumab, obinutuzumab, octreotide, ofatumumab, olaparib, olaratumab, omacetaxine mepesuccinate, omeprazole, ondansetron, oprelvekin, orgotein, orilotimod, osimertinib, oxaliplatin, oxycodone, oxymetholone, ozogamicine, p53 gene therapy, paclitaxel, palbociclib, palifermin, palladium-103 seed, palonosetron, pamidronic acid, panitumumab, panobinostat, pantoprazole, pazopanib, pegaspargase, PEG-epoetin beta (methoxy PEG-epoetin beta), pembrolizumab, pegfilgrastim, peginterferon alfa-2b, pembrolizumab, pemetrexed, pentazocine, pentostatin, peplomycin, Perflubutane, perfosfamide, Pertuzumab, picibanil, pilocarpine, pirarubicin, pixantrone, plerixafor, plicamycin, poliglusam, polyestradiol phosphate, polyvinylpyrrolidone+sodium hyaluronate, polysaccharide-K, pomalidomide, ponatinib, porfimer sodium, pralatrexate, prednimustine, prednisone, procarbazine, procodazole, propranolol, quinagolide, rabeprazole, racotumomab, radium-223 chloride, radotinib, raloxifene, raltitrexed, ramosetron, ramucirumab, ranimustine, rasburicase, razoxane, refametinib, regorafenib, risedronic acid, rhenium-186 etidronate, rituximab, rolapitant, romidepsin, romiplostim, romurtide, rucaparib, samarium (153Sm) lexidronam, sargramostim, satumomab, secretin, siltuximab, sipuleucel-T, sizofiran, sobuzoxane, sodium glycididazole, sonidegib, sorafenib, stanozolol, streptozocin, sunitinib, talaporfin, talimogene laherparepvec, tamibarotene, tamoxifen, tapentadol, tasonermin, teceleukin, technetium (99mTc) nofetumomab merpentan, 99mTc-HYNIC-[Tyr3]-octreotide, tegafur, tegafur+gimeracil+oteracil, temoporfin, temozolomide, temsirolimus, teniposide, testosterone, tetrofosmin, thalidomide, thiotepa, thymalfasin, thyrotropin alfa, tioguanine, tocilizumab, topotecan, toremifene, tositumomab, trabectedin, trametinib, tramadol, trastuzumab, trastuzumab emtansine, treosulfan, tretinoin, trifluridine+tipiracil, trilostane, triptorelin, trametinib, trofosfamide, thrombopoietin, tryptophan, ubenimex, valatinib, valrubicin, vandetanib, vapreotide, vemurafenib, vinblastine, vincristine, vindesine, vinflunine, vinorelbine, vismodegib, vorinostat, vorozole, yttrium-90 glass microspheres, zinostatin, zinostatin stimalamer, zoledronic acid, zorubicin. The present disclosure includes the use of pharmaceutically acceptable salts of compounds of the invention in the compositions and methods of the present invention. In certain embodiments, contemplated salts of the invention include, but are not limited to, alkyl, dialkyl, trialkyl or tetra-alkyl ammonium salts. In certain embodiments, contemplated salts of the invention include, but are not limited to, L-arginine, benenthamine, benzathine, betaine, calcium hydroxide, choline, deanol, diethanolamine, diethylamine, 2-(diethylamino) ethanol, ethanolamine, ethylenediamine, N-methylglucamine, hydrabamine, $^{1}$H-imidazole, lithium, L-lysine, magnesium, 4-(2-hydroxyethyl) morpholine, piperazine, potassium, 1-(2-hydroxyethyl) pyrrolidine, sodium, triethanolamine, tromethamine, and zinc salts. In certain embodiments, contemplated salts of the invention include, but are not limited to, Na, Ca, K, Mg, Zn or other metal salts. In certain embodiments, contemplated salts of the invention include, but are not limited to, 1-hydroxy-2-naphthoic acid, 2,2-dichloroacetic acid, 2-hydroxyethanesulfonic acid, 2-oxoglutaric acid, 4-acetamidobenzoic acid, 4-aminosalicylic acid, acetic acid, adipic acid, 1-ascorbic acid, 1-aspartic acid, benzenesulfonic acid, benzoic acid, (+)-camphoric acid, (+)-camphor-10-sulfonic acid, capric acid (decanoic acid), caproic acid (hexanoic acid), caprylic acid (octanoic acid), carbonic acid, cinnamic acid, citric acid, cyclamic acid, dodecylsulfuric acid, ethane-1,2-disulfonic acid, ethanesulfonic acid, formic acid, fumaric acid, galactaric acid, gentisic acid, d-glucoheptonic acid, d-gluconic acid, d-glucuronic acid, glutamic acid, glutaric acid, glycerophosphoric acid, glycolic acid, hippuric acid, hydrobromic acid, hydrochloric acid, isobutyric acid, lactic acid, lactobionic acid, lauric acid, maleic acid, 1-malic acid, malonic acid, mandelic acid, methanesulfonic acid, naphthalene-1,5-disulfonic acid, naphthalene-2-sulfonic acid, nicotinic acid, nitric acid, oleic acid, oxalic acid, palmitic acid, pamoic acid, phosphoric acid, proprionic acid, 1-pyroglutamic acid, salicylic acid, sebacic acid, stearic acid, succinic acid, sulfuric acid, 1-tartaric acid, thiocyanic acid, p-toluenesulfonic acid, trifluoroacetic acid, and undecylenic acid acid salts.

The pharmaceutically acceptable acid addition salts can also exist as various solvates, such as with water, methanol, ethanol, dimethylformamide, and the like. Mixtures of such solvates can also be prepared. The source of such solvate can be from the solvent of crystallization, inherent in the solvent of preparation or crystallization, or adventitious to such solvent.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water-soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal-chelating agents, such as citric acid, ethylenediamine tetraacetic acid (EDTA), sorbitol, tartaric acid, phosphoric acid, and the like.

Definitions

Unless otherwise defined herein, scientific and technical terms used in this application shall have the meanings that are commonly understood by those of ordinary skill in the art. Generally, nomenclature used in connection with, and techniques of, chemistry, cell and tissue culture, molecular biology, cell and cancer biology, neurobiology, neurochemistry, virology, immunology, microbiology, pharmacology, genetics and protein and nucleic acid chemistry, described herein, are those well-known and commonly used in the art.

The methods and techniques of the present disclosure are generally performed, unless otherwise indicated, according to conventional methods well known in the art and as described in various general and more specific references that are cited and discussed throughout this specification. See, e.g., "Principles of Neural Science", McGraw-Hill Medical, New York, N.Y. (2000); Motulsky, "Intuitive Biostatistics", Oxford University Press, Inc. (1995); Lodish et al., "Molecular Cell Biology, 4th ed.", W. H. Freeman & Co., New York (2000); Griffiths et al., "Introduction to Genetic Analysis, 7th ed.", W. H. Freeman & Co., N.Y. (1999); and Gilbert et al., "Developmental Biology, 6th ed.", Sinauer Associates, Inc., Sunderland, MA (2000).

Chemistry terms used herein, unless otherwise defined herein, are used according to conventional usage in the art, as exemplified by "The McGraw-Hill Dictionary of Chemical Terms", Parker S., Ed., McGraw-Hill, San Francisco, C.A. (1985).

All of the above, and any other publications, patents and published patent applications referred to in this application are specifically incorporated by reference herein. In case of conflict, the present specification, including its specific definitions, will control.

The term "agent" is used herein to denote a chemical compound (such as an organic or inorganic compound, a mixture of chemical compounds), a biological macromolecule (such as a nucleic acid, an antibody, including parts thereof as well as humanized, chimeric and human antibodies and monoclonal antibodies, a protein or portion thereof, e.g., a peptide, a lipid, a carbohydrate), or an extract made from biological materials such as bacteria, plants, fungi, or animal (particularly mammalian) cells or tissues. Agents include, for example, agents whose structure is known, and those whose structure is not known. The ability of such agents to inhibit AR or promote AR degradation may render them suitable as "therapeutic agents" in the methods and compositions of this disclosure.

A "patient," "subject," or "individual" are used interchangeably and refer to either a human or a non-human animal. These terms include mammals, such as humans, primates, livestock animals (including bovines, porcines, etc.), companion animals (e.g., canines, felines, etc.) and rodents (e.g., mice and rats).

"Treating" a condition or patient refers to taking steps to obtain beneficial or desired results, including clinical results. As used herein, and as well understood in the art, "treatment" is an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, and remission (whether partial or total), whether detectable or undetectable. "Treatment" can also mean prolonging survival as compared to expected survival if not receiving treatment.

The term "preventing" is art-recognized, and when used in relation to a condition, such as a local recurrence (e.g., pain), a disease such as cancer, a syndrome complex such as heart failure or any other medical condition, is well understood in the art, and includes administration of a composition which reduces the frequency of, or delays the onset of, symptoms of a medical condition in a subject relative to a subject which does not receive the composition. Thus, prevention of cancer includes, for example, reducing the number of detectable cancerous growths in a population of patients receiving a prophylactic treatment relative to an untreated control population, and/or delaying the appearance of detectable cancerous growths in a treated population versus an untreated control population, e.g., by a statistically and/or clinically significant amount.

"Administering" or "administration of" a substance, a compound or an agent to a subject can be carried out using one of a variety of methods known to those skilled in the art. For example, a compound or an agent can be administered, intravenously, arterially, intradermally, intramuscularly, intraperitoneally, subcutaneously, ocularly, sublingually, orally (by ingestion), intranasally (by inhalation), intraspinally, intracerebrally, and transdermally (by absorption, e.g., through a skin duct). A compound or agent can also appropriately be introduced by rechargeable or biodegradable polymeric devices or other devices, e.g., patches and pumps, or formulations, which provide for the extended, slow or controlled release of the compound or agent. Administering can also be performed, for example, once, a plurality of times, and/or over one or more extended periods.

Appropriate methods of administering a substance, a compound or an agent to a subject will also depend, for example, on the age and/or the physical condition of the subject and the chemical and biological properties of the compound or agent (e.g., solubility, digestibility, bioavailability, stability and toxicity). In some embodiments, a compound or an agent is administered orally, e.g., to a subject by ingestion. In some embodiments, the orally administered compound or agent is in an extended release or slow-release formulation, or administered using a device for such slow or extended release.

As used herein, the phrase "conjoint administration" refers to any form of administration of two or more different therapeutic agents such that the second agent is administered while the previously administered therapeutic agent is still effective in the body (e.g., the two agents are simultaneously effective in the patient, which may include synergistic effects of the two agents). For example, the different therapeutic compounds can be administered either in the same formulation or in separate formulations, either concomitantly or sequentially. Thus, an individual who receives such treatment can benefit from a combined effect of different therapeutic agents.

A "therapeutically effective amount" or a "therapeutically effective dose" of a drug or agent is an amount of a drug or an agent that, when administered to a subject will have the intended therapeutic effect. The full therapeutic effect does not necessarily occur by administration of one dose, and may occur only after administration of a series of doses. Thus, a therapeutically effective amount may be administered in one or more administrations. The precise effective amount needed for a subject will depend upon, for example, the subject's size, health and age, and the nature and extent of the condition being treated, such as cancer or MDS. The skilled worker can readily determine the effective amount for a given situation by routine experimentation.

As used herein, the terms "optional" or "optionally" mean that the subsequently described event or circumstance may occur or may not occur, and that the description includes instances where the event or circumstance occurs as well as instances in which it does not. For example, "optionally substituted alkyl" refers to the alkyl may be substituted as well as where the alkyl is not substituted.

It is understood that substituents and substitution patterns on the compounds of the present invention can be selected by one of ordinary skilled person in the art to result chemically stable compounds which can be readily synthesized by techniques known in the art, as well as those methods set forth below, from readily available starting materials. If a substituent is itself substituted with more than one group, it is understood that these multiple groups may be on the same carbon or on different carbons, so long as a stable structure results.

As used herein, the term “optionally substituted” refers to the replacement of one to six hydrogen radicals in a given structure with the radical of a specified substituent including, but not limited to: hydroxyl, hydroxyalkyl, alkoxy, halogen, alkyl, nitro, silyl, acyl, acyloxy, aryl, cycloalkyl, heterocyclyl, amino, aminoalkyl, cyano, haloalkyl, haloalkoxy, —OCO—$CH_2$—O-alkyl, —OP(O)(O-alkyl)$_2$ or —$CH_2$—OP(O)(O-alkyl)$_2$. Preferably, “optionally substituted” refers to the replacement of one to four hydrogen radicals in a given structure with the substituents mentioned above. More preferably, one to three hydrogen radicals are replaced by the substituents as mentioned above. It is understood that the substituent can be further substituted.

As used herein, the term “alkyl” refers to saturated aliphatic groups, including but not limited to $C_1$-$C_{10}$ straight-chain alkyl groups or $C_1$-$C_{10}$ branched-chain alkyl groups. Preferably, the “alkyl” group refers to $C_1$-$C_6$ straight-chain alkyl groups or $C_1$-$C_6$ branched-chain alkyl groups. Most preferably, the “alkyl” group refers to $C_1$-$C_4$ straight-chain alkyl groups or $C_1$-$C_4$ branched-chain alkyl groups. Examples of “alkyl” include, but are not limited to, methyl, ethyl, 1-propyl, 2-propyl, n-butyl, sec-butyl, tert-butyl, 1-pentyl, 2-pentyl, 3-pentyl, neo-pentyl, 1-hexyl, 2-hexyl, 3-hexyl, 1-heptyl, 2-heptyl, 3-heptyl, 4-heptyl, 1-octyl, 2-octyl, 3-octyl or 4-octyl and the like. The “alkyl” group may be optionally substituted.

The term “acyl” is art-recognized and refers to a group represented by the general formula hydrocarbylC(O)—, preferably alkylC(O)—.

The term “acylamino” is art-recognized and refers to an amino group substituted with an acyl group and may be represented, for example, by the formula hydrocarbylC(O)NH—.

The term “acyloxy” is art-recognized and refers to a group represented by the general formula hydrocarbylC(O)O—, preferably alkylC(O)O—.

The term “alkoxy” refers to an alkyl group having an oxygen attached thereto. Representative alkoxy groups include methoxy, ethoxy, propoxy, tert-butoxy and the like.

The term “alkoxyalkyl” refers to an alkyl group substituted with an alkoxy group and may be represented by the general formula alkyl-O-alkyl.

The term “alkyl” refers to saturated aliphatic groups, including straight-chain alkyl groups, branched-chain alkyl groups, cycloalkyl (alicyclic) groups, alkyl-substituted cycloalkyl groups, and cycloalkyl-substituted alkyl groups. In preferred embodiments, a straight chain or branched chain alkyl has 30 or fewer carbon atoms in its backbone (e.g., $C_{1-30}$ for straight chains, $C_{3-30}$ for branched chains), and more preferably 20 or fewer.

Moreover, the term “alkyl” as used throughout the specification, examples, and claims is intended to include both unsubstituted and substituted alkyl groups, the latter of which refers to alkyl moieties having substituents replacing a hydrogen on one or more carbons of the hydrocarbon backbone, including haloalkyl groups such as trifluoromethyl and 2,2,2-trifluoroethyl, etc.

The term “$C_{x-y}$” or “$C_x$-$C_y$”, when used in conjunction with a chemical moiety, such as, acyl, acyloxy, alkyl, alkenyl, alkynyl, or alkoxy is meant to include groups that contain from x to y carbons in the chain. $C_0$alkyl indicates a hydrogen where the group is in a terminal position, a bond if internal. A $C_{1-6}$alkyl group, for example, contains from one to six carbon atoms in the chain.

The term “alkylamino”, as used herein, refers to an amino group substituted with at least one alkyl group.

The term “alkylthio”, as used herein, refers to a thiol group substituted with an alkyl group and may be represented by the general formula alkylS—.

The term “amide”, as used herein, refers to a group

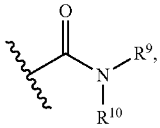

wherein $R^9$ and $R^{10}$ each independently represent a hydrogen or hydrocarbyl group, or $R^9$ and $R^{10}$ taken together with the N atom to which they are attached complete a heterocycle having from 4 to 8 atoms in the ring structure.

The terms “amine” and “amino” are art-recognized and refer to both unsubstituted and substituted amines and salts thereof, e.g., a moiety that can be represented by

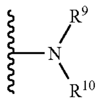 or 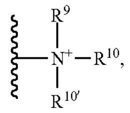

wherein $R^9$, $R^{10}$, and $R^{10'}$ each independently represent a hydrogen or a hydrocarbyl group, or $R^9$ and R 10 taken together with the N atom to which they are attached complete a heterocycle having from 4 to 8 atoms in the ring structure.

The term “aminoalkyl”, as used herein, refers to an alkyl group substituted with an amino group.

The term “aralkyl”, as used herein, refers to an alkyl group substituted with an aryl group.

The term “aryl” as used herein include substituted or unsubstituted single-ring aromatic groups in which each atom of the ring is carbon. Preferably the ring is a 5- to 7-membered ring, more preferably a 6-membered ring. The term “aryl” also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like.

The term “carbamate” is art-recognized and refers to a group

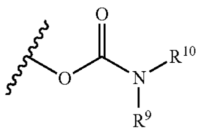 or 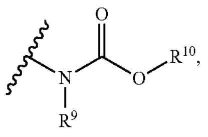

wherein $R^9$ and $R^{10}$ independently represent hydrogen or a hydrocarbyl group.

The term "carbocyclylalkyl", as used herein, refers to an alkyl group substituted with a carbocycle group.

The term "carbocycle" includes 5-7 membered monocyclic and 8-12 membered bicyclic rings. Each ring of a bicyclic carbocycle may be selected from saturated, unsaturated and aromatic rings. Carbocycle includes bicyclic molecules in which one, two or three or more atoms are shared between the two rings. The term "fused carbocycle" refers to a bicyclic carbocycle in which each of the rings shares two adjacent atoms with the other ring. Each ring of a fused carbocycle may be selected from saturated, unsaturated and aromatic rings. In an exemplary embodiment, an aromatic ring, e.g., phenyl, may be fused to a saturated or unsaturated ring, e.g., cyclohexane, cyclopentane, or cyclohexene. Any combination of saturated, unsaturated and aromatic bicyclic rings, as valence permits, is included in the definition of carbocyclic. Exemplary "carbocycles" include cyclopentane, cyclohexane, bicyclo[2.2.1]heptane, 1,5-cyclooctadiene, 1,2,3,4-tetrahydronaphthalene, bicyclo[4.2.0]oct-3-ene, naphthalene and adamantane. Exemplary fused carbocycles include decalin, naphthalene, 1,2,3,4-tetrahydronaphthalene, bicyclo[4.2.0]octane, 4,5,6,7-tetrahydro-1H-indene and bicyclo[4.1.0]hept-3-ene. "Carbocycles" may be substituted at any one or more positions capable of bearing a hydrogen atom.

The term "carbocyclylalkyl", as used herein, refers to an alkyl group substituted with a carbocycle group.

The term "carbonate" is art-recognized and refers to a group $—OCO_2—$.

The term "carboxy", as used herein, refers to a group represented by the formula $—CO_2H$.

The term "ester", as used herein, refers to a group $—C(O)OR^9$ wherein $R^9$ represents a hydrocarbyl group.

The term "ether", as used herein, refers to a hydrocarbyl group linked through an oxygen to another hydrocarbyl group. Accordingly, an ether substituent of a hydrocarbyl group may be hydrocarbyl-O—. Ethers may be either symmetrical or unsymmetrical. Examples of ethers include, but are not limited to, heterocycle-O-heterocycle and aryl-O-heterocycle. Ethers include "alkoxyalkyl" groups, which may be represented by the general formula alkyl-O-alkyl.

The terms "halo" and "halogen" as used herein means halogen and includes chloro, fluoro, bromo, and iodo.

The terms "hetaralkyl" and "heteroaralkyl", as used herein, refers to an alkyl group substituted with a hetaryl group.

The terms "heteroaryl" and "hetaryl" include substituted or unsubstituted aromatic single ring structures, preferably 5- to 7-membered rings, more preferably 5- to 6-membered rings, whose ring structures include at least one heteroatom, preferably one to four heteroatoms, more preferably one or two heteroatoms. The terms "heteroaryl" and "hetaryl" also include polycyclic ring systems having two or more cyclic rings in which two or more atoms are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, pyrazole, pyridine, pyrazine, pyridazine, and pyrimidine, and the like.

The term "heteroatom" as used herein means an atom of any element other than carbon or hydrogen. Preferred heteroatoms are nitrogen, oxygen, and sulfur.

The term "heterocyclylalkyl", as used herein, refers to an alkyl group substituted with a heterocycle group.

The terms "heterocyclyl", "heterocycle", and "heterocyclic" refer to substituted or unsubstituted non-aromatic ring structures, preferably 3- to 10-membered rings, more preferably 3- to 7-membered rings, whose ring structures include at least one heteroatom, preferably one to four heteroatoms, more preferably one or two heteroatoms. The terms "heterocyclyl" and "heterocyclic" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, piperidine, piperazine, pyrrolidine, morpholine, lactones, lactams, and the like.

The term "hydrocarbyl", as used herein, refers to a group that is bonded through a carbon atom that does not have a =O or =S substituent, and typically has at least one carbon-hydrogen bond and a primarily carbon backbone, but may optionally include heteroatoms. Thus, groups like methyl, ethoxyethyl, 2-pyridyl, and even trifluoromethyl are considered to be hydrocarbyl for the purposes of this application, but substituents such as acetyl (which has a =O substituent on the linking carbon) and ethoxy (which is linked through oxygen, not carbon) are not. Hydrocarbyl groups include, but are not limited to aryl, heteroaryl, carbocycle, heterocycle, alkyl, alkenyl, alkynyl, and combinations thereof.

The term "hydroxyalkyl", as used herein, refers to an alkyl group substituted with a hydroxy group.

The term "lower" when used in conjunction with a chemical moiety, such as, acyl, acyloxy, alkyl, alkenyl, alkynyl, or alkoxy is meant to include groups where there are ten or fewer atoms in the substituent, preferably six or fewer. A "lower alkyl", for example, refers to an alkyl group that contains ten or fewer carbon atoms, preferably six or fewer. In certain embodiments, acyl, acyloxy, alkyl, alkenyl, alkynyl, or alkoxy substituents defined herein are respectively lower acyl, lower acyloxy, lower alkyl, lower alkenyl, lower alkynyl, or lower alkoxy, whether they appear alone or in combination with other substituents, such as in the recitations hydroxyalkyl and aralkyl (in which case, for example, the atoms within the aryl group are not counted when counting the carbon atoms in the alkyl substituent).

The terms "polycyclyl", "polycycle", and "polycyclic" refer to two or more rings (e.g., cycloalkyls, cycloalkenyls, cycloalkynyls, aryls, heteroaryls, and/or heterocyclyls) in which two or more atoms are common to two adjoining rings, e.g., the rings are "fused rings". Each of the rings of the polycycle can be substituted or unsubstituted. In certain embodiments, each ring of the polycycle contains from 3 to 10 atoms in the ring, preferably from 5 to 7.

The term "sulfate" is art-recognized and refers to the group $—OSO_3H$, or a pharmaceutically acceptable salt thereof.

The term "sulfonamide" is art-recognized and refers to the group represented by the general formulae

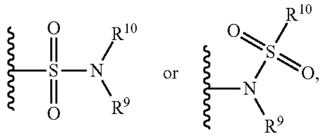

wherein $R^9$ and $R^{10}$ independently represents hydrogen or hydrocarbyl.

The term "sulfoxide" is art-recognized and refers to the group —S(O)—.

The term "sulfonate" is art-recognized and refers to the group $SO_3H$, or a pharmaceutically acceptable salt thereof.

The term "sulfone" is art-recognized and refers to the group $—S(O)_2—$.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate.

The term "thioalkyl", as used herein, refers to an alkyl group substituted with a thiol group.

The term "thioester", as used herein, refers to a group $—C(O)SR^9$ or $—SC(O)R^9$ wherein $R^9$ represents a hydrocarbyl.

The term "thioether", as used herein, is equivalent to an ether, wherein the oxygen is replaced with a sulfur.

The term "urea" is art-recognized and may be represented by the general formula

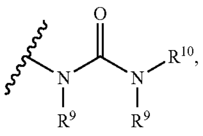

wherein $R^9$ and $R^{10}$ independently represent hydrogen or a hydrocarbyl.

The term "modulate" as used herein includes the inhibition or suppression of a function or activity (such as cell proliferation) as well as the enhancement of a function or activity.

The phrase "pharmaceutically acceptable" is art-recognized. In certain embodiments, the term includes compositions, excipients, adjuvants, polymers and other materials and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable salt" or "salt" is used herein to refer to an acid addition salt or a basic addition salt which is suitable for or compatible with the treatment of patients.

The term "pharmaceutically acceptable acid addition salt" as used herein means any non-toxic organic or inorganic salt of any base compounds represented by Formula I. Illustrative inorganic acids which form suitable salts include hydrochloric, hydrobromic, sulfuric and phosphoric acids, as well as metal salts such as sodium monohydrogen orthophosphate and potassium hydrogen sulfate. Illustrative organic acids that form suitable salts include mono-, di-, and tricarboxylic acids such as glycolic, lactic, pyruvic, malonic, succinic, glutaric, fumaric, malic, tartaric, citric, ascorbic, maleic, benzoic, phenylacetic, cinnamic and salicylic acids, as well as sulfonic acids such as p-toluene sulfonic and methanesulfonic acids. Either the mono or di-acid salts can be formed, and such salts may exist in either a hydrated, solvated or substantially anhydrous form. In general, the acid addition salts of compounds of Formula I are more soluble in water and various hydrophilic organic solvents, and generally demonstrate higher melting points in comparison to their free base forms. The selection of the appropriate salt will be known to one skilled in the art. Other non-pharmaceutically acceptable salts, e.g., oxalates, may be used, for example, in the isolation of compounds of Formula I for laboratory use, or for subsequent conversion to a pharmaceutically acceptable acid addition salt.

The term "pharmaceutically acceptable basic addition salt" as used herein means any non-toxic organic or inorganic base addition salt of any acid compounds represented by Formula I or any of their intermediates. Illustrative inorganic bases which form suitable salts include lithium, sodium, potassium, calcium, magnesium, or barium hydroxide. Illustrative organic bases which form suitable salts include aliphatic, alicyclic, or aromatic organic amines such as methylamine, trimethylamine and picoline or ammonia. The selection of the appropriate salt will be known to a person skilled in the art.

Many of the compounds useful in the methods and compositions of this disclosure have at least one stereogenic center in their structure. This stereogenic center may be present in a R or a S configuration, said R and S notation is used in correspondence with the rules described in Pure Appl. Chem. (1976), 45, 11-30. The disclosure contemplates all stereoisomeric forms such as enantiomeric and diastereoisomeric forms of the compounds, salts, prodrugs or mixtures thereof (including all possible mixtures of stereoisomers). See, e.g., WO 01/062726.

Furthermore, certain compounds which contain alkenyl groups may exist as Z (zusammen) or E (entgegen) isomers. In each instance, the disclosure includes both mixture and separate individual isomers.

Some of the compounds may also exist in tautomeric forms. Such forms, although not explicitly indicated in the formulae described herein, are intended to be included within the scope of the present disclosure.

"Prodrug" or "pharmaceutically acceptable prodrug" refers to a compound that is metabolized, for example hydrolyzed or oxidized, in the host after administration to form the compound of the present disclosure (e.g., compounds of formula I). Typical examples of prodrugs include compounds that have biologically labile or cleavable (protecting) groups on a functional moiety of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, or dephosphorylated to produce the active compound. Examples of prodrugs using ester or phosphoramidate as biologically labile or cleavable (protecting) groups are disclosed in U.S. Pat. Nos. 6,875,751, 7,585,851, and 7,964,580, the disclosures of which are incorporated herein by reference. The prodrugs of this disclosure are metabolized to produce a compound of Formula I. The present disclosure includes within its scope, prodrugs of the compounds described herein. Conventional procedures for the selection and preparation of suitable prodrugs are described, for example, in "Design of Prodrugs" Ed. H. Bundgaard, Elsevier, 1985.

The phrase "pharmaceutically acceptable carrier" as used herein means a pharmaceutically acceptable material, composition or vehicle, such as a liquid or solid filter, diluent, excipient, solvent or encapsulating material useful for formulating a drug for medicinal or therapeutic use.

The term "Log of solubility", "LogS" or "logS" as used herein is used in the art to quantify the aqueous solubility of a compound. The aqueous solubility of a compound significantly affects its absorption and distribution characteristics. A low solubility often goes along with a poor absorption. LogS value is a unit stripped logarithm (base 10) of the solubility measured in mol/liter.

EXPERIMENTALS

Table 1 lists the abbreviations used in this paragraph and in the Intermediates and Examples sections as far as they are not explained within the text body.

TABLE 1

| Abbreviation | Meaning |
|---|---|
| AcOH | acetic acid (ethanoic acid) |
| aq. | aqueous |
| Boc | t-butoxycarbonyl |
| BOP | (benzotriazol-1-yloxy)tris(dimethylamino)phosphonium hexafluorophosphate |
| br | broad |
| CI | chemical ionisation |
| $Cs_2CO_3$ | caesium carbonate |
| d | doublet |
| DAD | diode array detector |
| DBU | 1,8-diazabicyclo(5.4.0)undec-7-ene |
| DCC | N,N'-dicyclohexylcarbodiimide |
| DCM | dichloromethane |
| dd | double-doublet |
| DIC | N,N'-diisopropylcarbodiimide |
| DIPEA | diisopropylethylamine |
| DMA | Dimethylacetamide |
| DMF | N,N-dimethylformamide |
| DMSO | dimethyl sulfoxide |
| dt | double-triplet |
| EDC | 1-ethyl-3-(3-dimethylaminopropyl)carbodiimide |
| ELSD | Evaporative Light Scattering Detector |
| EtOAc | ethyl acetate |
| EtOH | ethanol |
| eq. | equivalent |
| ESI | electrospray (ES) ionisation |
| h | hour |
| HATU | 1-[bis(dimethylamino)methylene]-1H-1,2,3-triazolo[4,5-b]pyridinium 3-oxid hexafluorophosphate |
| HBTU | (o-benzotriazole-10yl)-N,N,N',N,-tetramethyluronium hexafluorophosphate |
| HCl | hydrochloric acid |
| HPLC | high performance liquid chromatography |
| $K_2CO_3$ | potassium carbonate |
| LC-MS | liquid chromatography mass spectrometry |
| m | multiplet |
| mCPBA | meta-Chloroperbenzoic acid |
| min | minute |
| MeCN | acetonitrile |
| MeOH | methanol |
| MS | mass spectrometry |
| MTBE | methyl-tert-butyl ether |
| NaCl | sodium chloride |
| $NaHCO_3$ | sodium hydrogen carbonate or sodium bicarbonate |
| NMR | nuclear magnetic resonance spectroscopy: chemical shifts (δ) are given in ppm. The chemical shifts were corrected by setting the DMSO signal to 2.50 ppm unless otherwise stated. |
| $Na_2SO_4$ | sodium sulfate |
| PDA | Photo Diode Array |
| Pd/C | palladium on activated charcoal |
| PyBOP | (benzotriazol-1-yloxy)tripyrrolidinophosphonium hexafluorophosphate |
| q | quartet |
| r.t. or rt or RT | room temperature |
| Rt | retention time (as measured either with HPLC or UPLC) in minutes |
| s | singlet |
| sat. | saturated |
| SFC | supercritical fluid chromatography |
| SIBX | stabilized 2-iodoxybenzoic acid |
| SM | starting material |
| SQD | Single-Quadrupole-Detector |
| T3P | propylphosphonic anhydride |
| t | triplet |
| td | triple-doublet |
| TEA | triethylamine |
| TFA | trifluoroacetic acid |
| THF | tetrahydrofuran |
| UPLC | ultra performance liquid chromatography |
| XPhos Pd G3; or XPhos-Pd-G3 | (2-Dicyclohexylphosphino-2',4',6'-triisopropyl-1,1'-biphenyl)[2-(2'-amino-1,1'-biphenyl)]palladium(II) methanesulfonate |

Other abbreviations have their meanings customary per se to the skilled person.

The various aspects of the invention described in this application are illustrated by the following examples which are not meant to limit the invention in any way.

Specific Experimental Descriptions

NMR peak forms in the following specific experimental descriptions are stated as they appear in the spectra, possible higher order effects have not been considered.

Reactions employing microwave irradiation may be run with a Biotage Initiator® microwave oven optionally equipped with a robotic unit. The reported reaction times employing microwave heating are intended to be understood as fixed reaction times after reaching the indicated reaction temperature.

The compounds and intermediates produced according to the methods of the invention may require purification. Purification of organic compounds is well known to the person skilled in the art and there may be several ways of purifying the same compound. In some cases, no purification may be necessary. In some cases, the compounds may be purified by crystallization. In some cases, impurities may be stirred out using a suitable solvent. In some cases, the compounds may be purified by chromatography, particularly flash column chromatography, using for example pre-packed silica gel cartridges, e.g. from Separtis such as Isolute® Flash silica gel or Isolute® Flash $NH_2$ silica gel in combination with a Isolera® autopurifier (Biotage) and eluents such as gradients of e.g. hexane/ethyl acetate or DCM/ methanol. In some cases, the compounds may be purified by preparative HPLC using for example a Waters autopurifier equipped with a diode array detector and/or on-line electrospray ionization mass spectrometer in combination with a suitable prepacked reverse phase column and eluents such as gradients of water and acetonitrile which may contain additives such as trifluoroacetic acid, formic acid or aqueous ammonia.

In some cases, purification methods as described above can provide those compounds of the present invention which possess a sufficiently basic or acidic functionality in the form of a salt, such as, in the case of a compound of the present invention which is sufficiently basic, a trifluoroacetate or formate salt for example, or, in the case of a compound of the present invention which is sufficiently acidic, an ammonium salt for example. A salt of this type can either be transformed into its free base or free acid form, respectively, by various methods known to the person skilled in the art, or be used as salts in subsequent biological assays. It is to be understood that the specific form (e.g. salt, free base etc) of a compound of the present invention as isolated as described herein is not necessarily the only form in which said compound can be applied to a biological assay in order to quantify the specific biological activity.

The percentage yields reported in the following examples are based on the starting component that was used in the lowest molar amount. Air and moisture sensitive liquids and solutions were transferred via syringe or cannula and introduced into reaction vessels through rubber septa. Commercial grade reagents and solvents were used without further purification. The term “concentrated in vacuo” refers to the use of a Buchi rotary evaporator at a minimum pressure of approximately 15 mm of Hg. All temperatures are reported uncorrected in degrees Celsius (° C.).

In order that this invention may be better understood, the following examples are set forth. These examples are for the purpose of illustration only, and are not to be construed as limiting the scope of the invention in any manner. All publications mentioned herein are incorporated by reference in their entirety.

UPLC-MS Standard Procedures

UPLC-MS-data given in the subsequent specific experimental descriptions refer (unless otherwise noted) to the following conditions:

Method 1:

| | |
|---|---|
| System: | Waters Acquity UPLC-MS: Binary Solvent Manager, Sample Manager/Organizer, Column Manager, PDA, ELSD, SQD 3001 |
| Column: | Acquity BEH C18 1.7 50 × 2.1 mm |
| Solvent: | A = water + 0.1% vol. formic acid (99%)<br>B = acetonitrile |
| Gradient: | 0-1.6 min 1-99% B, 1.6-2.0 min 99% B |
| Flow: | 0.8 mL/min |
| Temperature: | 60° C. |
| Injection: | 2.0 μL |
| Detection: | DAD scan range 210-400 nm<br>MS ESI+, ESI−, scan range 160-1000 m/z<br>ELSD |

Method 2:

| | |
|---|---|
| System: | Waters Acquity UPLC-MS: Binary Solvent Manager, Sample Manager/Organizer, Column Manager, PDA, ELSD, SQD 3001 |
| Column: | Acquity BEH C18 1.7 50 × 2.1 mm |
| Solvent: | A = water + 0.2% vol. ammonia (32%)<br>B = acetonitrile |
| Gradient: | 0-1.6 min 1-99% B, 1.6-2.0 min 99% B |
| Flow: | 0.8 mL/min |
| Temperature: | 60° C. |
| Injection: | 2.0 μL |
| Detection: | DAD scan range 210-400 nm<br>MS ESI+, ESI−, scan range 160-1000 m/z<br>ELSD |

Method 3:

| | | | | |
|---|---|---|---|---|
| Instrument | | SHIMADZU LCMS-2020; | | |
| Software | | LabSolution Version 5.97SP1 | | |
| HPLC | Column | Kinetex ® EVO C18 2.1 × 30 mm 5 um | | |
| | Mobile Phase | A: 0.0375% TFA in water (v/v)<br>B: 0.01875% TFA in Acetonitrile (v/v) | | |
| | | Time(min) | B(%) | Flow(mL/min) |
| | Gradient | 0.0 | 5 | 0.8 |
| | | 3.0 | 95 | 0.8 |
| | | 3.60 | 95 | 0.8 |
| | | 3.61 | 5 | 0.8 |
| | | 4.00 | 5 | 0.8 |
| | Column Temp | 40° C. | | |
| | Detector | PDA (220 nm&254 nm) | | |
| MS | Ionization source | ESI | | |
| | Drying Gas | N2 | | |
| | Drying Gas Flow | 15(L/min) | | |
| | DL Voltage | 120(v) | | |
| | Qarray DC Voltage | 20(V) | | |
| | MS Polarity | Positive | | |
| | MS Mode | Scan | | |
| | Mass range | 100-1000 | | |

Method 4:

| | |
|---|---|
| System: | Waters Acquity UPLC-MS: Binary Solvent Manager, Sample Manager/Organizer, Column Manager, PDA, SQD 3001 |
| Column: | XBridge C18 1.7 50 × 2.1 mm |
| Solvent: | A = water + 0.1% vol. formic acid (99%)<br>B = acetonitrile |
| Gradient: | 0-0.5 min, 5% B, 0.5-4.0 min 5-95% B, 4.0-4.5 min 95% B |
| Flow: | 0.6 mL/min |
| Temperature: | 25° C. |
| Injection: | 2.0 μL |
| Detection: | DAD scan range 210-400 nm<br>MS ESI+, ESI−, scan range 100-1500 m/z |

Preparative HPLC Conditions

“Purification by preparative HPLC” in the subsequent experimental descriptions refers to the following conditions (unless otherwise noted):

Flash Column Chromatography Conditions

“Purification by (flash) column chromatography” as stated in the subsequent specific experimental descriptions refers to the use of a Biotage Isolera purification system or a Teledyne Isco Combiflash purification system. For technical specifications see “Biotage product catalogue” or see “Combiflash NextGen Synthesis”.

Chemical names were generated using the ACD/Name software from ACD/Labs. In some cases generally accepted names of commercially available reagents were used in place of ACD/Name generated names.

Optical rotations were measured using a JASCO P2000 Polarimeter. Typical, a solution of the compound with a concentration of 1 mg/mL to 15 mg/mL was used for the measurement. The specific rotation $[\alpha]_D$ was calculated according to the following formula:

$$[\alpha]D = \frac{\propto}{\beta \times d}$$

In this equation, a is the measured rotation in degrees; d is the path length in decimeters and β is the concentration in g/mL.

INTERMEDIATE SYNTHESIS

Intermediate 1

N-{4-[(3-amino-6-fluoropyridin-2-yl)ethynyl]pyridin-2-yl}acetamide

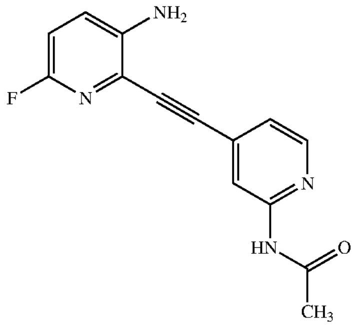 [SMILES: CC(=O)Nc1cc(C#Cc2nc(F)ccc2N)ccn1]

N-(4-Ethynylpyridin-2-yl)acetamide (799 mg, 4.99 mmol, CAS-RN:[1445876-40-3]), 2-bromo-6-fluoropyridin-3-amine (1.00 g, 5.24 mmol, CAS-RN:[1068976-51-1]), bis(triphenylphosphine) palladium (II) dichloride (350 mg, 499 μmol; CAS-RN:[13965-03-2]), copper (I)-iodide (19.0 mg, 99.7 μmol; CAS-RN:[7681-65-4]) and triethylamine (6.3 mL, 45 mmol) were dissolved in 2.1 mL DMF and stirred at 80° C. for 1.5 hours under Argon atmosphere. The reaction mixture was concentrated under reduced pressure and purified by flash chromatography (55 g column, aminophase; dichloromethane/ethanol 0%-5%) to provide the target compound in 65% purity: 168 mg. LC-MS (Method 1): $R_t$=0.84 min; MS (ESIpos): m/z=271 $[M+H]^+$. $^1$H-NMR (400 MHz, DMSO-d6): δ [ppm]=2.11 (s, 3H), 5.87 (s, 2H), 6.99 (dd, 1H), 7.31-7.34 (m, 1H), 7.36 (dd, 1H), 8.23 (s, 1H), 8.35 (dd, 1H), 10.63 (s, 1H).

Intermediate 2

N-{2-[(2-acetamidopyridin-4-yl)ethynyl]-6-fluoropyridin-3-yl}-2,2,2-trifluoroacetamide

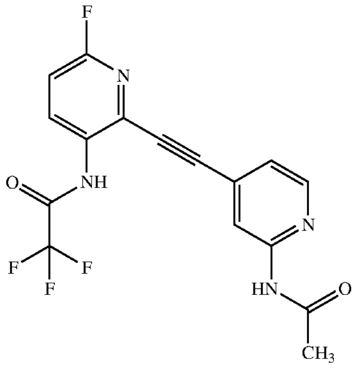 [SMILES: CC(=O)Nc1cc(C#Cc2nc(F)ccc2NC(=O)C(F)(F)F)ccn1]

N-{4-[(3-Amino-6-fluoropyridin-2-yl)ethynyl]pyridin-2-yl}acetamide (see Intermediate 1, 830 mg) and triethylamine (1.3 mL, 9.2 mmol) were suspended in 13 mL dichloromethane and cooled down with an ice bath. Then trifluoroacetic anhydride (640 μL, 4.6 mmol) was added portion wise. The reaction mixture was stirred at 0° C. for 2 hours under Argon atmosphere. To the reaction mixture aqueous saturated sodium hydrogen carbonate solution and dichloromethane were added. The undissolved precipitate was filtered off, washed with water and dichloromethane/isopropanole (7:3) and dried at 50° C. under vacuo to provide the target compound in 85% purity: 304 mg. LC-MS (Method 2): $R_t$=0.51 min; MS (ESIpos): m/z=368 $[M+H]^+$. $^1$H-NMR (400 MHz, DMSO-d6) δ[ppm]=2.09-2.15 (m, 3H), 7.19 (dd, 1H), 7.44 (dd, 1H), 8.17 (dd, 1H), 8.24 (s, 1H), 8.41 (dd, 1H), 10.71 (s, 1H), 11.66 (br s, 1H).

Intermediate 3

N-{4-[5-fluoro-3-(pyridin-2-yl)-1H-pyrrolo[3,2-b]pyridin-2-yl]pyridin-2-yl}acetamide

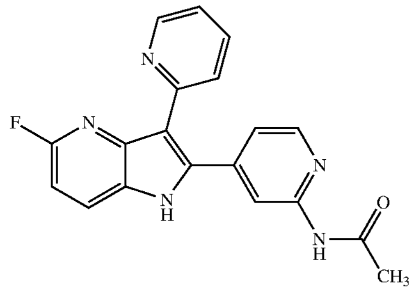 [SMILES: CC(=O)Nc1cc(-c2[nH]c3ccc(F)nc3c2-c2ccccn2)ccn1]

N-{2-[(2-Acetamidopyridin-4-yl)ethynyl]-6-fluoropyridin-3-yl}-2,2,2-trifluoroacetamide (see Intermediate 2, 250 mg), 2-bromopyridine (75 UL, 790 μmol), tetrakis(triphenylphosphine)palladium (39.4 mg, 34.1 μmol; CAS-RN: [14221-01-3]) and cesiumcarbonate 645 mg, 1.98 mmol) were dissolved in 5.7 mL acetonitrile and stirred at 100° C. under Argon atmosphere in a sealed vessel for 1 h. The reaction mixture was combined with another batch started from N-{2-[(2-Acetamidopyridin-4-yl)ethynyl]-6-fluoropyridin-3-yl}-2,2,2-trifluoroacetamide (see Intermediate 2, 50 mg). The undissolved precipitated was filtered off and washed with dichloromethane and methanol. The filtrate was concentrated under reduced pressure and purified by HPLC chromatography under basic conditions in 2 portions. The product containing fractions were concentrated under reduced pressure and treated with dichloromethane and ethanol. The undissolved precipitate was filtered off, washed with dichloromethane and dried at 50° C. under vacuo to provide the target compound in 88% purity: 26 mg. LC-MS (Method 2): $R_t$=0.89 min; MS (ESIpos): m/z=348 $[M+H]^+$. $^1$H-NMR (400 MHZ, DMSO-d6) δ[ppm]=2.08 (s, 3H), 7.00 (dd, 1H), 7.12 (dd, 1H), 7.27 (ddd, 1H), 7.83-7.97 (m, 2H), 8.05 (dd, 1H), 8.24-8.33 (m, 2H), 8.45 (d, 1H), 10.56 (s, 1H), 12.15-12.50 (m, 1H).

Intermediate 4

4-[5-fluoro-3-(pyridin-2-yl)-1H-pyrrolo[3,2-b]pyridin-2-yl]pyridin-2-amine

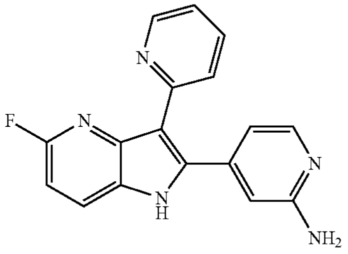 [SMILES: Nc1cc(-c2[nH]c3ccc(F)nc3c2-c2ccccn2)ccn1]

N-{4-[5-Fluoro-3-(pyridin-2-yl)-1H-pyrrolo[3,2-b]pyridin-2-yl]pyridin-2-yl}acetamide (see Intermediate 3, 180 mg) was dissolved in 39 mL methanol and treated with aqueous sodium hydroxide solution (5.2 mL, 1.0 M, 5.2 mmol). The reaction mixture was stirred at 80° C. for 1.5 hours under Argon atmosphere. Further aqueous sodium hydroxide solution (2.1 mL, 2.0 M, 4.1 mmol) were added and it was stirred at 80° C. for 6.5 hours under Argon atmosphere. The reaction mixture was concentrated under reduced pressure and diluted with water. The undissolved precipitate was filtered off and washed with water until the filtrate was not basic anymore. The residue was dried at 50° C. under vacuum to provide the analytically pure target compound: 139 mg. LC-MS (Method 2): $R_t$=0.85 min; MS (ESIpos): m/z=306 $[M+H]^+$. $^1$H-NMR (400 MHZ, DMSO-d6) δ[ppm]=6.02 (s, 2H), 6.50 (dd, 1H), 6.59 (s, 1H), 6.96 (dd, 1H), 7.23-7.32 (m, 1H), 7.81-7.92 (m, 3H), 7.99 (dd, 1H), 8.51 (dt, 1H), 11.81-12.54 (m, 1H).

Intermediate 5

N-{4-[(3-aminopyridin-2-yl)ethynyl]pyridin-2-yl}acetamide

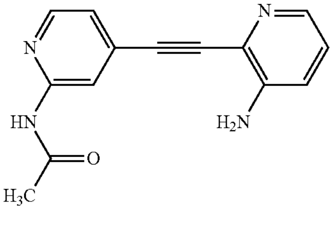 [SMILES: CC(=O)Nc1cc(C#Cc2ncccc2N)ccn1]

To a stirred solution of N-(4-ethynylpyridin-2-yl)acetamide (CAS 1445876-40-3, 2.00 g, 12.5 mmol) and 2-bromopyridin-3-amine (CAS 39856-58-1, 2.59 g, 15.0 mmol) in DMF (34 mL) was added triethylamine (7.0 ml, 50 mmol; CAS-RN:[121-44-8]), $Pd(PPh_2)_3Cl_2$ (438 mg, 624 μmol; CAS-RN:[13965-03-2]) and CuI (238 mg, 1.25 mmol; CAS-RN:[7681-65-4]) and the flask was twice degassed and backfilled with argon. The mixture was stirred at 80° C. for 1 h. Ethyl acetate was added and the mixture was washed with half-saturated sodium chloride solution (three times), dried (sodium sulfate), filtered and the solvent was removed in vacuum. Silicagel chromatography (Gradient: dichloromethane/ethanol 0-25%) gave 1.72 g of the title compound. LC-MS (Method 1): $R_t$=0.59 min; MS (ESIpos): m/z=253 $[M+H]^+$. $^1$H-NMR (400 MHZ, DMSO-$d_6$): δ [ppm]=10.62 (s, 1H), 8.35 (d, 1H), 8.23 (s, 1H), 7.81 (br s, 1H), 7.35 (dd, 1H), 7.18-7.08 (m, 2H), 5.83 (s, 2H), 2.11 (s, 3H).

Intermediate 6

N-{2-[(2-acetamidopyridin-4-yl)ethynyl]pyridin-3-yl}-2,2,2-trifluoroacetamide

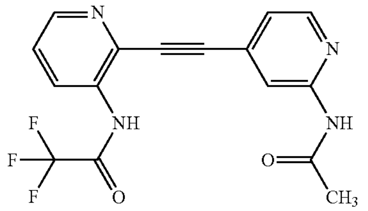 [SMILES: CC(=O)Nc1cc(C#Cc2ncccc2NC(=O)C(F)(F)F)ccn1]

A stirred solution of N-{4-[(3-aminopyridin-2-yl)ethynyl]pyridin-2-yl}acetamide (see Intermediate 5, 560 mg, 2.22 mmol), and triethylamine (620 μl, 4.4 mmol; CAS-RN:[121-44-8]) in dichloromethane (25 ml) was cooled to 0° C., trifluoroacetic anhydride (470 μl, 3.3 mmol; CAS-RN:[407-25-0]) was slowly added and the mixture was stirred at 0° C. for 2 h. Dichloromethane and an aqueous solution of sodium bicarbonate were added and the mixture was extracted with a mixture of dichloromethane and methanol. The organic phase was washed with saturated sodium chloride solution, dried (sodium sulfate), filtered and the solvent was removed in vacuum. The residue was triturated with a mixture of dichloromethane and hexane. The mixture was filtered, the solid was discarded and the solution was concentrated to dryness to give 256 mg (68% purity) of the title compound. LC-MS (Method 1): $R_t$=0.88 min; MS (ESIpos): m/z=349 $[M+H]^+$.

Intermediate 7

N-{4-[3-(pyridin-2-yl)-1H-pyrrolo[3,2-b]pyridin-2-yl]pyridin-2-yl}acetamide

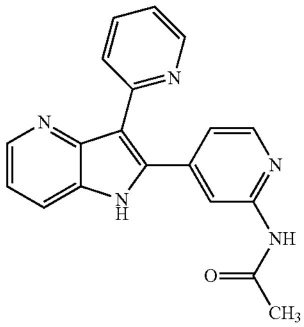 [SMILES: CC(=O)Nc1cc(-c2[nH]c3cccnc3c2-c2ccccn2)ccn1]

To a stirred solution of N-{2-[(2-acetamidopyridin-4-yl)ethynyl]pyridin-3-yl}-2,2,2-trifluoroacetamide (see Intermediate 6, 250 mg, 65% purity, 467 μmol) and 2-bromopyridine (67 μl, 700 μmol; CAS-RN:[109-04-6]) in acetonitrile (2.6 mL) in a sealed tube was added dicesium carbonate (456 mg, 1.40 mmol; CAS-RN:[534-17-8]) and tetrakis (triphenylphosphin)palladium (27.0 mg, 23.3 μmol; CAS- RN:[14221-01-3]) and the flask was twice degassed and backfilled with argon. The mixture was heated to 80° C. for 3 h and then to 100° C. for 1 h. Water was added, the mixture was extracted with a mixture of dichloromethane and methanol. The organic phase was dried (sodium sulfate), filtered and the solvent was removed in vacuum. Silicagel chromatography (Gradient: dichloromethane/ethanol 0-25%) gave 26.0 mg of the title compound. LC-MS (Method 1): $R_t$=0.59 min; MS (ESIpos): m/z=330 $[M+H]^+$. $^1$H-NMR (400 MHZ, DMSO-d6): δ [ppm]=12.09 (s, 1H), 10.55 (s, 1H), 8.48-8.41 (m, 2H), 8.31 (s, 1H), 8.30-8.27 (m, 1H), 8.15-8.10 (m, 1H), 7.91-7.83 (m, 2H), 7.29-7.22 (m, 2H), 7.15 (dd, 1H), 2.08 (s, 3H).

Intermediate 8

4-[3-(pyridin-2-yl)-1H-pyrrolo[3,2-b]pyridin-2-yl]pyridin-2-amine

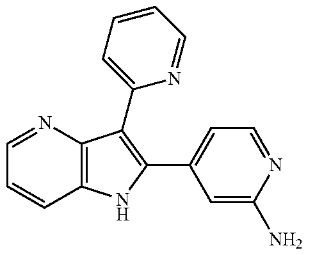 [SMILES: Nc1cc(-c2[nH]c3cccnc3c2-c2ccccn2)ccn1]

To a stirred solution of N-{4-[3-(pyridin-2-yl)-1H-pyrrolo[3,2-b]pyridin-2-yl]pyridin-2-yl}acetamide (see Intermediate 7, 25.0 mg, 75.9 μmol) in methanol (5.8 ml) was added an aqueous solution of sodium hydroxide (760 μl, 1.0 M, 760 μmol; CAS-RN:[1310-73-2]) and the mixture was stirred at 80° C. for 3 h. The mixture was concentrated in vacuum. Water was added and the precipitate was collected by filtration to give 21.0 mg of the title compound. LC-MS (Method 2): $R_t$=0.73 min; MS (ESIpos): m/z=288 $[M+H]^+$. $^1$H-NMR (400 MHZ, DMSO-d6) δ [ppm]: 1.231 (1.34), 2.084 (0.74), 2.518 (12.32), 2.523 (8.29), 3.372 (1.51), 5.995 (16.00), 6.511 (8.09), 6.515 (8.49), 6.525 (8.10), 6.528 (8.77), 6.620 (10.35), 6.622 (12.25), 6.624 (11.64), 7.207 (7.71), 7.219 (7.66), 7.228 (7.84), 7.234 (5.17), 7.237 (6.52), 7.240 (8.83), 7.246 (4.71), 7.249 (5.30), 7.253 (5.58), 7.256 (4.84), 7.265 (5.32), 7.268 (4.88), 7.813 (7.93), 7.817 (9.14), 7.822 (4.63), 7.826 (4.81), 7.834 (8.65), 7.838 (8.53), 7.841 (7.64), 7.846 (7.30), 7.860 (4.63), 7.865 (5.18), 7.872 (9.90), 7.885 (9.50), 8.028 (5.70), 8.031 (9.22), 8.033 (5.81), 8.048 (4.82), 8.051 (7.59), 8.404 (7.91), 8.408 (8.64), 8.415 (8.16), 8.419 (7.99), 8.476 (4.99), 8.479 (5.68), 8.481 (5.85), 8.483 (5.16), 8.488 (5.27), 8.491 (6.08), 8.493 (5.68), 8.495 (4.84), 11.934 (4.71).

Intermediate 9: N-(4-bromopyridin-2-yl)acetamide

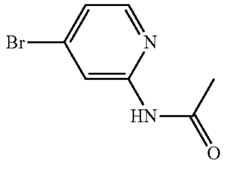

To a stirred solution of 4-bromopyridin-2-amine (100 g, 578 mmol, CAS-RN:[84249-14-9]) in DCM (1 L) was added $Ac_2O$ (88.5 g, 867 mmol, CAS-RN: []). The resulting mixture was stirred at 25° C. for 16 h to give a yellow solution. A saturated aqueous solution of $NaHCO_3$ (1000 mL) was added to adjust the solution to pH 7~8. The resulting mixture was extracted with CH2Cl2 (1000 mL×2). The combined organic phases were dried (sodium sulfate), filtered, and the solvent was removed in vacuo to give 120 g of the title compound as a white solid, which was used without further purification. $^1$H NMR (400 MHZ, CHLOROFORM-d) δ=8.47 (s, 1H), 8.12 (s, 1H), 8.07 (d, J=5.2 Hz, 1H), 7.21 (dd, J=1.6, 5.2 Hz, 1H), 2.22 (s, 3H).

Intermediate 10: N-(4-((trimethylsilyl)ethynyl)pyridin-2-yl)acetamide

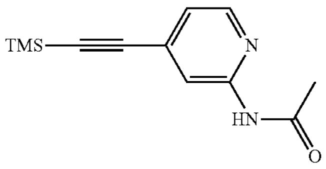 [SMILES: CC(=O)Nc1cc(C#C[Si](C)(C)C)ccn1]

To a solution of N-(4-bromo-2-pyridyl)acetamide (120 g, 558 mmol, see Intermediate 9) and ethynyl(trimethyl)silane (60.2 g, 613 mmol, CAS-RN:[1066-54-2]) in Et3N (1.0 L) was added CuI (4.25 g, 22.3 mmol, CAS-RN:[7681-65-4]) and $Pd(PPh_3)_2Cl_2$ (7.83 g, 11.1 mmol, CAS-RN: [13965-03-2]). The resulting mixture was stirred at 75° C. for 3 h to give a black suspension. The reaction mixture was concentrated in vacuo to give a brown oil. The residue was dissolved in a 1:1 mixture of EtOAc/Petroleum Ether (1 L), and the resulting mixture was stirred for 0.5 hour to give a brown suspension. The suspension was filtered, the filtrate was collected and concentrated in vacuo to give 160 g of the title compound as a yellow solid, which was used without further purification. $^1$H NMR (400 MHZ, DMSO-d6) δ=10.61 (s, 1H), 8.30 (d, J=5.6 Hz, 1H), 8.09 (s, 1H), 7.10 (dd, J=1.2, 5.2 Hz, 1H), 2.10 (s, 3H), 0.31-0.19 (m, 9H)

Intermediate 11: N-(4-ethynylpyridin-2-yl)acetamide

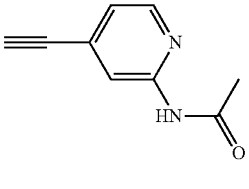

To a stirred solution of N-[4-(2-trimethylsilylethynyl)-2-pyridyl]acetamide (100 g, 430 mmol, see Intermediate 10) in MeOH (1000 mL) was added $K_2CO_3$ (178 g, 1.29 mol, CAS-RN:[584-08-7]). The resulting mixture was stirred at 25° C. for 1 h. The resulting suspension was filtered, and the filtrate was diluted with $H_2O$ (1000 mL). The resulting solution was extracted with EtOAc (3000 mL×3). The combined organic layers were dried (sodium sulfate), filtered, and the solvent removed in vacuo. The crude product was triturated with a 10:1 mixture of Petroleum Ether: EtOAc to give 60 g of the title compound as a yellow solid, which was used without further purification. LC-MS (Method 3): $R_t$=0.279 min, MS (ESIpos) m/z=161.2 $[M+H]^+$ Intermediate 12: 4-chloro-6-(2,2-difluoroethoxy)pyrimidin-5-amine

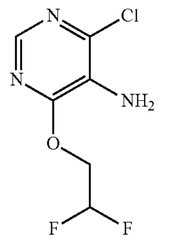 [SMILES: Nc1c(Cl)ncnc1OCC(F)F]

A stirred solution of 2,2-difluoroethanol (40.0 g, 487 mmol, CAS-RN:[359-13-7]) in THF (2000 mL) was cooled to at 0° C. NaH (21.4 g, 536 mmol, 60% purity, CAS-RN: [7646-69-7]) was added in one portion, and the resulting mixture was stirred for 0.5 h. Then 4,6-dichloropyrimidin-5-amine (80 g, 487 mmol, CAS-RN:[5413-85-4]) was added, and the resulting mixture was stirred at 80° C. for 3 h to give a yellow solution. The reaction mixture was poured into water (1000 mL). The resulting aqueous phase was extracted with EtOAc (1000 mL×2). The combined organic phase was washed with brine (1200 mL×2), dried (sodium sulfate), filtered, and the solvent removed in vacuo. The residue was purified by normal phase chromatography on silica gel (column height: 250 mm, diameter: 100 mm, 100-200 mesh silica gel, Petroleum ether/Ethyl acetate=100/1-3/1) to afford 150 g or the title compound as a yellow oil. $^1H$ NMR (400 MHZ, DMSO-$d_6$) δ 7.92 (s, 1H), 6.56-6.22 (m, 1H), 5.46 (s, 2H), 4.70-4.62 (m, 2H).

Intermediate 13: 4-(2,2-difluoroethoxy)-6-iodopyrimidin-5-amine

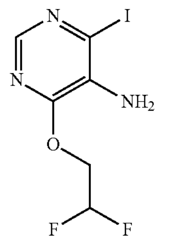 [SMILES: Nc1c(I)ncnc1OCC(F)F]

4-chloro-6-(2,2-difluoroethoxy)pyrimidin-5-amine (100 g, 477 mmol, see Intermediate 12) and NaI (214 g, 1.43 mol, CAS-RN:[7681-82-5]) were dissolved in a concentrated aqueous solution of HI (1 L, CAS-RN:[10034-85-2]) and the resulting mixture was stirred at 25° C. for 16 h to give a brown suspension. The residue was poured into water (300 mL) and then adjust to pH=8 with a saturated solution of $NaHCO_3$. The aqueous phase was extracted with EtOAc (1000 mL×2). The combined organic phase was washed with brine (800 mL×2), dried (sodium sulfate), filtered, and the solvent removed in vacuo to give 145 g of the title compound as a yellow oil, which was used without further purification. LC-MS (Method 3): $R_t$=0.329 min, MS (ESIpos) m/z=301.8 $[M+H]^+$.

Intermediate 14: N-(4-((5-amino-6-(2,2-difluoroethoxy)pyrimidin-4-yl)ethynyl)pyridin-2-yl)acetamide

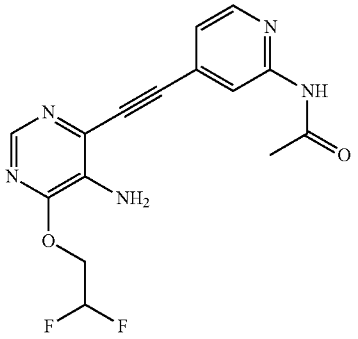 [SMILES: CC(=O)Nc1cc(C#Cc2ncnc(OCC(F)F)c2N)ccn1]

4-(2,2-difluoroethoxy)-6-iodo-pyrimidin-5-amine (76.8 g, 255 mmol, see Intermediate 13), N-(4-ethynyl-2-pyridyl) acetamide (45 g, 280 mmol, see intermediate 11), CuI (4.86 g, 25.5 mmol, CAS-RN:[7681-65-4]), $Pd(PPh_3)_2Cl_2$ (17.9 g, 25.5 mmol, CAS-RN:[13965-03-2]), and Et3N (77.5 g, 766 mmol, 106 mL, CAS-RN:[121-44-8]) were dissolved in MeCN (1500 mL). The resulting mixture was thoroughly degassed and purged with $N_2$ (3×), and then the mixture was stirred at 25° C. for 16 h under $N_2$ atmosphere. The resulting mixture was concentrated in vacuo to give a brown solid. The resulting residue was redissolved in MeCN (300 mL) then stirred at 25° C. for 1 h to give a yellow suspension. The suspension was filtered, and the filter cake was collected, washed with MeCN (50 mL×3), and dried in vacuo to give 55 g of the title compound as a yellow solid, which was used without further purification. LC-MS (Method 3): $R_t$=0.403 min, MS (ESIpos) m/z=334.1 $[M+H]^+$. $^1H$ NMR (400 MHZ, DMSO-$d_6$) δ=10.64 (s, 1H), 8.38 (d, J=4.0 Hz, 1H), 8.27 (s, 1H), 8.04 (s, 1H), 7.39 (dd, J=1.2, 5.2 Hz, 1H), 6.60-6.27 (m, 1H), 5.92 (s, 2H), 4.68 (dt, J=3.6, 14.8 Hz, 2H), 2.12 (s, 3H).

Intermediate 15: N-(4-((2-acetamidopyridin-4-yl)ethynyl)-6-(2,2-difluoroethoxy)pyrimidin-5-yl)-2,2,2-trifluoroacetamide

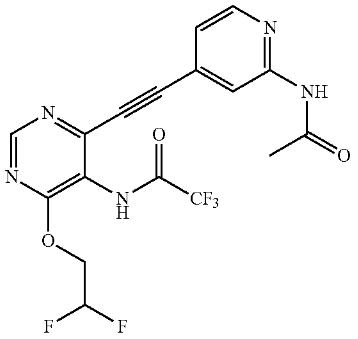 [SMILES: CC(=O)Nc1cc(C#Cc2ncnc(OCC(F)F)c2NC(=O)C(F)(F)F)ccn1]

To a stirred solution of N-[4-[2-[5-amino-6-(2,2-difluoroethoxy)pyrimidin-4-yl]ethynyl]-2-pyridyl]acetamide (55 g, 165 mmol, see intermediate 14) in $CH_2Cl_2$ (1000 mL) was added DIEA (106 g, 825 mmol, 143 mL, CAS-RN:[7087-68-5]) and TFAA (103 g, 495 mmol, 68.8 mL, CAS-RN: [407-25-0]). The resulting mixture was stirred at 0° C. for 1 h. The reaction mixture was diluted with brine (1000 mL) and extracted with EtOAc (1000 mL×3). The combined organic layers were washed with a saturated aqueous solution of $NH_4Cl$ (800 mL×3), dried (sodium sulfate), filtered, and the solvent removed in vacuo. The crude residue was triturated with MeCN to give 40 g of the title compound as a white solid, which was used without further purification. LC-MS (Method 3): $R_t$=0.376 min, MS (ESIpos) m/z=430.2 $[M+H]^+$, $^1H$ NMR (400 MHz, DMSO-$d_6$) δ=11.73 (s, 1H), 10.72 (s, 1H), 8.88 (s, 1H), 8.43 (d, J=5.2 Hz, 1H), 8.26 (s, 1H), 7.21 (dd, J=1.2, 5.2 Hz, 1H), 6.56-6.23 (m, 1H), 4.78 (dt, J=3.2, 14.8 Hz, 2H), 2.12 (s, 3H).

Intermediate 16: N-(4-(4-(2,2-difluoroethoxy)-7-(pyridin-2-yl)-5H-pyrrolo[3,2-d]pyrimidin-6-yl)pyridin-2-yl)acetamide

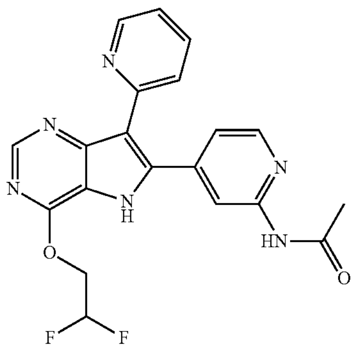 [SMILES: CC(=O)Nc1cc(-c2[nH]c3c(OCC(F)F)ncnc3c2-c2ccccn2)ccn1]

N-[4-[2-(2-acetamido-4-pyridyl)ethynyl]-6-(2,2-difluoroethoxy)pyrimidin-5-yl]-2,2,2-trifluoroacetamide (20 g, 46.5 mmol, see intermediate 15), 2-bromopyridine (11.0 g, 69.8 mmol, 6.65 mL, CAS-RN:[109-04-6]), $Pd(PPh_3)_4$ (5.38 g, 4.66 mmol, CAS-RN:[14221-01-3]), and $K_2CO_3$ (19.3 g, 139 mmol, CAS-RN:[584-08-7]) were dissolved in DMF (100 mL). The resulting mixture was thoroughly degassed and purged with $N_2$ (3×), and then the mixture was stirred at 100° C. for 16 h under an $N_2$ atmosphere. The reaction suspension was filtered to provide a liquid, which was concentrated in vacuo. The resulting residue was purified by column chromatography on alumina oxide ($Al_2O_3$, DCM: MeOH=10:1) to give 9 g of the title compound as a yellow solid. LC-MS (Method 3): $R_t$=0.295 min, MS (ESIpos) m/z=410.9 $[M+H]^+$. $^1H$ NMR (400 MHZ, DMSO-$d_6$) δ=12.85 (s, 1H), 10.54 (s, 1H), 8.56 (s, 1H), 8.44-8.39 (m, 1H), 8.31-8.26 (m, 2H), 8.06 (d, J=8.0 Hz, 1H), 7.86 (dt, J=1.8, 7.8 Hz, 1H), 7.26 (ddd, J=1.2, 4.8, 7.6 Hz, 1H), 7.18-7.12 (m, 1H), 6.69-6.34 (m, 1H), 4.91 (dt, J=3.2, 15.2 Hz, 2H), 2.10-2.07 (s, 3H).

Intermediate 17: 4-(4-(2,2-difluoroethoxy)-7-(pyridin-2-yl)-5H-pyrrolo[3,2-d]pyrimidin-6-yl)pyridin-2-amine

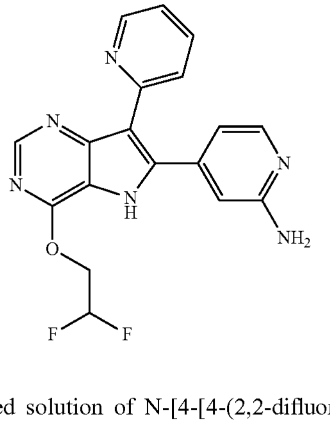

To a stirred solution of N-[4-[4-(2,2-difluoroethoxy)-7-(2-pyridyl)-5H-pyrrolo[3,2-d]pyrimidin-6-yl]-2-pyridyl]acetamide (9 g, 21.9 mmol, see Intermediate 16) in THF (100 mL) and $H_2O$ (100 mL) was added $LiOH·H_2O$ (5.52 g, 131 mmol, CAS-RN:[1310-66-3]). The resulting mixture was stirred at 40° C. for 26 h. The reaction mixture was diluted with $H_2O$ (50 mL) and extracted with THF (200 mL×3). The combined organic layers were dried (sodium sulfate), filtered, and the solvent removed in vacuo. The resulting residue was purified by column chromatography on alumina oxide ($Al_2O_3$, DCM:MeOH=10:1) to give 7 g of the title compound as a white solid. LC-MS (Method 3): $R_t$=0.252 min, MS (ESIpos) m/z=368.9 $[M+H]^+$. $^1H$ NMR (400 MHZ, DMSO-$d_6$) δ=12.70 (s, 1H), 8.52 (s, 1H), 8.48 (dd, J=0.8, 4.0 Hz, 1H), 7.95 (d, J=8.0 Hz, 1H), 7.90-7.79 (m, 2H), 7.27 (ddd, J=1.2, 4.7, 7.6 Hz, 1H), 6.71-6.30 (m, 3H), 6.01 (s, 2H), 4.89 (dt, J=3.6, 15.2 Hz, 2H).

Intermediate 18

2-(1-methyl-1H-pyrazol-4-yl)acetic acid

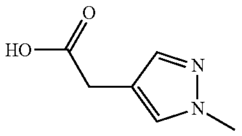

To a stirred solution of 2-(1-methylpyrazol-4-yl) acetonitrile (100.0 mg, 0.825 mmol, CAS-RN: [754159-15-4]) in water (3 mL) was added NaOH (0.330 g, 8.25 mmol, CAS-RN:[1310-73-2]). The mixture was stirred at 100° C. for 12 h. An aqueous solution of HCl (2.5 M) was added to adjust the solution to pH 3. The resulting mixture was extracted with $CH_2Cl_2$ (3×5 mL). The combined organic phase was washed with brine (3×5 mL), dried (sodium sulfate), filtered, and the solvent was removed in vacuo. The resulting residue was triturated with i-PrOH (10 mL) to give 100.0 mg of the title compound as a white solid, which was used with no further purification. $^1H$ NMR (400 MHz, DMSO-d6) δ[ppm]=7.59 (s, 1H), 7.34 (s, 1H), 3.80 (s, 3H), 3.39 (s, 2H).

Intermediate 19 ethyl 2-quinoxalin-2-ylacetate

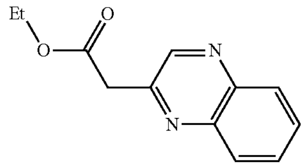 [SMILES: CCOC(=O)Cc1cnc2ccccc2n1]

To a stirred solution of 1,2-phenylenediamine (5.00 g, 46.2 mmol, CAS-RN:[95-54-5]) in MeOH (100 mL) was added ethyl 4-chloroacetoacetate (5.86 g, 35.6 mmol, CAS-RN:[638-07-3]). The mixture was stirred at 40° C. for 12 h. The solvent was removed in vacuo. The resulting residue was diluted with $CH_2Cl_2$ (15 mL) and water (10 mL) and extracted with $CH_2Cl_2$ (20 mL×3). The combined organic phase was washed with brine (20 mL×3), dried (sodium sulfate), filtered, and the solvent removed in vacuo. Silica gel chromatography (Teledyne ISCO®; 80 g SepaFlash® Silica Flash Column, Gradient: Ethyl acetate/Petroleum ether 0-100%) gave 0.70 g (6.2% yield) of the title compound as a yellow oil.

LCMS (method 3): $R_t$=0.45 min., MS (ESIpos): m/z=217.3 $[M+H]^+$

Intermediate 20

2-quinoxalin-2-ylacetic acid

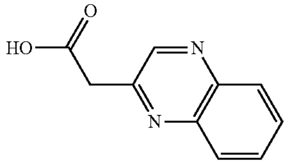 [SMILES: O=C(O)Cc1cnc2ccccc2n1]

To a stirred solution of ethyl 2-quinoxalin-2-ylacetate (300 mg, 1.39 mmol, see Intermediate 19) in a mixture of MeOH (12 mL) and $H_2O$ (1.5 mL) was added KOH (90.0 mg, 1.60 mmol, CAS-RN: [1310-58-3]). The mixture was stirred at 25° C. for 2 h. The MeOH was removed in vacuo, then $H_2O$ (2 mL) was added and the resulting mixture was extracted with ethyl acetate (5 mL×2). The aqueous phase was adjusted to pH 6 by the addition of 0.2 M aqueous HCl, and the resulting mixture was extracted with ethyl acetate (5 mL×3). The combined aqueous phase was lyophilized. Preparative-HPLC (column: Phenomenex Luna C18 75*30 mm*3 um; Gradient: [water (modified with 10 mM $NH_4$—$HCO_3$)-MeCN] 0%-15% over 10 min) followed by lyophilization gave 80 mg (24.5% yield, 80% purity) of the title compound as a red solid. $^1H$ NMR (400 MHZ, DMSO-d6) δ[ppm]=9.20-8.69 (m, 1H), 8.29-7.56 (m, 3H), 3.81-3.58 (m, 2H).

Intermediate 21 methyl 4,4-difluoro-2-(1-methylpyrazol-4-yl)butanoate

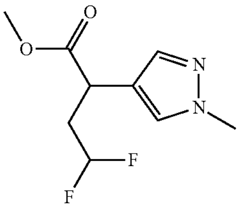

A stirred solution of methyl 1-methyl-1H-pyrazole-4-acetate (300 mg, 1.40 mmol, HOAc salt, CAS-RN: [1248548-23-3]) in anhydrous THF (3.0 mL) under an inert $N_2$ atmosphere was cooled to −78° C. A solution of lithium diisopropylamide in THF (2 M, 1.95 mL, CAS-RN:[4111-54-0]) was added under $N_2$, and the resulting mixture was stirred for 0.5 h at −78° C. A solution of 2,2-difluoroethyl trifluoromethanesulfonate (625 mg, 2.92 mmol, CAS-RN: [74427-22-8]) in THF (1.2 mL) was added dropwise. The mixture was stirred and allowed to warm from −78° C.-25° C. over 12 h. A saturated aqueous solution of $NH_4Cl$ (10 mL) was added, and the mixture was extracted with ethyl acetate (12 mL×3). The combined organic phase was washed with brine (8 mL×3), dried (sodium sulfate), filtered, and the solvent removed in vacuo. Preparative-HPLC (column: Phenomenex Luna C18 150*25 mm*10 um; Gradient: [water (modified with 0.225% formic acid)-MeCN] 17%-47% over 10 min) followed by lyophilization gave 70.0 mg (22.9% yield) of the title compound as a brown oil. $^1H$ NMR (400 MHZ, $CDCl_3$) δ [ppm]=7.43 (s, 1H), 7.34 (s, 1H), 5.93 (t, J=4.8 Hz, 1H), 5.79 (t, J=4.4 Hz, 1H), 5.64 (t, J=4.8 Hz, 1H), 3.90 (s, 3H), 3.80 (t, J=7.6 Hz, 1H), 3.72 (s, 3H), 2.65-2.48 (m, 1H), 2.32-2.17 (m, 1H).

Intermediate 22

4,4-difluoro-2-(1-methylpyrazol-4-yl)butanoic acid

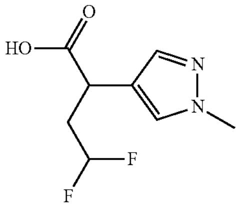

A stirred solution of methyl 4,4-difluoro-2-(1-methylpyrazol-4-yl)butanoate (70.0 mg, 0.321 mmol, see intermediate 21) in a mixture of THF (1.0 mL) and $H_2O$ (0.20 mL) was cooled to 0° C. LiOH·$H_2O$ (26.9 mg, 0.642 mmol, CAS-RN:[1310-66-3]) was added at 0° C. The resulting mixture was stirred at 0° C. for 1 h. The solution was adjusted to pH 3~4 by the addition of a 2 M aqueous solution of HCl. Water (3.0 mL) was added, and the mixture was extracted with ethyl acetate (5.0 mL×10), the combined organic phase was dried (sodium sulfate), filtered, and the solvent removed in vacuo to give 60.0 mg of the title compound as a yellow solid. Used without further purification. LCMS (Method 3): $R_t$=0.624 min.; MS (ESIpos): m/z=205.1 $[M+H]^+$.

Intermediate 23

2-(2-methyloxazol-5-yl)acetic acid

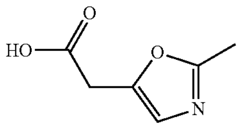

A stirred solution of methyl 2-(2-methyloxazol-5-yl)acetate (120 mg, 0.773 mmol, CAS-RN: [1276083-60-3]) in a mixture of THF (3.0 mL) and $H_2O$ (0.6 mL) was cooled to 0° C. LiOH·$H_2O$ (64.9 mg, 1.55 mmol, CAS-RN:[1310-65-2]) was added at 0° C. The resulting mixture was stirred at 0° C. for 1 h. The reaction mixture was adjusted to pH 3 by the addition of a 2 M aqueous solution of HCl. Water (3.0 mL) was added, and the mixture was extracted with ethyl acetate (5 mL×3). The combined organic phase was washed with brine (2 mL×3), dried (sodium sulfate), filtered, and the solvent removed in vacuo to give 60.0 mg (54.9% yield) of the title compound as a yellow solid, which was used without further purification. $^1$H NMR (400 MHZ, DMSO-d6) δ[ppm]=12.97-12.22 (m, 1H), 6.83 (s, 1H), 3.70 (s, 2H), 2.36 (s, 3H).

Intermediate 26 ethyl 4,4-difluoro-2-(2-methylthiazol-4-yl)butanoate

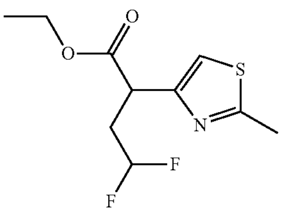 [SMILES: CCOC(=O)C(CC(F)F)c1csc(C)n1]

Ethyl 2-(2-methylthiazol-4-yl)acetate (500 mg, 2.70 mmol, CAS-RN:[37128-24-8]) and 2,2-difluoroethyl trifluoromethanesulfonate (635 mg, 2.97 mmol, CAS-RN: [74427-22-8]) were dissolved in THF (5.0 mL) and cooled to −70° C. A 1 M solution of potassium tert-butoxide in THF (1 M, 2.70 mL, CAS-RN:[865-47-4]) was added at −70° C., and the resulting reaction mixture was stirred at −70° C. for 0.5 h. The reaction mixture was poured into water (50 mL), and the resulting mixture was extracted with ethyl acetate (50 mL×2). The combined organic phase was washed with brine (45 mL×2), dried (sodium sulfate), filtered, and the solvent removed in vacuo. Preparative-HPLC (column: Phenomenex Luna C18 150×25 mm×10 um; Gradient: [water (modified with 0.225% formic acid)-MeCN] 28%-58% over 10.5 min) followed by lyophilization to give 120 mg (17.8% yield) of the title compound as a colorless oil. $^1$H NMR (400 MHZ, DMSO-d6) δ 8.38 (s, 1H), 7.27 (s, 1H), 6.13 (d, J=4.4 Hz, 1H), 4.22 (t, J=7.2 Hz, 1H), 3.69 (s, 3H), 2.79-2.69 (m, 2H).

Intermediate 27

4,4-difluoro-2-(2-methylthiazol-4-yl)butanoic acid

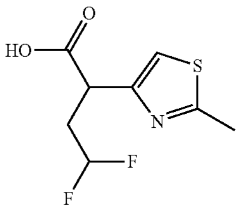

To a stirred solution ethyl 4,4-difluoro-2-(2-methylthiazol-4-yl)butanoate (60 mg, 241 μmol, see Intermediate 26) in a mixture of MeOH (1.0 mL) and THF (1.0 mL) was added LiOH·$H_2O$ (20.2 mg, 481 μmol, CAS-RN:[1310-65-2]) in water (1 mL) at 25° C. The resulting mixture was stirred at 25° C. for 1 h. The reaction mixture was adjusted to pH 5 by the addition of a 1 M aqueous solution of HCl. The resulting mixture was extracted with ethyl acetate (35 mL×2), and the combined organic phase was dried (sodium sulfate), filtered, and the solvent removed in vacuo to give 50 mg of the title compound as a yellow oil. Used without further purification. $^1$H NMR (400 MHZ, DMSO-d6) δ 7.35 (s, 1H), 6.02 (tt, J=4.8, 56 Hz, 1H), 3.92 (t, J=7.2 Hz, 1H), 2.62 (s, 3H), 2.33-2.25 (m, 2H).

Intermediate 30

2-oxazol-5-ylacetate

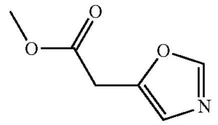

To a stirred solution of 2-oxazol-5-ylacetic acid (500 mg, 3.93 mmol, CAS-RN:[1083337-90-9]) in MeOH (15 mL) was added $H_2SO_4$ (77.2 mg, 786 μmol, CAS-RN:[7664-93-9]). The resulting mixture was stirred at 60° C. for 12 h. The mixture was poured into a w/w 1:1 aqueous solution of $NH_4Cl$ (20 mL). The resulting mixture was extracted with ethyl acetate (20 mL×2). The combined organic phase was washed with brine (20 mL×2), dried (sodium sulfate), filtered, and the solvent removed in vacuo to give 500 mg (90.1% yield) of the title compound as a colorless oil. Used without further purification. $^1$H NMR (400 MHZ, DMSO-d6) δ 8.30 (s, 1H), 7.04 (s, 1H), 3.91 (s, 2H), 3.65 (s, 3H).

Intermediate 31

2-(2,2-difluoroethyl)-4,4-difluoro-2-oxazol-5-yl-butanoate

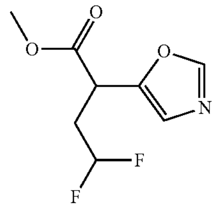

Methyl 2-(oxazol-5-yl)acetate (250 mg, 1.77 mmol, see Intermediate 30) and 2,2-difluoroethyl trifluoromethanesulfonate (417 mg, 1.95 mmol, CAS-RN:[74427-22-8]) were dissolved in THF (3 mL) and cooled to −70° C. A 1 M solution of potassium tert-butoxide in THF (1 M, 2.13 mL, CAS-RN:[865-47-4]) was added dropwise at −70° C. under $N_2$, and the resulting mixture was stirred at −70° C. for 1 h. The mixture was poured into a 1:1 w/w aqueous solution of $NH_4Cl$ (20 mL). The resulting mixture was extracted with ethyl acetate (20 mL×2). The combined organic phase was washed with brine (20 mL×2), dried (sodium sulfate), filtered, and the solvent removed in vacuo. Silica gel chromatography (Gradient: DCM/MeOH 100/1-10/1) followed by removal of the solvent gave 200 mg (39.8% yield) of the title compound as a yellow oil. 1H NMR (400 MHZ, DMSO-d6) δ 8.38 (s, 1H), 7.27 (s, 1H), 6.13 (d, J=4.4 Hz, 1H), 4.22 (t, J=7.2 Hz, 1H), 3.69 (s, 3H), 2.79-2.69 (m, 2H).

Intermediate 32

4,4-difluoro-2-oxazol-5-yl-butanoic acid

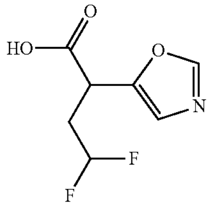 [SMILES: O=C(O)C(CC(F)F)c1cnco1]

To a stirred solution of methyl 4,4-difluoro-2-(oxazol-5-yl)butanoate (200 mg, 975 μmol, see Intermediate 31) in a mixture of THF (2.0 mL) and MeOH (1.0 mL) was added a solution of $LiOH{\cdot}H_2O$ (81.8 mg, 1.95 mmol, CAS-RN: [1310-65-2]) in water (1.0 mL). The resulting mixture was stirred at 25° C. for 1 h. The reaction mixture was adjusted to pH 6-7 by the addition of a 1 M aqueous solution of HCl, followed by removal of the solvent in vacuo to give 160 mg of the title compound as a brown oil. Used without further purification.

Intermediate 35 methyl 2-[6-[[(E)-hydroxyiminomethyl]amino]-3-pyridyl]acetate

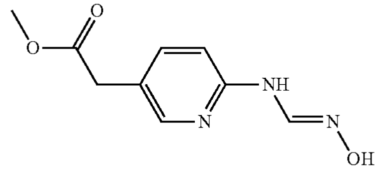

To a stirred solution of methyl 6-amino-3-pyridineacetate (425 mg, 2.56 mmol, CAS-RN: [174891-02-2]) in isopropanol (25.0 mL) was added N,N-dimethylformamide dimethyl acetal (0.85 mL, 6.39 mmol, CAS-RN:[4637-24-5]). The resulting mixture was stirred at reflux overnight. The reaction was incomplete, and N,N-dimethylformamide dimethyl acetal (0.85 mL, 6.39 mmol, CAS-RN:[4637-24-5]) was added a second time. The mixture was stirred at reflux overnight. The reaction mixture was concentrated in vacuo. The mixture was taken up in DCM to form a suspension, which was filtered and then the precipitate was washed 2 times with DCM, to provide 1.00 g (1.43 mmol, 30% purity, 56% yield) of the title compound in low purity. The filtrate contained the title compound, which was subjected to silica gel chromatography (column: Redi Sep Rf 40 g Gold, Gradient: hexanes/ethyl acetate 0%-100% over 20 column volumes) and the solvent removed in vacuo to provide 100 mg (0.430 mmol, 90% purity, 17% yield) of the title compound. LCMS (Method 4)=$R_t$=1.00 min.; MS (ESIpos): m/z=210.14 $[M+H]^+$. 1H NMR (400 MHZ, $CDCl_3$) δ [ppm] 8.12 (dd, J=2.3, 0.8 Hz, 1H), 7.97 (s, 1H), 7.56 (dd, J=8.4, 2.3 Hz, 1H), 6.67 (dd, J=8.4, 0.8 Hz, 1H), 3.71 (s, 3H), 3.56 (s, 2H).

Intermediate 36 methyl 2-([1,2,4]triazolo[1,5-a]pyridin-6-yl)acetate

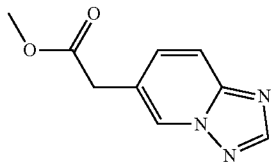

To a stirred solution of methyl 2-[6-[[(E)-hydroxyiminomethyl]amino]-3-pyridyl]acetate (100 mg, 0.143 mmol, see Intermediate 35) in tetrahydrofuran (2.00 mL) was added trifluoroacetic anhydride (0.04 mL, 0.287 mmol, CAS-RN: [407-25-0]) was added to the reaction mixture. The reaction was stirred at 25° C. for one week. A half saturated aqueous solution of sodium carbonate (10 mL) was added, and the mixture was extracted with ethyl acetate (3×15 mL). The combined organic phase was dried (magnesium sulfate), filtered, and the solvent removed in vacuo. Preparative-HPLC (column: Waters xBridge prep C18 5 μm OBD, Size: 19×250 mm, gradient: water/acetonitrile (both modified with 0.1% formic acid) 29%-47% over 18 min) followed by lyophilization to provide 24 mg (0.126 mmol, 26% yield) of the title compound as a yellow solid. LCMS (Method 4): $R_t$=1.03 min.; MS (ESIpos): m/z=192.12 $[M+H]^+$. $^1$H NMR (400 MHZ, MeOD-d4) δ [ppm] 8.78 (s, 1H), 8.40 (s, 1H), 7.74 (d, J=9.4 Hz, 1H), 7.66 (d, J=8.7 Hz, 1H), 3.84 (s, 2H), 3.73 (s, 3H).

Intermediate 37

2-([1,2,4]triazolo[1,5-a]pyridin-6-yl)acetic acid

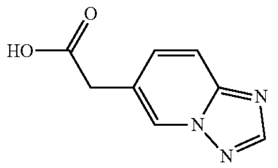 [SMILES: O=C(O)Cc1ccc2ncnn2c1]

To a stirred solution of methyl 2-([1,2,4]triazolo[1,5-a]pyridin-6-yl)acetate (42 mg, 0.220 mmol, see Intermediate 36) in ethanol (2.2 mL) was added a 2 N solution of NaOH in water (0.44 mL, 0.879 mmol, CAS-RN:[1310-73-2]). The mixture was stirred at 60° C. for 15 h. The reaction mixture was concentrated in vacuo, and then adjusted to pH 3 with a 1 N aqueous solution of HCl. The resulting mixture was extracted with ethyl acetate (3×10 mL). The combined organic phase was dried (magnesium sulfate), filtered, and the solvent removed in vacuo. Silica gel chromatography (column: Redi Sep Rf 12 g Gold, gradient: hexanes/ethyl acetate 0%-100% over 45 column volumes), followed by solvent removal in vacuo to give 35 mg (0.198 mmol, 90% yield) of the title compound as a viscous yellow liquid.

LCMS (Method 4): $R_t$=0.72 min.; MS (ESIpos): m/z=178.12 $[M+H]^+$ $^1$H NMR (400 MHZ, MeOD) δ 8.75 (d, J=1.5 Hz, 1H), 8.38 (s, 1H), 7.77-7.71 (m, 1H), 7.68 (dd, J=9.2, 1.7 Hz, 1H), 3.79 (s, 2H).

Compound Synthesis

Example 1

2-imidazo[1,2-a]pyridin-3-yl-N-[4-[3-(2-pyridyl)-1H-pyrrolo[3,2-b]pyridin-2-yl]-2-pyridyl]acetamide

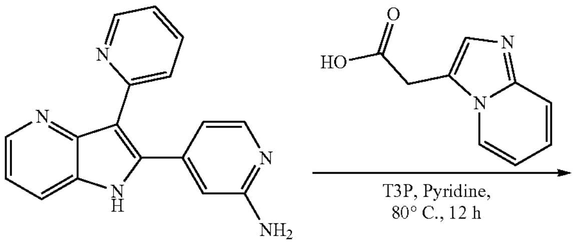

-continued

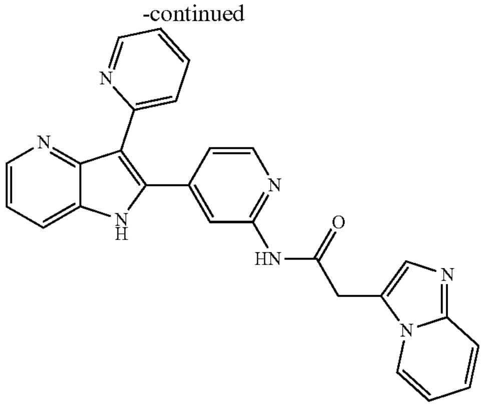

4-[3-(2-pyridyl)-1H-pyrrolo[3,2-b]pyridin-2-yl]pyridin-2-amine (50.0 mg, 0.174 mmol, see Intermediate 8) and 2-imidazo[1,2-a]pyridin-3-ylacetic acid (61.3 mg, 0.348 mmol, CAS-RN: [17745-04-9]) were dissolved in Pyridine (1.0 mL). Propylphosphonic anhydride (0.332 g, 0.522 mmol, CAS-RN [68957-94-8]) was added, and the resulting mixture was stirred at 80° C. for 12 h. A saturated aqueous solution of $NH_4Cl$ (3 mL) was added, and the mixture was extracted with ethyl acetate (3×5 mL). The combined organic layers were washed with brine (3×5 mL), dried (sodium sulfate), filtered, and the solvent was removed in vacuo. Preparative HPLC (column: Phenomenex Gemini 150*25 mm*10 um; Gradient: water (modified with 0.05% $NH_4OH$)-MeCN] 10%-40% over 10 min) followed by lyophilization gave 26.3 mg (34% yield, 100% purity) of the title compound as a brown solid. LCMS (Method 3): $R_t$=0.71 min; MS (ESIpos): m/z=446.4 $[M+H]^+$. $^1$H NMR (400 MHz, DMSO-d6) δ[ppm]=12.04 (s, 1H), 10.93 (s, 1H), 8.44-8.39 (m, 3H), 8.32-8.29 (m, 2H), 8.10 (d, J=8.0 Hz, 1H), 7.86-7.82 (m, 2H), 7.56 (d, J=9.2 Hz, 1H), 7.50 (s, 1H), 7.26-7.20 (m, 3H), 7.17-7.14 (m, 1H), 6.95 (dt, J=0.8, 6.8 Hz, 1H), 4.19 (s, 2H).

Example 2

2-(1-methylpyrazol-4-yl)-N-[4-[3-(2-pyridyl)-1H-pyrrolo[3,2-b]pyridin-2-yl]-2-pyridyl]acetamide

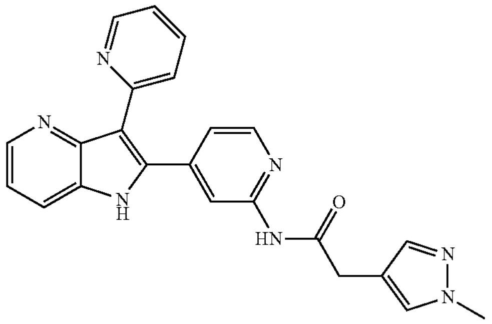 [SMILES: Cn1cc(CC(=O)Nc2cc(-c3[nH]c4cccnc4c3-c3ccccn3)ccn2)cn1]

4-[3-(2-pyridyl)-1H-pyrrolo[3,2-b]pyridin-2-yl]pyridin-2-amine (50.0 mg, 0.174 mmol, see intermediate 8) and 2-(1-methylpyrazol-4-yl)acetic acid (48.7 mg, 0.348 mmol, see intermediate 18) were dissolved in Pyridine (1.0 mL). Propylphosphonic anhydride (0.332 mg, 0.522 mmol, CAS-RN:[17745-04-9]) was added, and the resulting mixture was stirred at 100° C. for 12 h. The mixture was concentrated under reduced pressure to give a residue. Preparative-HPLC (column: Phenomenex Luna C18 150*25 mm*10 um; Gradient: [water (modified with 0.225% formic acid)-MeCN] 3%-33% over 11.5 min) followed by lyophilization gave 30.5 mg (42.9% yield, 100% purity) of the title compound as a brown oil. LCMS (method 3): $R_t$=0.88 min; MS (ESIpos): m/z=410.0 $[M+H]^+$. $^1$H NMR (400 MHZ, DMSO-d6) δ[ppm]=12.51-12.19 (m, 1H), 10.69 (s, 1H), 8.50 (d, J=4.0 Hz, 2H), 8.38-8.28 (m, 2H), 8.13 (s, 1H), 8.00 (d, J=7.2 Hz, 2H), 7.88 (dt, J=1.6, 7.6 Hz, 1H), 7.57 (s, 1H), 7.39-7.26 (m, 3H), 7.19-7.14 (m, 1H), 3.79 (s, 3H), 3.53 (s, 2H).

Example 3

2-(2-methylthiazol-4-yl)-N-[4-[3-(2-pyridyl)-1H-pyrrolo[3,2-b]pyridin-2-yl]-2-pyridyl]acetamide

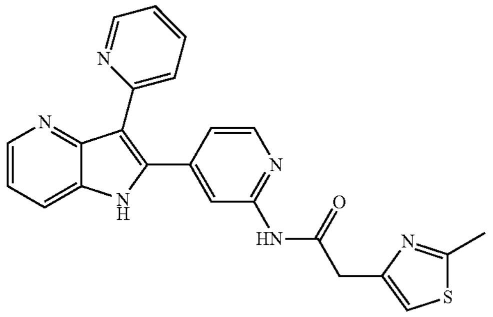 [SMILES: Cc1nc(CC(=O)Nc2cc(-c3[nH]c4cccnc4c3-c3ccccn3)ccn2)cs1]

4-[3-(2-pyridyl)-1H-pyrrolo[3,2-b]pyridin-2-yl]pyridin-2-amine (40.0 mg, 0.139 mmol, see intermediate 8) and 2-(2-methylthiazol-4-yl)acetic acid (21.8 mg, 0.139 mmol, CAS-RN:[13797-62-1]) were dissolved in Pyridine (1.0 mL). Propylphosphonic anhydride (265 mg, 417 μmol, CAS-RN [17745-04-9]) was added, and the resulting mixture was stirred at 25° C. for 12 h. The reaction mixture was concentrated under reduced pressure to give a residue. Preparative-HPLC (column: Waters xBridge 150*25 mm 10 um; Gradient: [water (modified with 10 mM $NH_4$—$HCO_3$)-MeCN] 14%-44% over 11 min) followed by lyophilization gave 13.4 mg (22.4% yield, 99% purity) of the title compound as a brown gum.

LCMS (method 3): $R_t$=0.95 min; MS (ESIpos): m/z=426.9 $[M+H]^+$. $^1$H NMR (400 MHZ, DMSO-d6) δ[ppm]=12.09 (s, 1H), 10.71 (s, 1H), 8.44 (ddd, J=1.2, 4.8, 7.6 Hz, 2H), 8.36 (s, 1H), 8.29 (d, J=5.2 Hz, 1H), 8.14 (d, J=8.0 Hz, 1H), 8.17-8.09 (m, 1H), 7.89-7.82 (m, 2H), 7.29-7.21 (m, 3H), 7.14 (dd, J=1.6, 5.2 Hz, 1H), 3.85 (s, 2H), 2.62 (s, 3H).

Example 4

2-(oxazol-5-yl)-N-(4-(7-(pyridin-2-yl)-5H-pyrrolo[2,3-b]pyrazin-6-yl)pyridin-2-yl)acetamide

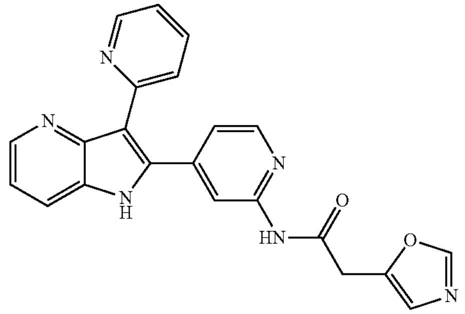 [SMILES: O=C(Cc1cnco1)Nc1cc(-c2[nH]c3cccnc3c2-c2ccccn2)ccn1]

4-[3-(2-pyridyl)-1H-pyrrolo[3,2-b]pyridin-2-yl]pyridin-2-amine (40.0 mg, 139 μmol, see Intermediate 8) and 5-oxazoleacetic acid (26.5 mg, 208 μmol, CAS-RN: [1083337-90-9]) were dissolved in in Pyridine (1.0 mL). A 50 weight % solution of propylphosphonic anhydride in DMF (133 mg, 417 μmol, CAS-RN:[17745-04-9]) was added, and the resulting mixture was stirred at 25° C. for 12 h. The reaction mixture was concentrated under reduced pressure to give a residue. Preparative-HPLC (column: Phenomenex luna C18 150*25 mm*10 um; Gradient: [water (modified with 0.225% formic acid)-MeCN] 1%-30% over 11.5 min) followed by a second preparative-HPLC (column: Phenomenex Luna C18 75*30 mm*3 um; Gradient: [water (modified with 10 mM $NH_4$—$HCO_3$)-MeCN] 3%-33% over 10 min) followed by lyophilization gave 21 mg (38% yield, 100% purity) of the title compound as a white solid. LCMS (method 3): $R_t$=0.86 min; MS (ESIpos): m/z=397.0 $[M+H]^+$. $^1$H NMR (400 MHZ, DMSO-d6) δ[ppm]=12.09 (s, 1H), 10.87 (s, 1H), 8.49-8.41 (m, 2H), 8.35-8.25 (m, 3H), 8.15 (d, J=7.6 Hz, 1H), 7.90-7.84 (m, 2H), 7.29-7.23 (m, 2H), 7.18 (dd, J=1.2, 5.2 Hz, 1H), 7.05 (s, 1H), 3.95 (s, 2H).

Example 5

2-(1-methylimidazol-4-yl)-N-[4-[3-(2-pyridyl)-1H-pyrrolo[3,2-b]pyridin-2-yl]-2-pyridyl]acetamide

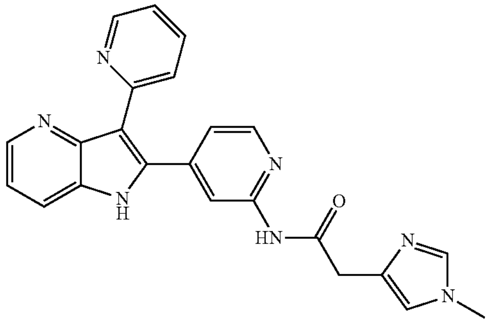 [SMILES: Cn1cnc(CC(=O)Nc2cc(-c3[nH]c4cccnc4c3-c3ccccn3)ccn2)c1]

4-[3-(2-pyridyl)-1H-pyrrolo[3,2-b]pyridin-2-yl]pyridin-2-amine (50.0 mg, 0.174 mmol, see Intermediate 8) and 2-(1-methylimidazol-4-yl)acetic acid (60.9 mg, 0.348 mmol, CAS-RN: [2625-49-2]) were dissolved in Pyridine (1.0 mL).

Propylphosphonic anhydride (0.332 g, 0.522 mmol, CAS-RN:[17745-04-9]) was added, and the resulting mixture was stirred at 60° C. for 2 h. The reaction mixture was concentrated under reduced pressure to give a residue. Preparative-HPLC (column: Phenomenex Gemini 150*25 mm*10 um; Gradient: [water (modified with 0.05% $NH_3$—$H_2O$)-MeCN] 10%-40% over 10 min) followed by lyophilization gave 11.6 mg (14.9% yield, 92% purity) of the title compound as a brown solid.

LCMS (method 3): $R_t$=0.66 min, m/z (ESIpos): m/z=410.0 $[M+H]^+$. $^1$H NMR (400 MHZ, DMSO-d6) δ[ppm]=12.09 (s, 1H), 10.57 (s, 1H), 8.47-8.41 (m, 2H), 8.34 (s, 1H), 8.27 (d, J=5.2 Hz, 1H), 8.14 (d, J=8.0 Hz, 1H), 7.89-7.84 (m, 2H), 7.55 (s, 1H), 7.28-7.22 (m, 2H), 7.14 (dd, J=1.6, 5.2 Hz, 1H), 6.99 (s, 1H), 3.62 (s, 3H), 3.59 (s, 2H).

Example 6

N-[4-[3-(2-pyridyl)-1H-pyrrolo[3,2-b]pyridin-2-yl]-2-pyridyl]-2-quinoxalin-2-yl-acetamide

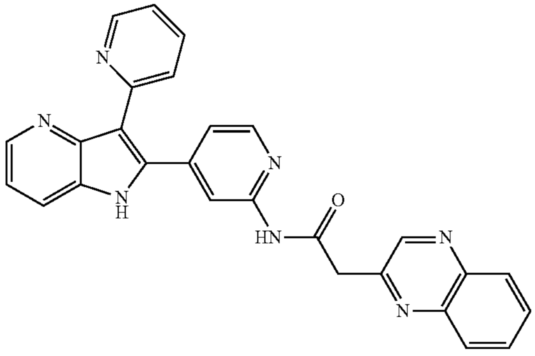 [SMILES: O=C(Cc1cnc2ccccc2n1)Nc1cc(-c2[nH]c3cccnc3c2-c2ccccn2)ccn1]

4-[3-(2-pyridyl)-1H-pyrrolo[3,2-b]pyridin-2-yl]pyridin-2-amine (40.0 mg, 0.14 mmol, see Intermediate 8) and 2-quinoxalin-2-ylacetic acid (26.2 mg, 0.14 mmol, see intermediate 20) were dissolved in MeCN (0.50 mL). Chloro-N,N,N',N'-tetramethylformamidinium hexafluorophosphate (78.1 mg, 0.28 mmol, CAS-RN:[207915-99-9]) and 1-methylimidazole (40.0 mg, 0.48 mmol, CAS-RN:[616-47-7]) were added, and the resulting mixture was stirred at 40° C. for 2 h. The reaction mixture was concentrated under reduced pressure. Preparative-HPLC (column: Phenomenex Gemini 150*25 mm*10 um; Gradient: [water (modified with 0.05% $NH_3$—$H_2O$)-MeCN] 17%-47% over 10 min) followed by lyophilization gave 5.9 mg (8.8% yield, 96% purity) of the title compound as a yellow gum. LCMS (method 3): $R_t$=1.09 min; MS (ESIpos): m/z=458.0 $[M+H]^+$. $^1$H NMR (400 MHZ, DMSO-d6) δ[ppm]=13.85 (s, 1H), 7.82 (d, J=7.6 Hz, 1H), 7.70 (d, J=7.2 Hz, 1H), 7.57-7.44 (m, 6H), 7.44-7.36 (m, 1H), 5.39 (s, 2H), 3.86-3.75 (m, 1H), 3.64-3.46 (m, 3H), 3.26-2.85 (m, 2H), 1.48 (s, 9H)

Example 7

2-(1,3-benzoxazol-2-yl)-N-[4-[3-(2-pyridyl)-1H-pyrrolo[3,2-b]pyridin-2-yl]-2-pyridyl]acetamide

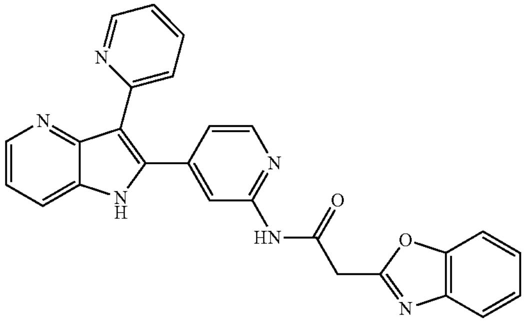 [SMILES: O=C(Cc1nc2ccccc2o1)Nc1cc(-c2[nH]c3cccnc3c2-c2ccccn2)ccn1]

4-[3-(2-pyridyl)-1H-pyrrolo[3,2-b]pyridin-2-yl]pyridin-2-amine (50.0 mg, 0.174 mmol, see Intermediate 8) and benzooxazol-2-yl-acetic acid (46.2 mg, 0.261 mmol, CAS-RN:[78756-98-6]) were dissolved in Pyridine (1.0 mL). Propylphosphonic anhydride (0.332 mg, 0.522 mmol, CAS-RN:[68957-94-8]) was added, and the resulting mixture was stirred at 25° C. for 12 h. Water (5.0 mL) was added and the mixture was extracted with ethyl acetate (8 mL×3). The combined organic phase was washed with brine (2 mL×3), dried (sodium sulfate), filtered, and the solvent removed in vacuo. Preparative-HPLC (column: Phenomenex Gemini 150×25 mm×10 um; Gradient: [water (modified with 0.05% $NH_3$—$H_2O$)-MeCN] 20%-50% over 10 min) followed by preparative-HPLC (column: Phenomenex Gemini 150×25 mm×10 um; Gradient: [water (modified with 10 mM $NH_4$—$HCO_3$)-MeCN] 20%-50% over 10 min) followed by lyophilization gave 1.44 mg (1.85% yield, 100% purity) of the title compound as an off-white solid. LCMS (method 3): $R_t$=1.10 min.; MS (ESIpos): m/z=447.4 $[M+H]^+$. $^1$H NMR (400 MHZ, DMSO-d6) δ[ppm]=12.10 (s, 1H), 11.05 (s, 1H), 8.46-8.41 (m, 2H), 8.33 (d, J=5.2 Hz, 2H), 8.14 (d, J=8.0 Hz, 1H), 7.86 (dd, J=1.6, 8.0 Hz, 2H), 7.75-7.70 (m, 2H), 7.42-7.35 (m, 2H), 7.27-7.19 (m, 3H), 4.26 (s, 2H).

Example 8

N-[4-[3-(2-pyridyl)-1H-pyrrolo[3,2-b]pyridin-2-yl]-2-pyridyl]-2-thiazol-2-yl-acetamide

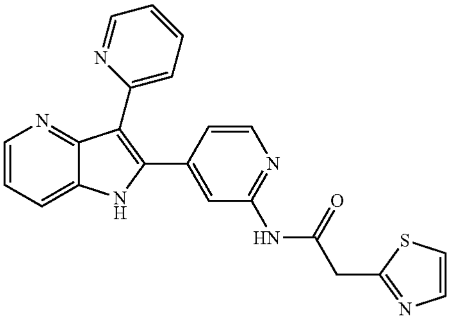 [SMILES: O=C(Cc1nccs1)Nc1cc(-c2[nH]c3cccnc3c2-c2ccccn2)ccn1]

4-[3-(2-pyridyl)-1H-pyrrolo[3,2-b]pyridin-2-yl]pyridin-2-amine (50.0 mg, 0.174 mmol, see Intermediate 8) and 2-thiazoleacetic acid (37.4 mg, 0.261 mmol, CAS-RN: [188937-16-8]) were dissolved in Pyridine (1.0 mL). Propylphosphonic anhydride (332 mg, 0.522 mmol, CAS-RN: [68957-94-8]) was added, and the resulting mixture was stirred at 25° C. for 12 h, then at 40° C. for 4 h. The reaction mixture was concentrated in vacuo. Preparative-HPLC (column: Phenomenex Gemini 150×25 mm×10 um; Gradient: [water (modified with 0.05% $NH_3$—$H_2O$)-MeCN] 13%-43% over 10 min) followed by preparative-HPLC (column: Phenomenex Synergi Polar-RP 100×25 mm×4 um; Gradient: [water (modified with 0.225% formic acid)-MeCN] 5%-35% over 11.5 min), followed by preparative-HPLC (column: Phenomenex Gemini 150×25 mm×10 um; Gradient: [water (modified with 10 mM $NH_4$—$HCO_3$)-MeCN] 12%-42% over 10 min) followed by lyophilization gave 25.0 mg (33.8% yield, 96.9% purity) of the title compound as a light yellow solid. LCMS (method 3): $R_t$=0.90 min.; MS (ESIpos): m/z=413.4 $[M+H]^+$. $^1$H NMR (400 MHZ, DMSO-d6) δ[ppm]=12.10 (s, 1H), 10.95 (s, 1H), 8.46-8.42 (m, 2H), 8.36 (s, 1H), 8.31 (d, J=5.2 Hz, 1H), 8.14 (d, J=8.0 Hz, 1H), 7.87 (d, J=7.2 Hz, 2H), 7.75 (d, J=3.2 Hz, 1H), 7.66 (d, J=3.2 Hz, 1H), 7.28-7.23 (m, 2H), 7.18 (dd, J=1.6, 5.2 Hz, 1H), 4.26 (s, 2H)

Example 9

2-(1,3-dimethylpyrazol-4-yl)-N-[4-[3-(2-pyridyl)-1H-pyrrolo[3,2-b]pyridin-2-yl]-2-pyridyl]acetamide

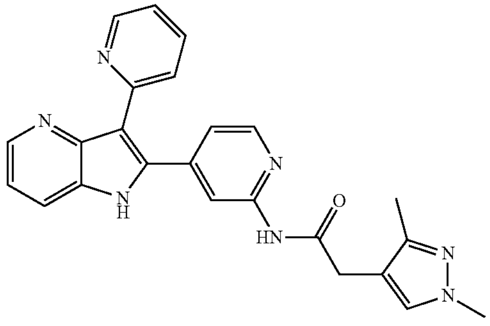 [SMILES: Cc1nn(C)cc1CC(=O)Nc1cc(-c2[nH]c3cccnc3c2-c2ccccn2)ccn1]

4-[3-(2-pyridyl)-1H-pyrrolo[3,2-b]pyridin-2-yl]pyridin-2-amine (150 mg, 0.261 mmol, 50% purity, see Intermediate 8) and 2-(1,3-dimethyl-1H-pyrazol-4-yl)acetic acid (60.4 mg, 0.392 mmol, CAS-RN:[1177342-49-2]) were dissolved in Pyridine (1.5 mL). Propylphosphonic anhydride (498 mg, 0.783 mmol, CAS-RN:[68957-94-8]) was added, and the resulting mixture was stirred at 25° C. for 12 h. The reaction mixture was concentrated in vacuo. Preparative-HPLC (column: Phenomenex Gemini 150×25 mm×10 um; Gradient: [water (modified with 0.05% $NH_3$—$H_2O$)-MeCN] 12%-42% over 10 min) followed by lyophilization gave 54 mg (48.5% yield, 99.3% purity) of the title compound as a light yellow solid.

LCMS (method 3): $R_t$=0.78 min.; MS (ESIpos): m/z=424.2 $[M+H]^+$. $^1$H NMR (400 MHZ, DMSO-d6) δ[ppm]=12.07 (s, 1H), 10.60 (s, 1H), 8.46-8.41 (m, 2H), 8.33 (s, 1H), 8.28 (d, J=5.2 Hz, 1H), 8.13 (d, J=8.0 Hz, 1H), 7.87 (d, J=8.4 Hz, 2H), 7.45 (s, 1H), 7.25 (td, J=4.8, 8.0 Hz, 2H), 7.14 (dd, J=1.2, 5.2 Hz, 1H), 3.71 (s, 3H), 3.47 (s, 2H), 2.09 (s, 3H).

Example 10

2-isoxazol-3-yl-N-[4-[3-(2-pyridyl)-1H-pyrrolo[3,2-b]pyridin-2-yl]-2-pyridyl]acetamide

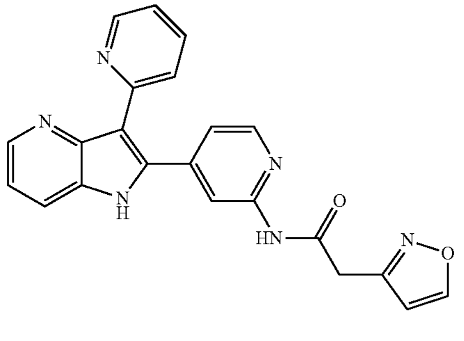 [SMILES: O=C(Cc1ccon1)Nc1cc(-c2[nH]c3cccnc3c2-c2ccccn2)ccn1]

4-[3-(2-pyridyl)-1H-pyrrolo[3,2-b]pyridin-2-yl]pyridin-2-amine (150 mg, 0.261 mmol, 50% purity, see Intermediate 8) and 2-isoxazol-3-ylacetic acid (49.8 mg, 0.392 mmol, CAS-RN: [57612-86-9]) were dissolved in Pyridine (1.5 mL). Propylphosphonic anhydride (498 mg, 0.783 mmol, CAS-RN:[68957-94-8]) was added, and the resulting mixture was stirred at 40° C. for 12 h. The reaction mixture was concentrated in vacuo. Preparative-HPLC (column: Phenomenex Gemini 150×25 mm×10 um; Gradient: [water (modified with 0.05% $NH_3$—$H_2O$)-MeCN] 12%-42% over 10 min) followed by lyophilization gave 44.0 mg (41.8% yield, 98.4% purity) of the title compound as a light yellow solid. LCMS (method 3): $R_t$=0.76 min.; MS (ESIpos): m/z=397.2 $[M+H]^+$. $^1$H NMR (400 MHZ, DMSO-d6) δ[ppm]=12.09 (s, 1H), 10.91 (s, 1H), 8.85 (d, J=1.6 Hz, 1H), 8.47-8.41 (m, 2H), 8.35-8.28 (m, 2H), 8.14 (d, J=8.0 Hz, 1H), 7.89-7.83 (m, 2H), 7.28-7.22 (m, 2H), 7.17 (dd, J=1.6, 5.2 Hz, 1H), 6.56 (d, J=1.6 Hz, 1H), 3.92 (s, 2H).

Example 11

2-(5-methyloxazol-4-yl)-N-[4-[3-(2-pyridyl)-1H-pyrrolo[3,2-b]pyridin-2-yl]-2-pyridyl]acetamide

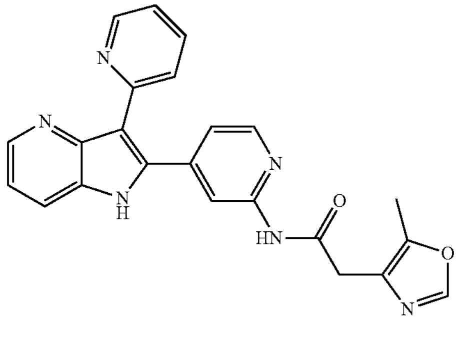 [SMILES: Cc1ocnc1CC(=O)Nc1cc(-c2[nH]c3cccnc3c2-c2ccccn2)ccn1]

4-[3-(2-pyridyl)-1H-pyrrolo[3,2-b]pyridin-2-yl]pyridin-2-amine (150 mg, 0.261 mmol, 50% purity, see Intermediate 8) and 5-methyl-4-oxazoleacetic acid (55.3 mg, 0.392 mmol, CAS-RN: [1507656-31-6]) were dissolved in Pyridine (1.5 mL). Propylphosphonic anhydride (498 mg, 0.783 mmol, CAS-RN:[68957-94-8]) was added, and the resulting mixture was stirred at 40° C. for 12 h. The reaction mixture was concentrated in vacuo. Preparative-HPLC (column: Phenomenex Gemini 150×25 mm×10 um; Gradient: [water (modified with 0.05% $NH_3$—$H_2O$)-MeCN] 12%-42%, 10 min) followed by lyophilization gave 30 mg (27.8% yield, 99.5% purity) of the title compound as a light yellow solid. LCMS (method 3): $R_t$=0.82 min.; MS (ESIpos): m/z=411.1 $[M+H]^+$. $^1$H NMR (400 MHZ, DMSO-d6) δ[ppm]=12.08 (s, 1H), 10.68 (s, 1H), 8.44 (ddd, J=1.2, 4.8, 8.8 Hz, 2H), 8.33 (s, 1H), 8.29 (d, J=5.2 Hz, 1H), 8.14 (t, J=4.0 Hz, 2H), 7.88-7.83 (m, 2H), 7.27-7.22 (m, 2H), 7.15 (dd, J=1.6, 5.2 Hz, 1H), 3.63 (s, 2H), 2.29 (s, 3H).

Example 12

2-(3,5-dimethylisoxazol-4-yl)-N-[4-[3-(2-pyridyl)-1H-pyrrolo[3,2-b]pyridin-2-yl]-2-pyridyl]acetamide

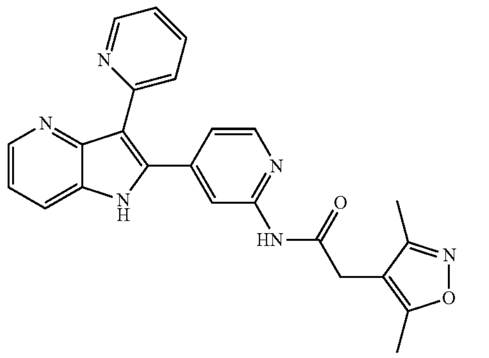 [SMILES: Cc1noc(C)c1CC(=O)Nc1cc(-c2[nH]c3cccnc3c2-c2ccccn2)ccn1]

4-[3-(2-pyridyl)-1H-pyrrolo[3,2-b]pyridin-2-yl]pyridin-2-amine (150 mg, 0.261 mmol, 50% purity, see Intermediate 8) and (3,5-dimethyl-isoxazol-4-yl)-acetic acid (60.8 mg, 0.392 mmol, CAS-RN:[2510-27-2]) were dissolved in Pyridine (1.5 mL). Propylphosphonic anhydride (498 mg, 0.783 mmol, CAS-RN:[68957-94-8]) was added and the resulting mixture was stirred at 40° C. for 12 h. The reaction mixture was concentrated in vacuo. Preparative-HPLC (column: Phenomenex Gemini 150×25 mm×10 um; Gradient: [water (0.05% $NH_3$—$H_2O$)-MeCN] 15%-45% over 10 min) gave 32.0 mg (28.2% yield, 97.5% purity) of the title compound as a yellow solid. LCMS (method 3): $R_t$=0.87 min.; MS (ESIpos): m/z=425.2 $[M+H]^+$. $^1$H NMR (400 MHZ, DMSO-d6) δ[ppm]=12.06 (s, 1H), 10.80 (s, 1H), 8.45-8.40 (m, 2H), 8.32-8.27 (m, 2H), 8.11 (d, J=8.0 Hz, 1H), 7.86 (dd, J=1.2, 8.0 Hz, 2H), 7.27-7.22 (m, 2H), 7.16 (dd, J=1.6, 5.2 Hz, 1H), 3.53 (s, 2H), 2.32 (s, 3H), 2.15 (s, 3H).

Example 13

2-(3-methylisoxazol-5-yl)-N-[4-[3-(2-pyridyl)-1H-pyrrolo[3,2-b]pyridin-2-yl]-2-pyridyl]acetamide

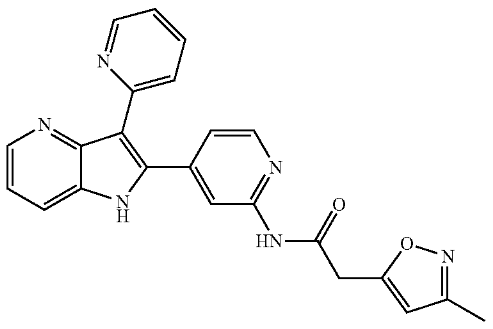 [SMILES: Cc1cc(CC(=O)Nc2cc(-c3[nH]c4cccnc4c3-c3ccccn3)ccn2)on1]

4-[3-(2-pyridyl)-1H-pyrrolo[3,2-b]pyridin-2-yl]pyridin-2-amine (50.0 mg, 0.174 mmol, see Intermediate 8) and 3-methyl-5-isoxazoleacetic acid (36.8 mg, 0.261 mmol, CAS-RN:[19668-85-0]) were dissolved in Pyridine (1.0 mL). Propylphosphonic anhydride (332 mg, 522 μmol, CAS-RN:[68957-94-8) was added, and the resulting mixture was stirred at 40° C. for 12 h. The reaction mixture was concentrated in vacuo. Preparative-HPLC (column: Phenomenex Gemini 150*25 mm*10 um; Gradient: [water (0.05% $NH_3$—$H_2O$)-MeCN] 13%-43% over 10 min) followed by lyophilization gave 24.1 mg (31.8% yield, 94% purity) of the title compound as a yellow solid. LCMS (Method 3): $R_t$=0.90 min; MS (ESIpos): m/z=411.4 $[M+H]^+$. $^1$H NMR (400 MHZ, DMSO-d6) δ[ppm]=12.09 (s, 1H), 10.90 (s, 1H), 8.53-8.49 (m, 1H), 8.44-8.44 (m, 1H), 8.48-8.40 (m, 1H), 8.31 (d, J=4.8 Hz, 2H), 8.21 (s, 1H), 8.14 (d, J=8.0 Hz, 1H), 7.91-7.82 (m, 2H), 7.31-7.21 (m, 2H), 7.20-7.17 (m, 1H), 6.25 (s, 1H), 3.99 (s, 2H), 2.21 (s, 3H).

Example 14

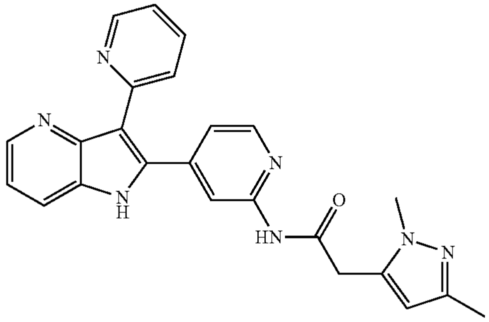 [SMILES: Cc1cc(CC(=O)Nc2cc(-c3[nH]c4cccnc4c3-c3ccccn3)ccn2)n(C)n1]

4-[3-(2-pyridyl)-1H-pyrrolo[3,2-b]pyridin-2-yl]pyridin-2-amine (50.0 mg, 0.174 mmol, see Intermediate 8) and 1,3-dimethyl-1H-pyrazole-5-acetic acid (40.2 mg, 0.261 mmol, CAS-RN: 7-12-1]) were dissolved in Pyridine (1.0 mL). Propylphosphonic anhydride (332 mg, 0.522 μmol, CAS-RN:[68957-94-8]) was added, and the resulting mixture was stirred at 25° C. for 12 h. The reaction mixture was concentrated in vacuo. Preparative-HPLC (column: Phenomenex Gemini 150*25 mm*10 um; Gradient: [water (modified with 0.05% $NH_3$—$H_2O$)-MeCN] 12%-42% over 10 min) followed by lyophilization gave 19.3 mg (25.9% yield, 99% purity) of the title compound as an off-white solid. LCMS (method 3): $R_t$=0.92 min; MS (ESIpos): m/z=424.0 $[M+H]^+$. $^1$H NMR (400 MHZ, DMSO-d6) δ[ppm]=12.08 (s, 1H), 10.79 (s, 1H), 8.49-8.37 (m, 2H), 8.34-8.26 (m, 2H), 8.13 (d, J=8.0 Hz, 1H), 7.89-7.83 (m, 2H), 7.29-7.21 (m, 2H), 7.20-7.14 (m, 1H), 5.92 (s, 1H), 3.81 (s, 2H), 3.68 (s, 3H), 2.08 (s, 3H).

Example 15

2-pyrazolo[1,5-a]pyridin-2-yl-N-[4-[3-(2-pyridyl)-1H-pyrrolo[3,2-b]pyridin-2-yl]-2-pyridyl]acetamide

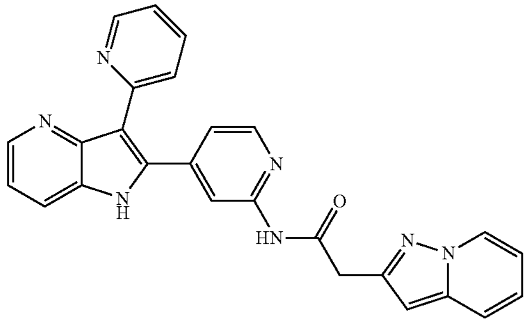 [SMILES: O=C(Cc1cc2ccccn2n1)Nc1cc(-c2[nH]c3cccnc3c2-c2ccccn2)ccn1]

4-[3-(2-pyridyl)-1H-pyrrolo[3,2-b]pyridin-2-yl]pyridin-2-amine (50.0 mg, 0.174 mmol, see Intermediate 8) and 2-pyrazolo[1,5-a]pyridin-2-ylacetic acid (46.0 mg, 0.261 mmol, CAS-RN: [279821-25-8]) were dissolved in Pyridine (1.0 mL). Propylphosphonic anhydride (332 mg, 0.522 mmol, CAS-RN:[68957-94-8]) was added, and the resulting mixture was stirred at 25° C. for 12 h. The reaction mixture was concentrated in vacuo. Preparative-HPLC (column: Phenomenex Gemini 150×25 mm×10 um; Gradient: [water (modified with 0.05% $NH_3$—$H_2O$)-MeCN] 17%-47% over 10 min) followed by lyophilization gave 36 mg (46.4% yield, 100% purity) of the title compound as an off-white solid. LCMS (Method 3): $R_t$=1.10 min.; MS (ESIpos): m/z=446.0 $[M+H]^+$. $^1H$ NMR (400 MHZ, DMSO-d6) δ[ppm]=12.08 (s, 1H), 10.78 (s, 1H), 8.60 (d, J=7.2 Hz, 1H), 8.46-8.40 (m, 2H), 8.35 (s, 1H), 8.30 (d, J=5.2 Hz, 1H), 8.13 (d, J=8.0 Hz, 1H), 7.86 (d, J=7.6 Hz, 2H), 7.62 (d, J=8.8 Hz, 1H), 7.27-7.21 (m, 2H), 7.20-7.14 (m, 2H), 6.85-6.80 (m, 1H), 6.53 (s, 1H), 3.94 (s, 2H).

Example 16

2-(1,5-dimethylpyrazol-3-yl)-N-[4-[3-(2-pyridyl)-1H-pyrrolo[3,2-b]pyridin-2-yl]-2-pyridyl]acetamide

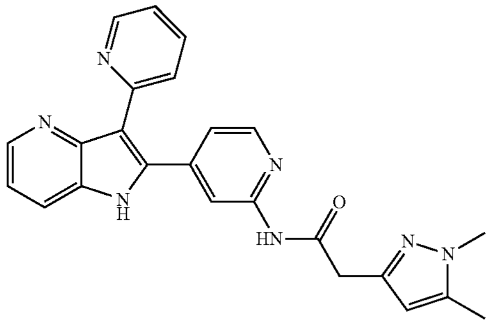 [SMILES: Cc1cc(CC(=O)Nc2cc(-c3[nH]c4cccnc4c3-c3ccccn3)ccn2)nn1C]

4-[3-(2-pyridyl)-1H-pyrrolo[3,2-b]pyridin-2-yl]pyridin-2-amine (50.0 mg, 0.174 mmol, see Intermediate 8) and 2-(1,5-dimethylpyrazol-3-yl)acetic acid (40.2 mg, 0.261 mmol, CAS-Rn: [1185292-77-6]) were dissolved in Pyridine (1.0 mL). Propylphosphonic anhydride (332 mg, 0.522 mmol, CAS-RN:[68957-94-8]) was added, and the resulting mixture was stirred at 25° C. for 12 h. The reaction mixture was concentrated in vacuo. Preparative-HPLC (column: Phenomenex Gemini 150×25 mm×10 um; Gradient: [water (0.05% $NH_3$—$H_2O$)-MeCN] 13%-43% over 10 min) followed by lyophilization gave 44.0 mg (57.9% yield, 97.0% purity) of the title compound as an off-white solid. LCMS (Method 3): $R_t$=0.97 min.; MS (ESIpos): m/z=424.0 $[M+H]^+$. $^1H$ NMR (400 MHZ, DMSO-d6) δ[ppm]=12.12 (s, 1H), 10.57 (s, 1H), 8.47-8.42 (m, 2H), 8.33 (s, 1H), 8.28 (d, J=5.2 Hz, 1H), 8.12 (d, J=8.0 Hz, 1H), 7.89-7.84 (m, 2H), 7.28-7.23 (m, 2H), 7.14 (dd, J=1.6, 5.2 Hz, 1H), 5.94 (s, 1H), 3.65 (s, 3H), 3.60 (s, 2H), 2.20 (s, 3H).

Example 17

N-[4-[3-(2-pyridyl)-1H-pyrrolo[3,2-b]pyridin-2-yl]-2-pyridyl]-2-(1,3,5-trimethylpyrazol-4-yl)acetamide

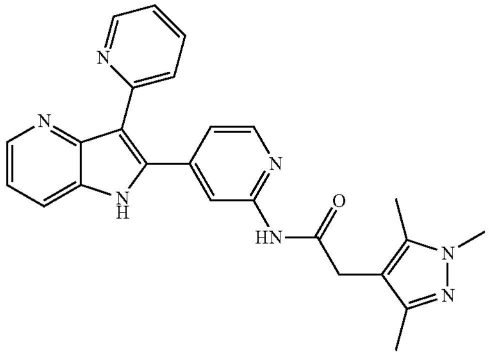 [SMILES: Cc1nn(C)c(C)c1CC(=O)Nc1cc(-c2[nH]c3cccnc3c2-c2ccccn2)ccn1]

4-[3-(2-pyridyl)-1H-pyrrolo[3,2-b]pyridin-2-yl]pyridin-2-amine (50.0 mg, 0.174 mmol, see Intermediate 8) and 2-(1,3,5-trimethyl-1H-pyrazol-4-yl)acetic acid (43.9 mg, 0.261 mmol, CAS-RN: [70598-03-7]) were dissolved in Pyridine (1.0 mL). Propylphosphonic anhydride (332 mg, 0.522 mmol, CAS-RN:[68957-94-8]) was added, and the reaction mixture was stirred at 25° C. for 12 h. The reaction mixture was concentrated in vacuo. Preparative-HPLC (column: Phenomenex Gemini 150×25 mm×10 um; Gradient: [water (0.05% $NH_3$—$H_2O$)-MeCN] 15%-45% over 10 min) followed by lyophilization gave 28.0 mg (36.4% yield, 98.9% purity) of the title compound as a white solid. LCMS (Method 3): $R_t$=0.87 min.; MS (ESIpos): m/z=438.0 $[M+H]^+$. $^1H$ NMR (400 MHZ, DMSO-d6) δ[ppm]=12.06 (s, 1H), 10.56 (s, 1H), 8.46-8.39 (m, 2H), 8.32 (s, 1H), 8.28 (d, J=5.6 Hz, 1H), 8.13 (d, J=8.0 Hz, 1H), 7.88-7.83 (m, 2H), 7.27-7.22 (m, 2H), 7.13 (dd, J=1.6, 5.2 Hz, 1H), 3.61 (s, 3H), 3.45 (s, 2H), 2.16 (s, 3H), 2.06 (s, 3H).

Example 18

2-(2,4-dimethylthiazol-5-yl)-N-[4-[3-(2-pyridyl)-1H-pyrrolo[3,2-b]pyridin-2-yl]-2-pyridyl]acetamide

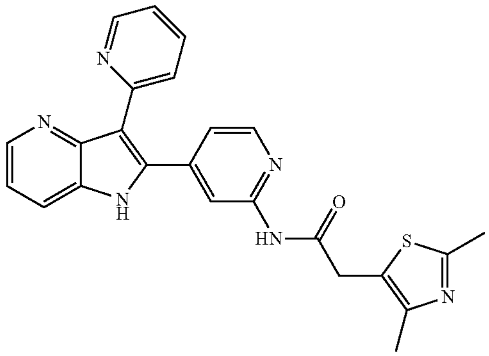 [SMILES: Cc1nc(C)c(CC(=O)Nc2cc(-c3[nH]c4cccnc4c3-c3ccccn3)ccn2)s1]

4-[3-(2-pyridyl)-1H-pyrrolo[3,2-b]pyridin-2-yl]pyridin-2-amine (50.0 mg, 0.174 mmol, see Intermediate 8) and 2-(2,4-dimethylthiazol-5-yl)acetic acid (44.7 mg, 261 μmol, CAS-RN: [34272-65-6]) were dissolved in Pyridine (1.0 mL). Propylphosphonic anhydride (332 mg, 0.522 μmol, CAS-RN:[68957-94-8]) was added, and the reaction mixture was stirred at 25° C. for 12 h. The reaction mixture was concentrated in vacuo. Preparative-HPLC (column: Phenomenex Gemini 150×25 mm×10 um; Gradient: [water (0.05% $NH_3$—$H_2O$)-MeCN] 18%-48% over 10 min) followed by lyophilization gave 40 mg (52.2% yield, 100% purity) of the title compound as a yellow solid. LCMS (Method 3): $R_t$=0.83 min.; MS (ESIpos): m/z=441.4 $[M+H]^+$. $^1H$ NMR (400 MHZ, DMSO-d6) δ[ppm]=12.14 (s, 1H), 10.85 (s, 1H), 8.48-8.41 (m, 2H), 8.35-8.27 (m, 2H), 8.11 (d, J=8.0 Hz, 1H), 7.92-7.83 (m, 2H), 7.30-7.23 (m, 2H), 7.17 (dd, J=1.6, 5.2 Hz, 1H), 3.89 (s, 2H), 2.54 (s, 3H), 2.27 (s, 3H).

Example 19

4,4-difluoro-2-(1-methylpyrazol-4-yl)-N-[4-[3-(2-pyridyl)-1H-pyrrolo[3,2-b]pyridin-2-yl]-2-pyridyl] butanamide

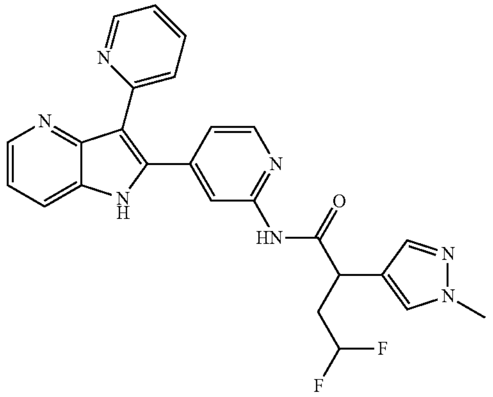 [SMILES: Cn1cc(C(CC(F)F)C(=O)Nc2cc(-c3[nH]c4cccnc4c3-c3ccccn3)ccn2)cn1]

4-[3-(2-pyridyl)-1H-pyrrolo[3,2-b]pyridin-2-yl]pyridin-2-amine (110 mg, 0.191 mmol, 50% purity, see Intermediate 8) and 4,4-difluoro-2-(1-methylpyrazol-4-yl)butanoic acid (58.6 mg, 0.287 mmol, see Intermediate 22) were dissolved in Pyridine (1.2 mL). Propylphosphonic anhydride (365 mg, 0.574 mmol) was added, and the resulting mixture was stirred at 40° C. for 3 h. The reaction mixture was concentrated in vacuo. Preparative-HPLC (column: Phenomenex Gemini 150*25 mm*10 um; Gradient: [water (modified with 0.05% $NH_3$—$H_2O$)-MeCN] 17%-47% over 10 min) followed by lyophilization gave 12.0 mg (13.0% yield, 98.4% purity) of the title compound as an off-white solid. LCMS (Method 3): $R_t$=1.01 min.; MS (ESIpos): m/z=474.0 $[M+H]^+$. $^1H$ NMR (400 MHZ, DMSO-d6) δ[ppm]=12.09 (s, 1H), 10.80 (s, 1H), 8.46 (dd, J=1.2, 4.4 Hz, 1H), 8.40 (d, J=4.0 Hz, 1H), 8.34 (s, 1H), 8.27 (d, J=5.2 Hz, 1H), 8.15 (d, J=8.0 Hz, 1H), 7.89-7.84 (m, 2H), 7.64 (s, 1H), 7.41 (s, 1H), 7.28-7.23 (m, 2H), 7.12 (dd, J=1.2, 5.2 Hz, 1H), 6.14 (t, J=4.4 Hz, 1H), 6.00 (t, J=4.4 Hz, 1H), 5.86 (t, J=4.4 Hz, 1H), 4.08 (dd, J=6.0, 8.8 Hz, 1H), 3.80 (s, 3H), 2.64-2.55 (m, 1H), 2.25-2.14 (m, 1H).

Example 20

N-[4-[3-(2-pyridyl)-1H-pyrrolo[3,2-b]pyridin-2-yl]-2-pyridyl]-2-[1-(2,2,2-trifluoroethyl)pyrazol-3-yl] acetamide

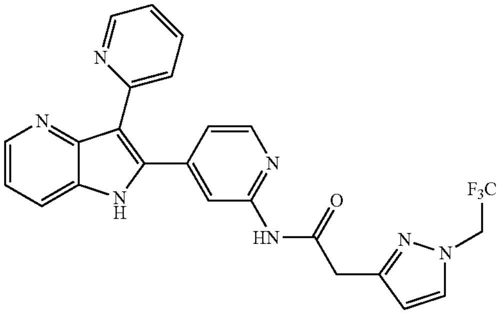 [SMILES: O=C(Cc1ccn(CC(F)(F)F)n1)Nc1cc(-c2[nH]c3cccnc3c2-c2ccccn2)ccn1]

4-[3-(2-pyridyl)-1H-pyrrolo[3,2-b]pyridin-2-yl]pyridin-2-amine (150 mg, 0.261 mmol, 50% purity, see Intermediate 8) and 2-[1-(2,2,2-trifluoroethyl)pyrazol-3-yl]acetic acid (81.5 mg, 0.392 mmol, CAS-RN:[1260659-18-4]) were dissolved in Pyridine (1.5 mL). Propylphosphonic anhydride (498 mg, 0.783 mmol, CAS-RN:[68957-94-8]) was added, and the reaction mixture was stirred at 20° C. for 12 h. The reaction mixture was concentrated in vacuo. Preparative-HPLC (column: Phenomenex Gemini 150×25 mm×10 um; Gradient: [water (modified with 0.05% $NH_3$—$H_2O$)-MeCN] 18%-48% over 10 min) followed by lyophilization to give 53.0 mg (39.9% yield, 93.8% purity) of the title compound as an off-white solid.

LCMS (Method 3): $R_t$=0.96 min.; MS (ESIpos): m/z=478.1 $[M+H]^+$. $^1H$ NMR (400 MHZ, DMSO-d6) δ[ppm]=12.09 (s, 1H), 10.71 (s, 1H), 8.47-8.40 (m, 2H), 8.35 (s, 1H), 8.29 (d, J=5.2 Hz, 1H), 8.14 (d, J=8.0 Hz, 1H), 7.89-7.83 (m, 2H), 7.76 (d, J=2.4 Hz, 1H), 7.27-7.22 (m, 2H), 7.14 (dd, J=1.6, 5.2 Hz, 1H), 6.30 (d, J=2.4 Hz, 1H), 5.07 (q, J=9.2 Hz, 2H), 3.74 (s, 2H).

Example 21

2-[1-methyl-5-(trifluoromethyl)pyrazol-3-yl]-N-[4-[3-(2-pyridyl)-1H-pyrrolo[3,2-b]pyridin-2-yl]-2-pyridyl]acetamide

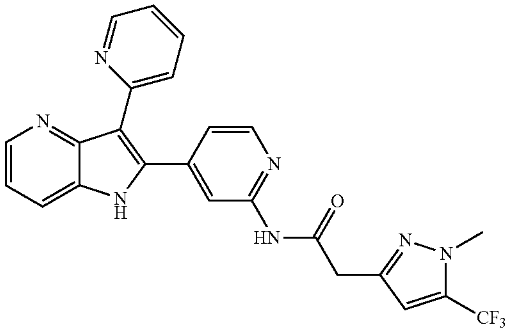 [SMILES: Cn1nc(CC(=O)Nc2cc(-c3[nH]c4cccnc4c3-c3ccccn3)ccn2)cc1C(F)(F)F]

4-[3-(2-pyridyl)-1H-pyrrolo[3,2-b]pyridin-2-yl]pyridin-2-amine (150 mg, 0.261 mmol, 50% purity, see Intermediate 8) and 2-[1-methyl-5-(trifluoromethyl)pyrazol-3-yl]acetic acid (81.5 mg, 0.392 mmol, CAS-RN:[1260658-98-7]) were dissolved in Pyridine (1.5 mL). Propylphosphonic anhydride (498 mg, 0.783 mmol, CAS-RN:[68957-94-8]) was added, and the resulting mixture was stirred at 20° C. for 12 h. The reaction mixture was concentrated in vacuo. Preparative-HPLC (column: Phenomenex Gemini 150×25 mm×10 um; Gradient: [water (modified with 0.05% $NH_3$—$H_2O$)-MeCN] 23%-53% over 10 min) followed by lyophilization gave 29.0 mg (21.8% yield, 93.7% purity) of the title compound as an off-white solid. LCMS (Method 3): $R_t$=1.08 min.; MS (ESIpos): m/z=478.2 $[M+H]^+$. $^1H$ NMR (400 MHZ, DMSO-d6) δ[ppm]=12.08 (s, 1H), 10.79 (s, 1H), 8.44 (ddd, J=1.2, 4.8, 10.4 Hz, 2H), 8.34 (s, 1H), 8.30 (d, J=5.2 Hz, 1H), 8.14 (d, J=8.0 Hz, 1H), 7.87 (dd, J=1.2, 8.0 Hz, 2H), 7.28-7.21 (m, 2H), 7.15 (dd, J=1.6, 5.6 Hz, 1H), 6.78 (s, 1H), 3.92 (s, 3H), 3.78 (s, 2H).

Example 22

2-isothiazol-5-yl-N-[4-[3-(2-pyridyl)-1H-pyrrolo[3,2-b]pyridin-2-yl]-2-pyridyl]acetamide

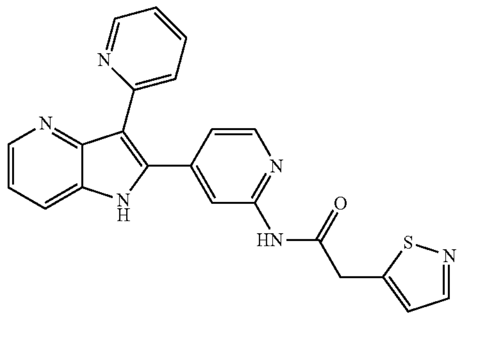

4-[3-(2-pyridyl)-1H-pyrrolo[3,2-b]pyridin-2-yl]pyridin-2-amine (150 mg, 0.261 mmol, 50% purity, see Intermediate 8) and 5-isothiazoleacetic acid (56.1 mg, 0.392 mmol, CAS-RN:[10271-84-8]) were dissolved in Pyridine (1.5 mL). Propylphosphonic anhydride (498 mg, 0.783 mmol, CAS-RN:[68957-94-8]) was added, and the resulting mixture was stirred at 25° C. for 12 h, and then heated to 40° C. for 2 h. The reaction mixture was concentrated in vacuo. Preparative-HPLC (column: Phenomenex Gemini 150×25 mm×10 um; Gradient: [water (modified with 0.05% $NH_3$—$H_2O$)-MeCN] 14%-44% over 10 min) followed by lyophilization to give 43.0 mg (38.6% yield, 96.5% purity) of the title compound as a yellow solid. LCMS (Method 3): $R_t$=0.86 min.; MS (ESIpos): m/z=413.2 $[M+H]^+$. $^1H$ NMR (400 MHZ, DMSO-d6) δ[ppm]=12.11 (s, 1H), 10.98 (s, 1H), 8.47-8.41 (m, 3H), 8.36 (s, 1H), 8.32 (d, J=5.2 Hz, 1H), 8.14 (d, J=8.0 Hz, 1H), 7.90-7.85 (m, 2H), 7.30-7.23 (m, 3H), 7.19 (dd, J=1.6, 5.2 Hz, 1H), 4.28 (s, 2H).

Example 23

2-isoxazol-5-yl-N-[4-[3-(2-pyridyl)-1H-pyrrolo[3,2-b]pyridin-2-yl]-2-pyridyl]acetamide

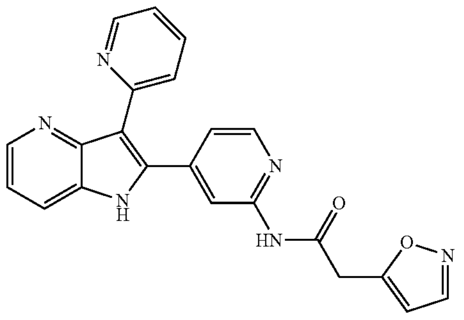 [SMILES: O=C(Cc1ccno1)Nc1cc(-c2[nH]c3cccnc3c2-c2ccccn2)ccn1]

4-[3-(2-pyridyl)-1H-pyrrolo[3,2-b]pyridin-2-yl]pyridin-2-amine (150 mg, 0.261 mmol, 50% purity, see Intermediate 8) and 5-isoxazoleacetic acid (49.8 mg, 0.392 mmol, CAS-RN:[4992-21-6]) were dissolved in Pyridine (1.5 mL). Propylphosphonic anhydride (498 mg, 0.783 mmol, CAS-RN: [68957-94-8]) was added, and the resulting mixture was stirred at 40° C. for 12 h. Another addition of 5-isoxazoleacetic acid (49.8 mg, 0.392 mmol, CAS-RN:[4992-21-6]) was added to the mixture, which was stirred at 60° C. for 4 h. The reaction mixture was concentrated in vacuo. Preparative-HPLC (column: Phenomenex Luna C18 150×25 mm×10 um; Gradient: [water (modified with 0.225% formic acid)-MeCN] 1%-28% over 10 min), followed by preparative-HPLC (column: Phenomenex Gemini 150×25 mm×10 um; Gradient: [water (modified with 0.05% $NH_3$—$H_2O$)-MeCN] 18%-42% over 8 min) followed by lyophilization to give 19.0 mg (17.8% yield, 97.2% purity) of the title compound as a yellow solid. LCMS (Method 3): $R_t$=0.86 min.; MS (ESIpos): m/z=397.0 $[M+H]^+$. $^1H$ NMR (400 MHZ, DMSO-d6) δ[ppm]=12.10 (s, 1H), 10.93 (s, 1H), 8.51 (d, J=1.6 Hz, 1H), 8.47-8.41 (m, 2H), 8.34-8.29 (m, 2H), 8.14 (d, J=8.0 Hz, 1H), 7.87 (dd, J=1.2, 8.0 Hz, 2H), 7.28-7.23 (m, 2H), 7.20-7.17 (m, 1H), 6.41 (d, J=1.2 Hz, 1H), 4.07 (s, 2H).

Example 24

2-(2-methyloxazol-5-yl)-N-[4-[3-(2-pyridyl)-1H-pyrrolo[3,2-b]pyridin-2-yl]-2-pyridyl]acetamide

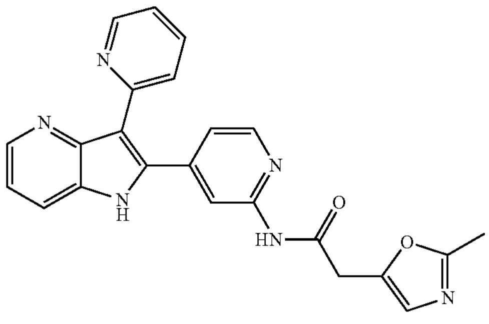 [SMILES: Cc1ncc(CC(=O)Nc2cc(-c3[nH]c4cccnc4c3-c3ccccn3)ccn2)o1]

4-[3-(2-pyridyl)-1H-pyrrolo[3,2-b]pyridin-2-yl]pyridin-2-amine (150 mg, 0.261 mmol, 50% purity, see Intermediate 8) and 2-(2-methyloxazol-5-yl)acetic acid (55.3 mg, 0.392 mmol, see Intermediate 23) were dissolved in Pyridine (1.5 mL). Propylphosphonic anhydride (498 mg, 0.783 mmol, CAS-RN:[68957-94-8]) was added, and the resulting mixture was stirred at 40° C. for 12 h. The reaction mixture was concentrated in vacuo. Preparative-HPLC (column: Phenomenex Gemini 150×25 mm×10 um; Gradient: [water (modified with 0.05% $NH_3$—$H_2O$)-MeCN] 12%-42% over 8 min) followed by lyophilization to give 14 mg (12.9% yield, 98.8% purity) of the title compound as a yellow solid. LCMS (Method 3): $R_t$=0.80 min.; MS (ESIpos): m/z=411.2 $[M+H]^+$. $^1$H NMR (400 MHz, DMSO-d6) δ[ppm]=12.10 (s, 1H), 10.83 (s, 1H), 8.47-8.41 (m, 2H), 8.35-8.29 (m, 2H), 8.14 (d, J=8.0 Hz, 1H), 7.89-7.84 (m, 2H), 7.28-7.23 (m, 2H), 7.17 (dd, J=1.6, 5.2 Hz, 1H), 6.86 (s, 1H), 3.87 (s, 2H), 2.36 (s, 3H).

Example 25

2-(2-methyloxazol-4-yl)-N-[4-[3-(2-pyridyl)-1H-pyrrolo[3,2-b]pyridin-2-yl]-2-pyridyl]acetamide

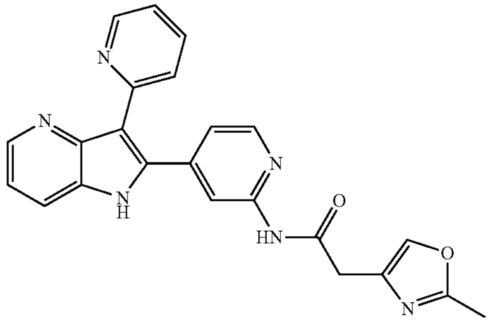 [SMILES: Cc1nc(CC(=O)Nc2cc(-c3[nH]c4cccnc4c3-c3ccccn3)ccn2)co1]

4-[3-(2-pyridyl)-1H-pyrrolo[3,2-b]pyridin-2-yl]pyridin-2-amine (150 mg, 0.261 mmol, 50% purity, see Intermediate 8) and 2-methyl-4-oxazoleacetic acid (55.3 mg, 0.392 mmol, CAS-RN: [36042-28-1]) were dissolved in Pyridine (1.5 mL). Propylphosphonic anhydride (498 mg, 0.783 mmol, CAS-RN:[68957-94-8]) was added, and the resulting mixture was stirred at 40° C. for 12 h. The reaction mixture was concentrated in vacuo. Preparative-HPLC (column: Phenomenex Gemini 150×25 mm×10 um; Gradient: [water (modified with 0.05% $NH_3$—$H_2O$)-MeCN] 13%-43% over 10 min) followed by lyophilization to give 37 mg (33.1% yield, 95.8% purity) of the title compound as a yellow solid. LCMS (Method 3): $R_t$=0.900 min.; MS (ESIpos): m/z=411.0 $[M+H]^+$. $^1$H NMR (400 MHZ, DMSO-d6) δ[ppm]=12.10 (s, 1H), 10.68 (s, 1H), 8.46-8.42 (m, 2H), 8.34 (s, 1H), 8.29 (d, J=5.2 Hz, 1H), 8.14 (d, J=8.0 Hz, 1H), 7.87 (dd, J=1.6, 8.0 Hz, 2H), 7.79 (s, 1H), 7.27-7.23 (m, 2H), 7.15 (dd, J=1.6, 5.2 Hz, 1H), 3.63 (s, 2H), 2.37 (s, 3H).

Example 26

2-(5-methylisoxazol-3-yl)-N-[4-[3-(2-pyridyl)-1H-pyrrolo[3,2-b]pyridin-2-yl]-2-pyridyl]acetamide

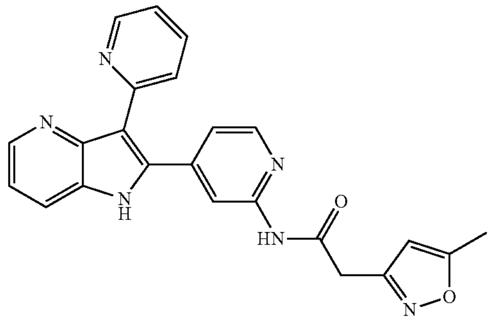 [SMILES: Cc1cc(CC(=O)Nc2cc(-c3[nH]c4cccnc4c3-c3ccccn3)ccn2)no1]

4-[3-(2-pyridyl)-1H-pyrrolo[3,2-b]pyridin-2-yl]pyridin-2-amine (150 mg, 0.261 mmol, 50% purity, see Intermediate 8) and 2-(5-methylisoxazol-3-yl)acetic acid (55.3 mg, 0.392 mmol, CAS-RN: [57612-87-0]) were dissolved in Pyridine (1.5 mL). Propylphosphonic anhydride (498 mg, 0.783 mmol, CAS-RN:[68957-94-8]) was added, and the resulting mixture was stirred at 40° C. for 12 h. The reaction mixture was concentrated in vacuo. Preparative-HPLC (column: Phenomenex Gemini 150×25 mm×10 um; Gradient: [water (modified with 0.05% $NH_3$—$H_2O$)-MeCN] 15%-45% over 10 min) followed by lyophilization to give 30 mg (26.6% yield, 95.0% purity) of the title compound as an off-white solid. LCMS (Method 3): $R_t$=0.86 min.; MS (ESIpos): m/z=411.2 $[M+H]^+$. $^1$H NMR (400 MHZ, DMSO-d6) δ[ppm]=12.09 (s, 1H), 10.88 (s, 1H), 8.47-8.41 (m, 2H), 8.34-8.28 (m, 2H), 8.15 (d, J=8.0 Hz, 1H), 7.89-7.83 (m, 2H), 7.29-7.23 (m, 2H), 7.17 (dd, J=1.2, 5.2 Hz, 1H), 6.20 (s, 1H), 3.81 (s, 2H), 2.40-2.37 (m, 3H).

Example 27

2-(5-cyclopropylisoxazol-3-yl)-N-[4-[3-(2-pyridyl)-1H-pyrrolo[3,2-b]pyridin-2-yl]-2-pyridyl]acetamide

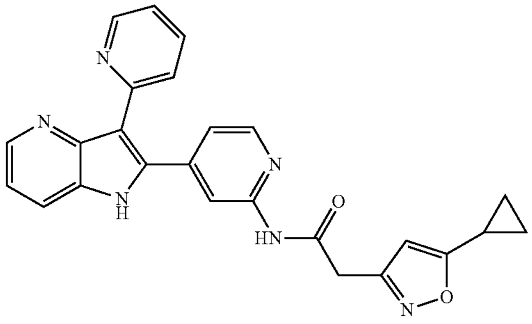 [SMILES: O=C(Cc1cc(C2CC2)on1)Nc1cc(-c2[nH]c3cccnc3c2-c2ccccn2)ccn1]

4-[3-(2-pyridyl)-1H-pyrrolo[3,2-b]pyridin-2-yl]pyridin-2-amine (150 mg, 0.261 mmol, 50% purity, see Intermediate 8) and 2-(5-cyclopropylisoxazol-3-yl)acetic acid (65.5 mg, 0.392 mmol, CAS-RN:[1368177-97-2]) were dissolved in Pyridine (1.5 mL). Propylphosphonic anhydride (498 mg, 0.783 mmol, CAS-RN:[68957-94-8]) was added, and the resulting mixture was stirred at 40° C. for 12 h. The reaction mixture was concentrated in vacuo. Preparative-HPLC (column: Phenomenex Gemini 150×25 mm×10 um; Gradient: [water (modified with 0.05% $NH_3$—$H_2O$)-MeCN] 23%-53% over 10 min) followed by lyophilization to give 40 mg (33.8% yield, 96.3% purity) of the title compound as a yellow solid. LCMS (Method 3): $R_t$=1.09 min.; MS (ESIpos): m/z=436.9 $[M+H]^+$. $^1H$ NMR (400 MHZ, DMSO-d6) δ[ppm]=12.10 (s, 1H), 10.88 (s, 1H), 8.50-8.39 (m, 2H), 8.36-8.28 (m, 2H), 8.15 (d, J=8.0 Hz, 1H), 7.88 (dd, J=1.6, 8.0 Hz, 2H), 7.29-7.23 (m, 2H), 7.18 (dd, J=1.6, 5.2 Hz, 1H), 6.16 (s, 1H), 3.80 (s, 2H), 2.16-2.09 (m, 1H), 1.07-1.02 (m, 2H), 0.86 (dd, J=2.4, 4.8 Hz, 2H).

Example 28

2-(1-isopropylpyrazol-3-yl)-N-[4-[3-(2-pyridyl)-1H-pyrrolo[3,2-b]pyridin-2-yl]-2-pyridyl]acetamide

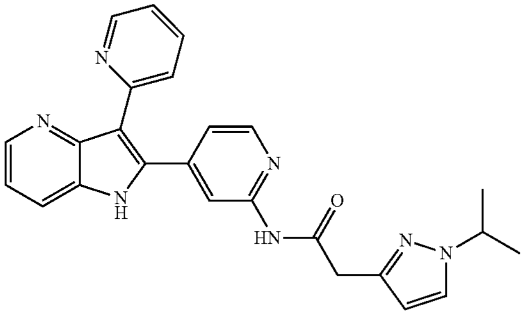 [SMILES: CC(C)n1ccc(CC(=O)Nc2cc(-c3[nH]c4cccnc4c3-c3ccccn3)ccn2)n1]

4-[3-(2-pyridyl)-1H-pyrrolo[3,2-b]pyridin-2-yl]pyridin-2-amine (150 mg, 0.261 mmol, 50% purity, see Intermediate 8) and 2-(1-isopropylpyrazol-3-yl)acetic acid (65.9 mg, 0.392 mmol, CAS-RN:[1260658-97-6]) were dissolved in Pyridine (2.0 mL). Propylphosphonic anhydride (498 mg, 0.783 mmol, CAS-RN:[68954-97-8]) was added, and the resulting mixture was stirred at 25° C. for 12 h. The reaction mixture was concentrated in vacuo. Preparative-HPLC (column: Phenomenex Gemini 150×25 mm×10 um; Gradient: [water (modified with 0.05% $NH_3$—$H_2O$)-MeCN] 18%-48% over 10 min) followed by lyophilization to give 54.0 mg (46.7% yield, 98.7% purity) of the title compound as a white solid. LCMS (Method 3): $R_t$=1.00 min.; MS (ESIpos): m/z=438.2 $[M+H]^+$. $^1H$ NMR (400 MHZ, DMSO-d6) δ[ppm]=12.10 (s, 1H), 10.63 (s, 1H), 8.47-8.42 (m, 2H), 8.35 (s, 1H), 8.29 (d, J=5.2 Hz, 1H), 8.13 (d, J=8.0 Hz, 1H), 7.87 (d, J=8.0 Hz, 2H), 7.66 (d, J=2.0 Hz, 1H), 7.28-7.23 (m, 2H), 7.15 (dd, J=1.2, 5.2 Hz, 1H), 6.15 (d, J=2.0 Hz, 1H), 4.49-4.40 (m, 1H), 3.70 (s, 2H), 1.40 (d, J=6.8 Hz, 6H).

Example 29

2-(5-cyclopropyl-1-methyl-pyrazol-3-yl)-N-[4-[3-(2-pyridyl)-1H-pyrrolo[3,2-b]pyridin-2-yl]-2-pyridyl]acetamide

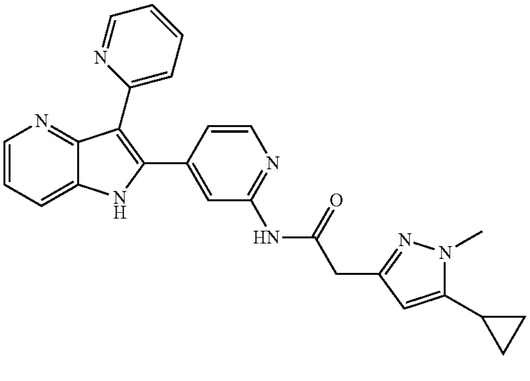 [SMILES: Cn1nc(CC(=O)Nc2cc(-c3[nH]c4cccnc4c3-c3ccccn3)ccn2)cc1C1CC1]

4-[3-(2-pyridyl)-1H-pyrrolo[3,2-b]pyridin-2-yl]pyridin-2-amine (150 mg, 0.261 mmol, 50% purity, see Intermediate 8) and 2-(5-cyclopropyl-1-methyl-pyrazol-3-yl)acetic acid (70.6 mg, 0.392 mmol, CAS-RN:[1226153-59-8]) were dissolved in Pyridine (2.0 mL). Propylphosphonic anhydride (498 mg, 0.783 mmol, CAS-RN:[68957-94-8]) was added, and the resulting mixture was stirred at 25° C. for 12 h. The reaction mixture was concentrated in vacuo. Preparative-HPLC (column: Phenomenex Gemini 150×25 mm×10 um; Gradient: [water (modified with 0.05% $NH_3$—$H_2O$)-MeCN] 20%-50% over 10 min) followed by lyophilization to give 42.0 mg (35.1% yield, 98.2% purity) of the title compound as a white solid. LCMS (Method 3): $R_t$=0.99 min.; MS (ESIpos): m/z=450.2 $[M+H]^+$. $^1H$ NMR (400 MHZ, DMSO-d6) δ[ppm]=12.08 (s, 1H), 10.57 (s, 1H), 8.44 (ddd, J=1.2, 4.8, 9.6 Hz, 2H), 8.33 (s, 1H), 8.28 (d, J=5.2 Hz, 1H), 8.14 (d, J=8.0 Hz, 1H), 7.89-7.83 (m, 2H), 7.28-7.22 (m, 2H), 7.13 (dd, J=1.6, 5.6 Hz, 1H), 5.77 (s, 1H), 3.76 (s, 3H), 3.58 (s, 2H), 1.87-1.79 (m, 1H), 0.95-0.90 (m, 2H), 0.57 (dd, J=2.0, 5.2 Hz, 2H).

Example 30

2-(3-methylisoxazol-4-yl)-N-[4-[3-(2-pyridyl)-1H-pyrrolo[3,2-b]pyridin-2-yl]-2-pyridyl]acetamide

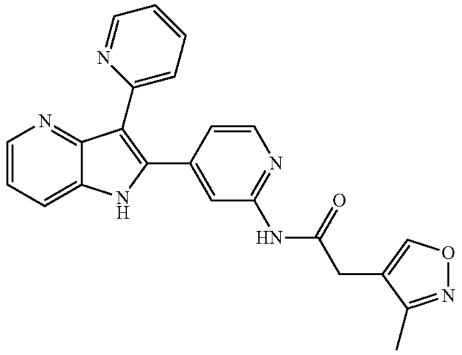 [SMILES: Cc1nocc1CC(=O)Nc1cc(-c2[nH]c3cccnc3c2-c2ccccn2)ccn1]

4-[3-(2-pyridyl)-1H-pyrrolo[3,2-b]pyridin-2-yl]pyridin-2-amine (150 mg, 0.261 mmol, 50% purity, see Intermediate 8) and 2-(3-methylisoxazol-4-yl)acetic acid (55.3 mg, 0.392 mmol, CAS-RN: [1008304-86-6]) were dissolved in Pyridine (2.0 mL). Propylphosphonic anhydride (498 mg, 0.783 mmol, CAS-RN:[68957-94-8]) was added, and the resulting mixture was stirred at 40° C. for 12 h. The reaction mixture was concentrated in vacuo. Preparative-HPLC (column: Phenomenex Gemini 150×25 mm×10 um; Gradient: [water (modified with 0.05% $NH_3$—$H_2O$)-MeCN] 13%-43% over 10 min) followed by lyophilization to give 47.0 mg (42.5% yield, 96.8% purity) of the target compound as a yellow solid.

LCMS (Method 3): $R_t$=0.91 min.; MS (ESIpos): m/z=411.0 $[M+H]^+$. $^1H$ NMR (400 MHZ, DMSO-d6) δ[ppm]=12.07 (s, 1H), 10.80 (s, 1H), 8.65 (s, 1H), 8.46-8.41 (m, 2H), 8.33-8.29 (m, 2H), 8.12 (d, J=8.0 Hz, 1H), 7.88-7.84 (m, 2H), 7.27-7.22 (m, 2H), 7.19-7.16 (m, 1H), 3.62 (s, 2H), 2.20 (s, 3H).

Example 31

4,4-difluoro-2-(2-methylthiazol-4-yl)-N-[4-[3-(2-pyridyl)-1H-pyrrolo[3,2-b]pyridin-2-yl]-2-pyridyl]butanamide

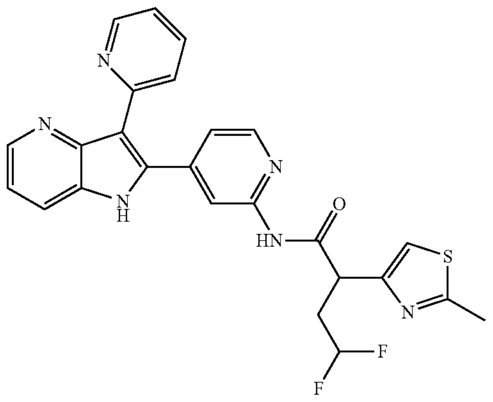 [SMILES: Cc1nc(C(CC(F)F)C(=O)Nc2cc(-c3[nH]c4cccnc4c3-c3ccccn3)ccn2)cs1]

4,4-difluoro-2-(2-methylthiazol-4-yl)butanoic acid (50 mg, 226 µmol, see Intermediate 8) and 4-[3-(2-pyridyl)-1H-pyrrolo[3,2-b]pyridin-2-yl]pyridin-2-amine (97.4 mg, 339 µmol, see Intermediate 27) were dissolved in DMF (1.0 mL). CMPI (86.6 mg, 339 µmol, CAS-RN:[14338-32-0]) and $Et_3N$ (68.6 mg, 678 µmol, CAS-RN:[121-44-8]) were added, and the resulting mixture was stirred at 25° C. for 1 h. A brown suspension formed, and the suspension was filtered and the filtrate was collected. Preparative-HPLC (column: Phenomenex C18 150×25 mm×10 um; Gradient: [water (modified with 10 mM $NH_4$—$HCO_3$)-MeCN] 25%-55% over 10 min) followed by lyophilization to give 5.77 mg (5.2% yield) of the title compound as a white solid. LCMS (Method 3): $R_t$=1.39 min.; MS (ESIpos): m/z=491.3 $[M+H]^+$. $^1H$ NMR (400 MHZ, DMSO-d6) δ 12.10 (s, 1H), 10.83 (s, 1H), 8.45 (dd, J=1.2, 4.4 Hz, 1H), 8.40 (d, J=4.0 Hz, 1H), 8.36 (s, 1H), 8.27 (d, J=5.2 Hz, 1H), 8.14 (d, J=8.0 Hz, 1H), 7.91-7.82 (m, 2H), 7.38 (s, 1H), 7.25 (dt, J=4.8, 8.0 Hz, 2H), 7.12 (dd, J=1.4, 5.1 Hz, 1H), 6.25-5.89 (m, 1H), 4.40-4.32 (m, 1H), 2.63 (s, 3H), 2.44-2.37 (m, 2H)

Example 32

4,4-difluoro-2-oxazol-5-yl-N-[4-[3-(2-pyridyl)-1H-pyrrolo[3,2-b]pyridin-2-yl]-2-pyridyl]butanamide

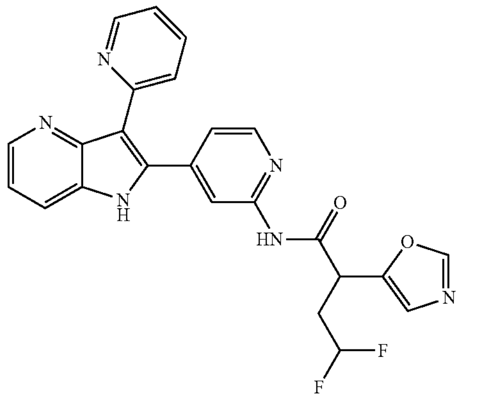 [SMILES: O=C(Nc1cc(-c2[nH]c3cccnc3c2-c2ccccn2)ccn1)C(CC(F)F)c1cnco1]

4,4-difluoro-2-(oxazol-5-yl)butanoic acid (130 mg, 680 µmol, see Intermediate 32) and diisopropylethylamine (264 mg, 2.04 mmol, CAS-RN:[7087-68-5]) were dissolved in DMF (0.5 mL). CMPI (347 mg, 1.36 mmol, CAS-RN: [14338-32-0]) was added, and the resulting mixture stirred at 25° C. for 5 min. Then 4-[3-(2-pyridyl)-1H-pyrrolo[3,2-b]pyridin-2-yl]pyridin-2-amine (195 mg, 680 µmol, see Intermediate 8) was added, and the resulting mixture was stirred at 25° C. for 1 h. A yellow precipitate formed, and the resulting suspension was filtered, and the filtrate was collected. Preparative-HPLC (column: Welch Xtimate C18 150×25 mm×5 um; Gradient: [water (modified with HCl)-MeCN] 7%-37% over 9 min) followed by lyophilization to give 24.9 mg (7.2% yield, 90.8% purity) of the title compound as a brown gum. LCMS (Method 3): $R_t$=0.83 min.; MS (ESIpos): m/z=461.1 $[M+H]^+$. $^1H$ NMR (400 MHz, DMSO-d6) δ 13.60 (s, 1H), 11.31 (s, 1H), 8.83 (d, J=4.4 Hz, 1H), 8.75-8.67 (m, 1H), 8.58-8.49 (m, 2H), 8.42-8.30 (m, 2H), 8.01 (dt, J=1.6, 7.6 Hz, 1H), 7.74 (dd, J=5.6, 8.4 Hz, 1H), 7.63-7.53 (m, 2H), 7.38 (dd, J=1.6, 5.2 Hz, 1H), 7.13 (s, 1H), 6.32-5.98 (m, 1H), 4.50-4.49 (m, 1H), 2.44-2.37 (m, 2H).

Example 33

2-([1,2,4]triazolo[1,5-a]pyridin-6-yl)-N-(4-(3-(pyridin-2-yl)-1H-pyrrolo[3,2-b]pyridin-2-yl)pyridin-2-yl)acetamide

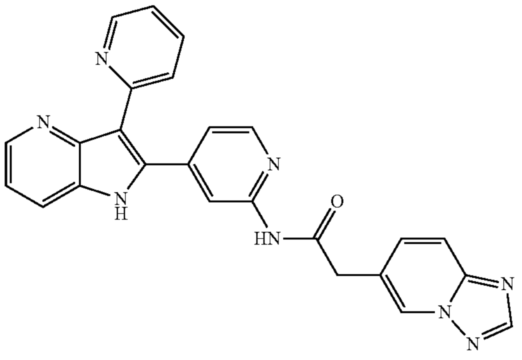 [SMILES: O=C(Cc1ccc2ncnn2c1)Nc1cc(-c2[nH]c3cccnc3c2-c2ccccn2)ccn1]

4-[3-(2-pyridyl)-1H-pyrrolo[3,2-b]pyridin-2-yl]pyridin-2-amine (57.0 mg, 0.198 mmol, see Intermediate 8) and 2-([1,2,4]triazolo[1,5-a]pyridin-6-yl)acetic acid (35.0 mg, 0.198 mmol, see Intermediate 37) were dissolved in dichloromethane (2.00 mL). Pyridine (0.10 mL, 1.19 mmol, CAS-RN: [110-86-1]) and propylphosphonic anhydride (251 mg, 0.395 mmol, CAS-RN:[68954-97-8]) were added, and the resulting mixture was stirred at 25° C. for 4 h. Water (10 mL) was added to the mixture, and the mixture was extracted with DCM (3×15 mL). The combined organic phase was dried (magnesium sulfate), filtered, and the solvent removed in vacuo. Preparative-HPLC (column: Waters xBridge prep C18 5 µm OBD, Size: 19×250 mm; Gradient: water/acetonitrile (both modified with 0.1% formic acid) 12%-30% over 15 min) followed by lyophilization to give 1.5 mg (0.00319 mmol, 97.5% purity, 2% yield) of the title compound as a white solid. LCMS (Method 4)=1.36 min, MS (ESIpos) m/z=447.33 $[M+H]^+$ $^1H$ NMR (400 MHZ, DMSO) δ 12.04 (s, 1H), 10.88 (s, 1H), 8.90 (s, 1H), 8.47 (s, 1H), 8.44 (dd, J=4.6, 1.5 Hz, 1H), 8.40 (dd, J=4.9, 1.8 Hz, 1H), 8.38 (s, 1H), 8.31 (s, 1H), 8.12

(d, J=7.9 Hz, 1H), 7.87-7.81 (m, 3H), 7.63 (dd, J=9.2, 1.7 Hz, 1H), 7.27-7.20 (m, 2H), 7.17 (dd, J=5.1, 1.7 Hz, 1H), 3.89 (s, 2H).

Example 34

4,4-difluoro-N-(4-(5-fluoro-3-(pyridin-2-yl)-1H-pyrrolo[3,2-b]pyridin-2-yl)pyridin-2-yl)-2-(2-methylthiazol-4-yl) butanamide

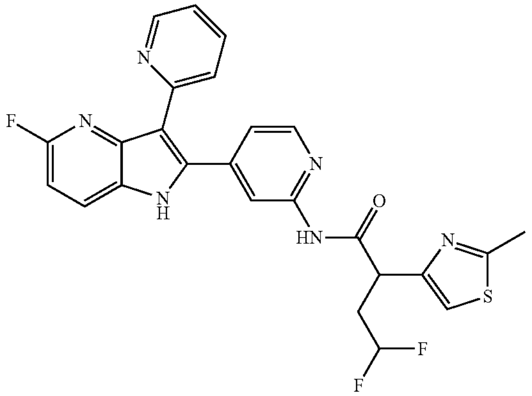 [SMILES: Cc1nc(C(CC(F)F)C(=O)Nc2cc(-c3[nH]c4ccc(F)nc4c3-c3ccccn3)ccn2)cs1]

4-[5-fluoro-3-(2-pyridyl)-1H-pyrrolo[3,2-b]pyridin-2-yl] pyridin-2-amine (16 mg, 0.0524 mmol, see Intermediate 4), 4,4-difluoro-2-(2-methylthiazol-4-yl)butanoic acid (13 mg, 0.0588 mmol, see Intermediate 27), diisopropylethylamine (0.05 mL, 0.262 mmol, CAS-RN:[7087-68-5]), and a 50% by weight solution of propylphosphonic anhydride in THF (0.09 mL, 0.157 mmol, CAS-RN: [68954-94-8]) were dissolved in THF (0.52 mL). The resulting mixture was stirred at 40° C. for 5 h. The reaction mixture was concentrated in vacuo. Preparative HPLC (Column: Waters XBridge C18 19 mm×250 mm; Gradient (water to MeCN both modified with 0.1% formic acid) 35%-55% over 10 min) followed by lyophilization to give 7.1 mg (0.0140 mmol, 27% yield) of the title compound as a yellow powder. LCMS (Method 4): $R_t$=1.98 min.; MS (ESIpos) m/z=509.32 $[M+H]^+$. $^1H$ NMR (400 MHZ, DMSO-d6) δ[ppm] 12.33 (s, 1H), 10.83 (s, 1H), 8.43 (d, J=4.9 Hz, 1H), 8.35 (s, 1H), 8.28 (d, J=5.2 Hz, 1H), 8.04 (dd, J=8.6, 7.3 Hz, 1H), 7.99-7.92 (m, 1H), 7.88 (t, J=7.5 Hz, 1H), 7.37 (s, 1H), 7.27 (t, J=6.3 Hz, 1H), 7.10 (dd, J=5.2, 1.6 Hz, 1H), 7.00 (dd, J=8.7, 1.5 Hz, 1H), 6.26-5.85 (m, 1H), 4.40-4.22 (m, 1H), 2.63 (s, 3H), 2.45-2.36 (m, 2H).

BIOLOGICAL ASSAYS

The following assays can be used to illustrate the commercial utility of the compounds according to the present invention.

Examples were tested in selected biological assays one or more times. When tested more than once, data are reported as either average values or as median values or single individual measurements, wherein

- the average value, also referred to as the arithmetic mean value, represents the sum of the values obtained divided by the number of times tested, and
- the median value represents the middle number of the group of values when ranked in ascending or descending order. If the number of values in the data set is odd, the median is the middle value. If the number of values in the data set is even, the median is the arithmetic mean of the two middle values.

Individual measurements are shown when median or average values cannot be computed.

Examples were synthesized one or more times. When synthesized more than once, data from biological assays represent average values calculated utilizing data sets obtained from testing of one or more synthetic batch.

The in vitro activity of the compounds of the present invention can be demonstrated in the following assays:

CSNK1A1 Assay

CSNK1A1-inhibitory activity of compounds of the present invention in presence of 1 μM adenosine-tri-phosphate (ATP) was quantified employing the CSNK1A1 assay as described in the following paragraphs. In essence, the enzyme activity is measured by quantification of the adenosine-di-phosphate (ADP), which is generated as a co-product of the enzyme reaction, via the "ADP-Glo™ Kinase Assay" kit from the company Promega. This detection system works as follows: In a first step the ATP not consumed in the kinase reaction is quantitatively converted to CAMP employing an adenylate cyclase ("ADP-Glo-reagent"), then the adenylate cyclase is stopped and the ADP generated in the kinase reaction converted to ATP which generates in a luciferase-based reaction a glow-luminescence signal ("Kinase Detection Reagent").

Recombinant fusion protein of N-terminal Glutathion-S-Transferase (GST) and full-length human CSNK1A1, expressed by baculovirus infected insect cells and purified via Glutathion affinity chromatography, was purchased from Life Technologies (product no. PV4174) and used as enzyme. As substrate for the kinase reaction the biotinylated peptide biotin-Ahx-KRRRAL-pS-VASLPGL (C-terminus in amide form) was used which can be purchased e.g. from the company Biosyntan (Berlin-Buch, Germany).

For the assay 50 nl of a 100-fold concentrated solution of the test compound in DMSO was pipetted into a white 1536-well microtiter plate (Greiner Bio-One, Frickenhausen, Germany), 2 μL of a solution of CSNK1A1 in aqueous assay buffer [50 mM HEPES pH 7.5, 10% (v/v) glycerol, 10 mM $MgCl_2$, 50 mM NaCl, 1 mM dithiothreitol, 0.01% (w/v) bovine serum albumin, 0.01% (v/v) Triton X-100] were added and the mixture was incubated for 15 min at 22° C. to allow pre-binding of the test compounds to the enzyme before the start of the kinase reaction. Then the kinase reaction was started by the addition of 3 μL of a solution of ATP (1.67 μM=>final conc. in the 5 μL assay volume is 1 μM) and peptide substrate (50 μM=>final conc. in the 5 μL assay volume is 30 μM) in assay buffer and the resulting mixture was incubated for a reaction time of 30 min at 22° C. The concentration of CSNK1A1 was adjusted depending of the activity of the enzyme lot and was chosen appropriate to have the assay in the linear range, a typical concentrations are about 0.0375 ng/μL. The reaction was stopped by the addition of 2.5 μL of "ADP-Glo-reagent" (1:1.5 fold diluted with water) and the resulting mixture was incubated at 22° C. for 1 h to convert the ATP not consumed in the kinase reaction completely to CAMP. Subsequently 2.5 μL of the "kinase detection reagent" (1.2 fold more concentrated than recommended by the producer) were added, the resulting mixture was incubated at 22° C. for 1 h and then the luminescence measured with a suitable measurement instrument (e.g. Viewlux™ from Perkin-Elmer). The amount of emitted light was taken as a measure for the amount of ADP generated and thereby for the activity of the CSNK1A1.

The data were normalised (enzyme reaction without inhibitor=0% inhibition, all other assay components but no enzyme=100% inhibition). Usually the test compounds were tested on the same microtiterplate in 11 different concentrations in the range of 20 μM to 0.07 nM (20 μM, 5.7 μM, 1.6 μM, 0.47 μM, 0.13 μM, 38 nM, 11 nM, 3.1 nM, 0.9 nM, 0.25 nM and 0.07 nM, the dilution series prepared separately before the assay on the level of the 100 fold concentrated solutions in DMSO by serial dilutions, exact concentrations may vary depending pipettors used) in duplicate values for each concentration and $IC_{50}$ values were calculated using Genedata Screener™ software.

CSNK1A1 High ATP Assay

CSNK1A1-inhibitory activity of compounds of the present invention in presence of 1 mM adenosine-tri-phosphate (ATP) was quantified employing the CSNK1A1-high-ATP-assay as described in the following paragraphs. In essence, the enzyme activity is measured by quantification of the adenosine-di-phosphate (ADP), which is generated as a co-product of the enzyme reaction, via the "ADP-Glo™ Kinase Assay" kit from the company Promega. This detection system works as follows: In a first step the ATP not consumed in the kinase reaction is quantitatively converted to CAMP employing an adenylate cyclase ("ADP-Glo-reagent"), then the adenylate cyclase is stopped and the ADP generated in the kinase reaction converted to ATP which generates in a luciferase-based reaction a glow-luminescence signal ("Kinase Detection Reagent").

Recombinant fusion protein of N-terminal Glutathion-S-Transferase (GST) and full-length human CSNK1A1, expressed by baculovirus infected insect cells and purified via Glutathion affinity chromatography, was purchased from Life Technologies (product no. PV4174) and used as enzyme. As substrate for the kinase reaction the biotinylated peptide biotin-Ahx-KRRRAL-pS-VASLPGL (C-terminus in amide form) was used which can be purchased e.g. from the company Biosyntan (Berlin-Buch, Germany).

For the assay 50 nl of a 100 fold concentrated solution of the test compound in DMSO was pipetted into a white low volume 384-well microtiter plate (Greiner Bio-One, Frickenhausen, Germany), 2 μL of a solution of CSNK1A1 in aqueous assay buffer [50 mM HEPES pH 7.5, 10% (v/v) glycerol, 10 mM $MgCl_2$, 50 mM NaCl, 1 mM dithiothreitol, 0.01% (w/v) bovine serum albumin, 0.01% (v/v) Triton X-100] were added and the mixture was incubated for 15 min at 22° C. to allow pre-binding of the test compounds to the enzyme before the start of the kinase reaction. Then the kinase reaction was started by the addition of 3 μL of a solution of ATP (1.67 mM=>final conc. in the 5 μL assay volume is 1 mM) and peptide substrate (167 μM=>final conc. in the 5 μL assay volume is 100 μM) in assay buffer and the resulting mixture was incubated for a reaction time of 30 min at 22° C. The concentration of CSNK1A1 was adjusted depending of the activity of the enzyme lot and was chosen appropriate to have the assay in the linear range, a typical concentration is about 0.4 ng/μL. The reaction was stopped by the addition of 2.5 μL of "ADP-Glo-reagent" (1:1.5 fold diluted with water) and the resulting mixture was incubated at 22° C. for 1 h to convert the ATP not consumed in the kinase reaction completely to CAMP. Subsequently 2.5 μL of the "kinase detection reagent" (1.2 fold more concentrated than recommended by the producer) were added, the resulting mixture was incubated at 22° C. for 1 h and then the luminescence measured with a suitable measurement instrument (e.g. Viewlux™ from Perkin-Elmer). The amount of emitted light was taken as a measure for the amount of ADP generated and thereby for the activity of the CSNK1A1.

The data were normalised (enzyme reaction without inhibitor=0% inhibition, all other assay components but no enzyme=100% inhibition). Usually the test compounds were tested on the same microtiterplate in 11 different concentrations in the range of 20 μM to 0.07 nM (20 μM, 5.7 μM, 1.6 μM, 0.47 μM, 0.13 μM, 38 nM, 11 nM, 3.1 nM, 0.9 nM, 0.25 nM and 0.07 nM, the dilution series prepared separately before the assay on the level of the 100 fold concentrated solutions in DMSO by serial dilutions, exact concentrations may vary depending pipettors used) in duplicate values for each concentration and $IC_{50}$ values were calculated using Genedata Screener™ software.

CSNK1D Assay

CSNK1D-inhibitory activity of compounds of the present invention in presence of 1 μM adenosine-tri-phosphate (ATP) was quantified employing the CSNK1D assay as described in the following paragraphs. In essence, the enzyme activity is measured by quantification of the adenosine-di-phosphate (ADP), which is generated as a co-product of the enzyme reaction, via the "ADP-Glo™ Kinase Assay" kit from the company Promega. This detection system works as follows: In a first step the ATP not consumed in the kinase reaction is quantitatively converted to CAMP employing an adenylate cyclase ("ADP-Glo-reagent"), then the adenylate cyclase is stopped and the ADP generated in the kinase reaction converted to ATP which generates in a luciferase-based reaction a glow-luminescence signal ("Kinase Detection Reagent").

Recombinant fusion protein of N-terminal Glutathion-S-Transferase (GST) and full-length human CSNK1D, expressed by baculovirus infected insect cells and purified via Glutathion affinity chromatography, was purchased from Life Technologies (product no. PV3665) and used as enzyme. As substrate for the kinase reaction the biotinylated peptide Btn-Ahx-SGSEGDSESGEEEG (C-terminus in amide form) was used which can be purchased e.g. from the company Biosyntan (Berlin-Buch, Germany).

For the assay 50 nl of a 100-fold concentrated solution of the test compound in DMSO was pipetted into a white 1536-well microtiter plate (Greiner Bio-One, Frickenhausen, Germany), 2 μL of a solution of CSNK1D in aqueous assay buffer [50 mM HEPES pH 7.5, 10% (v/v) glycerol, 10 mM $MgCl_2$, 50 mM NaCl, 1 mM dithiothreitol, 0.01% (w/v) bovine serum albumin, 0.01% (v/v) Triton X-100] were added and the mixture was incubated for 15 min at 22° C. to allow pre-binding of the test compounds to the enzyme before the start of the kinase reaction. Then the kinase reaction was started by the addition of 3 μL of a solution of ATP (1.67 μM=>final conc. in the 5 μL assay volume is 1 μM) and peptide substrate (50 μM=>final conc. in the 5 μL assay volume is 30 μM) in assay buffer and the resulting mixture was incubated for a reaction time of 30 min at 22° C. The concentration of CSNK1D was adjusted depending of the activity of the enzyme lot and was chosen appropriate to have the assay in the linear range, a typical concentration is about 0.5 ng/μL. The reaction was stopped by the addition of 2.5 μL of "ADP-Glo-reagent" (1:1.5 fold diluted with water) and the resulting mixture was incubated at 22° C. for 1 h to convert the ATP not consumed in the kinase reaction completely to CAMP. Subsequently 2.5 μL of the "kinase detection reagent" (1.2 fold more concentrated than recommended by the producer) were added, the resulting mixture was incubated at 22° C. for 1 h and then the luminescence measured with a suitable measurement instrument (e.g. Viewlux™ from Perkin-Elmer). The amount of emitted light was taken as a measure for the amount of ADP generated and thereby for the activity of the CSNK1D.

The data were normalised (enzyme reaction without inhibitor=0% inhibition, all other assay components but no enzyme=100% inhibition). Usually the test compounds were tested on the same microtiterplate in 11 different concentrations in the range of 20 μM to 0.07 nM (20 μM, 5.7 μM, 1.6 μM, 0.47 μM, 0.13 μM, 38 nM, 11 nM, 3.1 nM, 0.9 nM, 0.25 nM and 0.07 nM, the dilution series prepared separately before the assay on the level of the 100 fold concentrated solutions in DMSO by serial dilutions, exact concentrations may vary depending pipettors used) in duplicate values for each concentration and $IC_{50}$ values were calculated using Genedata Screener™ software.

CSNK1G3 Assay

CSNK1G3-inhibitory activity of compounds of the present invention in presence of 1 μM adenosine-tri-phosphate (ATP) was quantified employing the CSNK1G3 assay as described in the following paragraphs. In essence, the enzyme activity is measured by quantification of the adenosine-di-phosphate (ADP), which is generated as a co-product of the enzyme reaction, via the "ADP-Glo™ Kinase Assay" kit from the company Promega. This detection system works as follows: In a first step the ATP not consumed in the kinase reaction is quantitatively converted to CAMP employing an adenylate cyclase ("ADP-Glo-reagent"), then the adenylate cyclase is stopped and the ADP generated in the kinase reaction converted to ATP which generates in a luciferase-based reaction a glow-luminescence signal ("Kinase Detection Reagent").

Recombinant fusion protein of N-terminal Glutathion-S-Transferase (GST) and full-length human CSNK1G3, expressed by baculovirus infected insect cells and purified via Glutathion affinity chromatography, was purchased from Life Technologies (product no. PV3838) and used as enzyme. As substrate for the kinase reaction the biotinylated peptide biotin-Ahx-KRRRAL-pS-VASLPGL (C-terminus in amide form) was used which can be purchased e.g. from the company Biosyntan (Berlin-Buch, Germany).

For the assay 50 nl of a 100 fold concentrated solution of the test compound in DMSO was pipetted into a white 1536-well microtiter plate (Greiner Bio-One, Frickenhausen, Germany), 2 μL of a solution of CSNK1G3 in aqueous assay buffer [50 mM HEPES pH 7.5, 10% (v/v) glycerol, 10 mM $MgCl_2$, 50 mM NaCl, 1 mM dithiothreitol, 0.01% (w/v) bovine serum albumin, 0.01% (v/v) Triton X-100] were added and the mixture was incubated for 15 min at 22° C. to allow pre-binding of the test compounds to the enzyme before the start of the kinase reaction. Then the kinase reaction was started by the addition of 3 μL of a solution of ATP (1.67 M=>final conc. in the 5 μL assay volume is 1 M) and peptide substrate (50 μM=>final conc. in the 5 μL assay volume is 30 μM) in assay buffer and the resulting mixture was incubated for a reaction time of 30 min at 22° C. The concentration of CSNK1G3 was adjusted depending of the activity of the enzyme lot and was chosen appropriate to have the assay in the linear range, a typical concentration is about 0.06 ng/μL. The reaction was stopped by the addition of 2.5 μL of "ADP-Glo-reagent" (1:1.5 fold diluted with water) and the resulting mixture was incubated at 22° C. for 1 h to convert the ATP not consumed in the kinase reaction completely to CAMP. Subsequently 2.5 μL of the "kinase detection reagent" (1.2 fold more concentrated than recommended by the producer) were added, the resulting mixture was incubated at 22° C. for 1 h and then the luminescence measured with a suitable measurement instrument (e.g. Viewlux™ from Perkin-Elmer). The amount of emitted light was taken as a measure for the amount of ADP generated and thereby for the activity of the CSNK1G3.

The data were normalised (enzyme reaction without inhibitor=0% inhibition, all other assay components but no enzyme=100% inhibition). Usually the test compounds were tested on the same microtiterplate in 11 different concentrations in the range of 20 μM to 0.07 nM (20 μM, 5.7 μM, 1.6 μM, 0.47 μM, 0.13 μM, 38 nM, 11 nM, 3.1 nM, 0.9 nM, 0.25 nM and 0.07 nM, the dilution series prepared separately before the assay on the level of the 100 fold concentrated solutions in DMSO by serial dilutions, exact concentrations may vary depending pipettors used) in duplicate values for each concentration and $IC_{50}$ values were calculated using Genedata Screener™ software.

Table 2 shows the results of the inhibition in the CSNK1A1, CSNK1D, and CSNK1G biochemical assays.

TABLE 2

| Example No | CSNK1A1 Low ATP $IC_{50}$ [mol/l] (median) | CSNK1D $IC_{50}$ [mol/l] (median) | CSNK1G $IC_{50}$ [mol/l] (median) | CSNK1A1 High ATP assay $IC_{50}$ [mol/l] (median) |
|---|---|---|---|---|
| 1 | 5.89E−9 | 1.14E−8 | 7.17E−8 | 3.85E−8 |
| 2 | 4.21E−9 | 1.11E−8 | 1.02E−7 | 3.16E−8 |
| 3 | 1.81E−9 | 5.01E−9 | 3.91E−8 | 3.08E−8 |
| 4 | 1.82E−9 | 5.22E−9 | 5.03E−8 | 4.70E−8 |
| 5 | 4.12E−9 | 1.31E−8 | 7.45E−8 | 5.89E−7 |
| 6 | 1.10E−9 | 3.44E−9 | 7.89E−9 | 6.06E−9 |
| 7 | — | — | — | — |
| 8 | — | — | — | — |
| 9 | 2.61E−9 | 5.66E−9 | 5.12E−8 | — |
| 10 | 1.97E−9 | 5.60E−9 | 3.30E−8 | — |
| 11 | 3.43E−9 | 8.09E−9 | 1.20E−7 | — |
| 12 | 1.71E−9 | 5.02E−9 | 6.26E−8 | 6.69E−8 |
| 13 | 1.69E−9 | 5.68E−9 | 2.86E−8 | 4.13E−8 |
| 14 | 1.94E−9 | 4.88E−9 | 3.54E−8 | 3.06E−8 |
| 15 | 1.07E−9 | 3.75E−9 | 1.03E−8 | 2.42E−8 |
| 16 | 2.74E−9 | 6.57E−9 | 3.17E−8 | 7.08E−8 |
| 17 | 2.97E−9 | 6.87E−9 | 6.82E−8 | 1.24E−7 |
| 18 | 1.46E−9 | 3.80E−9 | 1.54E−8 | 1.41E−8 |
| 19 | 6.82E−9 | 1.39E−8 | 6.27E−8 | 2.91E−7 |
| 20 | 1.88E−9 | 4.93E−9 | 1.48E−8 | 9.87E−8 |
| 21 | 1.62E−9 | 4.88E−9 | 2.97E−8 | 8.66E−8 |
| 22 | 1.47E−9 | 4.84E−9 | 2.70E−8 | 4.12E−8 |
| 23 | 1.42E−9 | 4.68E−9 | 2.73E−8 | 5.01E−8 |
| 24 | 1.95E−9 | 5.37E−9 | 3.99E−8 | — |
| 25 | 2.79E−9 | 8.44E−9 | 6.44E−8 | — |
| 26 | 2.03E−9 | 6.64E−9 | 2.65E−8 | 9.08E−8 |
| 27 | 1.57E−9 | 6.38E−9 | 1.97E−8 | 2.44E−7 |
| 28 | 2.28E−9 | 6.30E−9 | 2.04E−8 | — |
| 29 | 2.21E−9 | 6.48E−9 | 2.74E−8 | 1.88E−7 |
| 30 | 2.62E−9 | 6.69E−9 | 6.89E−8 | — |
| 31 | — | — | — | — |
| 32 | — | — | — | — |
| 33 | — | — | — | — |
| 34 | — | — | — | — |

Proliferation Assays

HTRF Total-p53 in MCF-7 Cells:

Day 1: MCF-7 cells were seeded (10,000 cells in 12 μl/well) in a 384-well-Small Volume-plate (Greiner Bio One #784075) in culture medium (RPMI 1640; (Biochrom; #F 1275; without PhenolRed)+FCS (final: 10%); (Biochrom; #S 0415)+Insulin (bovine); (final: 10 μg/mL, Biochrom; #K 3510)+L-Alanyl-L-Glutamine; (final: 2 mM, Biochrom; #K 0302)+Natriumpyruvat; (final: 1 mM, Biochrom; #L 0473)+ Non Essentiell Amino Acids; (final: 1×, Biochrom; #K 0293)). The cells were then treated with different compounds or DMSO (added with the HP Dispenser) and incubated for 2 h at 37° C. Following incubation, the cells were lysed in 4 μl of lysis buffer for 1 h shaking at RT. Finally, 4 μl of antibody solution was added and the samples are incubated overnight at RT, shaking.

Total-p53 was detected in a sandwich assay format using 2 different specific antibodies, one labeled with Eu3+-Cryptate (donor) and the second with d2 (acceptor). Kit: HTRF total p53 detection assay (Cisbio Cat: 64T53PEG).

Day 2: the plate was read on PHERAstar FS (BMG Labtech settings; optic module: HTRF; integration start: 60 μs; integration time: 400 μs; flash lamp). $IC_{50}$ values were calculated using the DRC application in ShiNy Analysis Platform-SNAP."

HT29:

CELL PROLIFERATION ASSAY CTG METHOD, 384-well version: Day 1: plated 400 cells/30 μL/well in growth medium (DMEM/Ham's F12; (Biochrom; #FG 4815, mit stabilem Glutamin)+FCS (final: 10%); (Biochrom; #S 0415)) in 384-well black plates (Corning #3571). Plated sister wells in a separate plate for time zero determination. Incubated all plates overnight at 37° C. Day 2: added test compounds in serial dilutions using the HP D300 Digital Dispenser and incubated at 37° C. for 96 h. Measured time zero plate: add 30 μL/well CTG solution (Promega CellTiter-Glo solution (catalog #G7573)) to wells in time zero plate; incubated for 2 minutes in a orbital shaker to induce cell lysis; allowed the plate to incubate at room temperature for additional 10 min to stabilize luminescent signal and read luminescence on PheraStar (rapid mode—0.02 sec/well; GAIN 3000). Day 6: Added 30 μL/well CTG solution to all test wells, incubated for 2 minutes in a orbital shaker to induce cell lysis; allowed the plate to incubate at room temperature for additional 10 min to stabilize luminescent signal and read luminescence on PheraStar (rapid mode—0.02 sec/well; GAIN 3000 Proliferation IC50s were calculated using the DRC application in ShiNy Analysis Platform-SNAP."

LoVo:

CELL PROLIFERATION ASSAY CTG METHOD, 384-well version: Day 1: plate 400 cells/30 μL/well in growth medium (RPMI 1640 (Gibco #61870-10; with Glutamax)+10% FBS) in 384-well black plates (Corning #3571). Plated sister wells in a separate plate for time zero determination. Incubated all plates overnight at 37° C. Day 2: added test compounds in serial dilutions using the HP D300 Digital Dispenser and incubate at 37° C. for 96 h. Measured time zero plate: add 30 μL/well CTG solution (Promega CellTiter-Glo solution (catalog #G7573)) to wells in time zero plate; incubated for 2 minutes in a orbital shaker to induce cell lysis; allowed the plate to incubate at room temperature for additional 10 min to stabilize luminescent signal and read luminescence on PheraStar (rapid mode-0.02 sec/well; GAIN 3000). Day 6: Added 30 μL/well CTG solution to all test wells, incubated for 2 minutes in a orbital shaker to induce cell lysis; allowed the plate to incubate at room temperature for additional 10 min to stabilize luminescent signal and read luminescence on PheraStar (rapid mode-0.02 sec/well; GAIN 3000). Proliferation IC50s were calculated using the DRC application in ShiNy Analysis Platform-SNAP."

HCT 116

400 HCT 116 cells/30 μL/well were plated in growth medium (DMEM/Ham's F12, 10% FCS) in a 384-well plate (CORNING #3571) at day 1. Reference plate was seeded for time zero determination. All plates were incubated overnight 37° C. Day 2: test compound was added in 7-step dilution and incubate at 37° C. for 96 h. Day 2: time zero plate: 30 μL/well CTG solution (Promega Cell Titer Glo solution; catalog #G755B and G756B) were added, incubated for 30 minutes, read luminescence on PheraStar. Day 6: compound treated plates: 30 μL/well CTG solution (Promega Cell Titer Glo solution; catalog #G755B and G756B) were added, incubated for 30 minutes, luminescence was read on PheraStar. Proliferation was calculated after subtracting time zero luminescence values from day 6 values and comparing to untreated wells. The IC50 values were determined using the four parameter fit.

Table 3 shows the results of the cell proliferation assays for MCF-7, HT-29, LoVo, and HCT-116 cell lines.

TABLE 3

| Example No. | HTRF total-p53 MCF-7, $IC_{50}$ - [mol/l] (median) | 2D-PROLI HT-29 CTG 96 h, $IC_{50}$ - [mol/l] (median) | 2D-PROLI LoVo CTG 96 h, $IC_{50}$ - [mol/l] (median) | 2D-PROLI HCT 116 CTG 96 h, $IC_{50}$ - [mol/l] (median) |
|---|---|---|---|---|
| 1 | 1.93E−7 | 2.67E−6 | 1.24E−5 | 3.87E−6 |
| 2 | 2.64E−7 | 2.67E−6 | 8.41E−6 | 3.60E−6 |
| 3 | 1.84E−7 | 4.45E−7 | 3.63E−7 | 3.59E−7 |
| 4 | 1.37E−7 | 5.88E−7 | 3.13E−6 | 5.35E−7 |
| 5 | 9.24E−7 | 3.42E−6 | 7.43E−6 | 2.79E−6 |
| 6 | 4.10E−8 | 1.25E−7 | 1.77E−7 | 9.11E−8 |
| 7 | — | — | — | — |
| 8 | — | — | — | — |
| 9 | 2.10E−7 | 8.60E−7 | 4.07E−6 | 8.17E−7 |
| 10 | 2.62E−7 | 7.97E−7 | 3.24E−6 | 8.48E−7 |
| 11 | 3.75E−7 | 1.41E−6 | 3.32E−6 | 9.64E−7 |
| 12 | 2.05E−7 | 1.19E−6 | 6.81E−6 | 1.08E−6 |
| 13 | 1.52E−7 | 4.42E−7 | 3.14E−6 | 6.26E−7 |
| 14 | 1.43E−7 | 5.08E−7 | 3.75E−6 | 5.44E−7 |
| 15 | 6.93E−8 | 1.49E−7 | 1.92E−7 | 1.71E−7 |
| 16 | 1.93E−7 | 6.27E−7 | 1.50E−6 | 7.06E−7 |
| 17 | 1.98E−7 | 1.18E−6 | 5.66E−6 | 1.03E−6 |
| 18 | 5.66E−8 | 2.20E−7 | 1.13E−6 | 1.79E−7 |
| 19 | 4.07E−7 | 1.24E−6 | 5.50E−6 | 1.68E−6 |
| 20 | 1.84E−7 | 3.41E−7 | 1.37E−6 | 3.44E−7 |
| 21 | 9.69E−8 | 2.22E−7 | 4.27E−7 | 3.62E−7 |
| 22 | 1.19E−7 | 3.37E−7 | 2.00E−6 | 3.57E−7 |
| 23 | 1.20E−7 | 7.68E−7 | 5.41E−6 | 5.53E−7 |
| 24 | 1.74E−7 | 4.81E−7 | 2.38E−6 | 4.18E−7 |
| 25 | 3.21E−7 | 6.30E−7 | 2.11E−6 | 9.85E−7 |
| 26 | 1.76E−7 | 4.66E−7 | 2.10E−6 | 4.96E−7 |
| 27 | 1.69E−7 | 3.38E−7 | 7.49E−7 | 4.89E−7 |
| 28 | 1.29E−7 | 3.14E−7 | 6.36E−7 | 5.86E−7 |
| 29 | 1.99E−7 | 3.40E−7 | 7.82E−7 | 5.18E−7 |
| 30 | 2.26E−7 | 1.65E−6 | 1.05E−5 | 1.14E−6 |
| 31 | — | — | — | — |
| 32 | — | — | — | — |
| 33 | — | — | — | — |
| 34 | — | — | — | — |

Solubility Assays

Aqueous solubility at pH 6.5 was determined by an orientating high throughput screening method in PBS buffer pH 6.5 containing 1% DMSO. Test compounds were applied as 1 mm DMSO solution. After addition of PBS buffer pH 6.5 solutions were shaken for 24 h at room temperature. Undissolved material was removed by filtration. The compound dissolved in the filtrate was quantified by HPLC-UV. The response was fitted to a one-point standard curve prepared in DMSO (Onofrey, T. et al., Millipore Corporation, Life Sciences Division, Danvers, MA USA 01923: Automated Screening of Aqueous Compound Solubility in Drug Discovery (Jul. 31, 2019).

Solubility of solid compound in aqueous buffer was determined by an equilibrium shake flask method. A saturated solution of drug in solvent (~2 mg/ml solvent) was prepared and the solution was mixed for 24 h to ensure that equilibrium has been reached. The solution was centrifuged to remove the insoluble fraction and the concentration of the compound in solution was determined by HPLC-UV using a standard calibration curve (Kerns, E. H. et al., Solubility Methods in: Drug-like Properties: Concepts, Structure Design and Methods, p 276-286. Burlington, MA: Academic Press 2008).

Table 4 shows the results of two solubility assays.

TABLE 4

| Example No. | Thermodynamic Solubility [mg/l] (mean) | Thermodynamic Solubility [μmol/L] (mean) |
|---|---|---|
| 1 | 9.60 | 21.55 |
| 2 | 85.20 | 208.09 |
| 3 | 9.10 | 21.34 |
| 4 | 25.25 | 63.70 |
| 5 | >409.40 | >999.89 |
| 6 | — | — |
| 7 | — | — |
| 8 | — | — |
| 9 | 1.30 | 3.07 |
| 10 | 15.40 | 38.85 |
| 11 | 8.40 | 20.47 |
| 12 | 9.90 | 23.32 |
| 13 | 65.90 | 160.56 |
| 14 | 4.60 | 10.86 |
| 15 | 0.80 | 1.80 |
| 16 | 2.50 | 5.90 |
| 17 | 14.90 | 34.06 |
| 18 | 5.40 | 12.26 |
| 19 | 84.00 | 177.41 |
| 20 | 23.90 | 50.06 |
| 21 | <0.10 | <0.21 |
| 22 | 12.60 | 30.55 |
| 23 | 59.50 | 150.10 |
| 24 | 26.30 | 64.08 |
| 25 | 23.10 | 56.28 |
| 26 | 6.10 | 14.86 |
| 27 | <0.10 | <0.23 |
| 28 | <0.10 | <0.23 |
| 29 | <0.10 | <0.22 |
| 30 | 5.80 | 14.13 |
| 31 | — | — |
| 32 | — | — |
| 33 | — | — |
| 34 | — | — |

HERG Inhibition Assay

To investigate whether the compound inhibits the human Ether-a-go-go-Related Gene (hERG) potassium channel, in vitro automated voltage clamp recordings were performed on recombinant HEK293 cells stably expressing the hERG alpha subunit (hERG cells). Following harvest, cells were transferred to the cell reservoir of a 384 channel automated patch clamp device and stored there at 20° C. until usage.

Upon start of the automated voltage clamp procedure, hERG cells were transferred to a 384 well patch clamp chip (pipette resistance of ~2-3 M (2) prefilled with external solution (containing in mM: 143 NaCl, 4 KCl, 2 $CaCl_2$), 1 $MgCl_2$, 5 glucose, 10 HEPES; pH 7.4 (NaOH)). Underpressure was applied underneath the glass bottom of the patch clamp chip to position the hERG cells on the recording sites in the glass bottom of the chip. Following successful cell catch, underpressure was stopped and a seal enhancing solution (containing in mM: 78 NaCl, 60 NMDG, 4 KCl, 10 $CaCl_2$), 1 $MgCl_2$, 5 glucose, 10 HEPES; pH 7.4 (HCl)) was added to the hERG cells to facilitate the formation of stable seals between the membranes of the hERG cells and the glass next to the recording sites. Then, hERG cells were washed several times with wash solution (containing in mM: 87 NaCl, 60 NMDG, 4 KCl, 2 $CaCl_2$), 1 $MgCl_2$, 5 glucose, 10 HEPES; pH 7.4 (HCl)) to remove excess seal enhancing solution. In the meantime, the membrane parts of the hERG cells covering the recording sites were exposed to internal solution (containing in mM: 10 NaCl, 123 KF, 10 EGTA, 10 HEPES; pH 7.2 (KOH)) supplemented with 5-20 μM Escin, and the perforated patch configuration was established. Next, the holding potential was stepwise adjusted to −80 mV, capacitance was compensated, and a series of defined voltage commands was initiated to trigger the hERG current response from the hERG cells (−80 mV for 200 ms, +20 mV for 1000 ms, −40 mV for 500 ms; repeated at a frequency of 0.1 Hz). To determine whether the test item inhibits hERG, different solutions were sequentially applied to the hERG cells: First, a negative control (i.e. wash solution supplemented with 0.3% DMSO and 0.01% HSA) was applied for at least 3 min to investigate the basic electrophysiological properties of the hERG cells as well as define their standard current response. Next, a solution containing the test item at a final concentration of (0.1, 1, or 10) μM was applied for 10 min to measure eventual inhibitory effects of the test item on the hERG current (—the test item solution was produced from a 10 mM DMSO stock by using an automated pipetting device and sequential dilution). Finally, a positive control (i.e. wash solution supplemented with 0.3% DMSO, 0.01% HSA, and 10 μM quinidine) was added to the cells for ~3 min to block the hERG current and, thereby, define the maximum inhibition. For data analysis, experimental results were processed using the automated patch clamp device-specific software as well as a custom-made software, and TIBCO Spotfire. For each successful recording, hERG tail current amplitudes were averaged from three consecutive current responses at the end of the negative control phase, test item phase, and positive control phase, respectively. Resulting mean hERG tail current amplitudes were normalized to the mean hERG tail current amplitude at the end of the negative control phase with nominal 0% inhibition as well as the hERG tail current amplitude at the end of the positive control phase with nominal 100% inhibition. Then, the effect of the test item was calculated as a percentage inhibition value at the test item concentration applied. Finally, percentage inhibition values from all successful recordings at a particular test item concentration were averaged and combined to construct a standard sigmoidal dose response curve, determine the half maximal inhibitory concentration ($IC_{50}$) of the test item as well as extrapolate its $IC_{20}$.

Table 5 shows the results of a hERG inhibition assay.

TABLE 5

| Example No. | hERG Inhibition, Automated Voltage Clamp ($IC_{50}$ μM) |
|---|---|
| 3 | 5.98 |
| 4 | >10 |
| 6 | 5.35 |
| 15 | 1.45 |
| 18 | 2.05 |
| 21 | 0.81 |
| 28 | 8.69 |

Comparator Compounds

Comparator compounds C1, C2, C3, and C4 were tested in one or more of the aforementioned assays. This data is shown in Tables 6-9.

(C1)

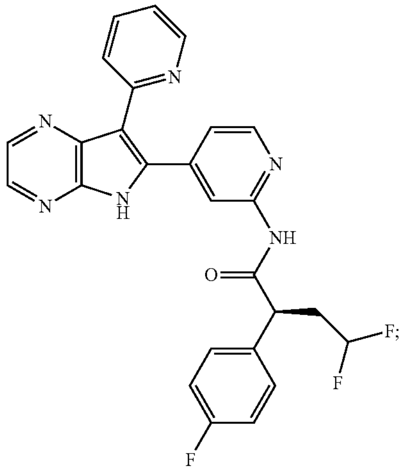

(C2)

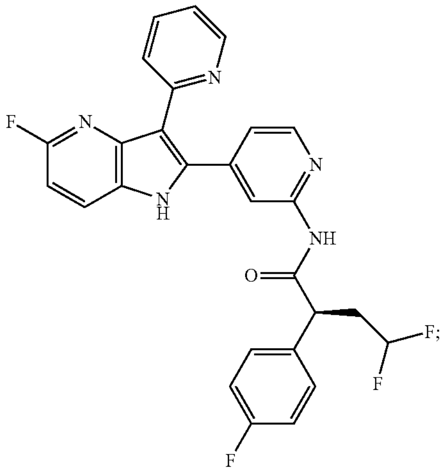

(C3)

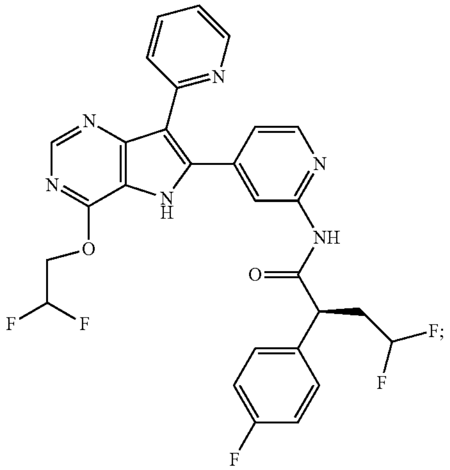

and

-continued (C4)

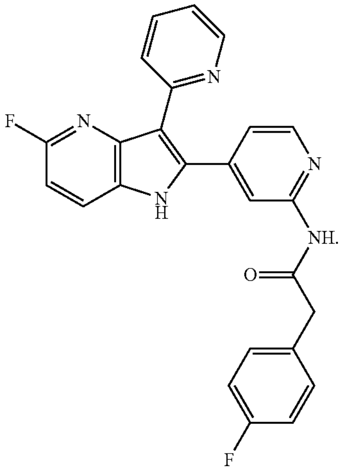

TABLE 6

| Comparator | CSNK1A1 Low ATP $IC_{50}$ [mol/l] (median) | CSNK1D $IC_{50}$ [mol/l] (median) | CSNK1G $IC_{50}$ [mol/l] (median) | CSNK1A1 High ATP assay $IC_{50}$ [mol/l] (median) |
|---|---|---|---|---|
| C1 | 1.25E−9 | 3.92E−9 | 6.54E−9 | 2.01E−8 |
| C2 | 1.21E−9 | 2.26E−9 | 2.40E−9 | 5.27E−9 |
| C3 | 3.10E−9 | 3.27E−9 | 6.22E−9 | 8.84E−9 |

TABLE 7

| Comparator | HTRF total-p53 MCF-7, $IC_{50}$ - [mol/l] (median) | 2D-PROLI HT-29 CTG 96 h, $IC_{50}$ - [mol/l] (median) | 2D-PROLI LoVo CTG 96 h, $IC_{50}$ - [mol/l] (median) | 2D-PROLI HCT 116 CTG 96 h, $IC_{50}$ - [mol/l] (median) |
|---|---|---|---|---|
| C1 | 7.28E−8 | 2.06E−7 | 2.11E−7 | 4.29E−7 |
| C2 | 7.24E−8 | 8.88E−8 | 1.15E−7 | 1.84E−7 |
| C3 | 9.79E−8 | 1.10E−7 | 1.15E−7 | 7.35E−7 |

TABLE 8

| Comparator | Thermodynamic Solubility [mg/l] (mean) | Thermodynamic Solubility [μmol/L] (mean) |
|---|---|---|
| C1 | 9.60 | 21.55 |
| C2 | 0.20 | 0.40 |
| C3 | <0.10 | <0.18 |
| C4 | 2.35 | — |

TABLE 9

| Comparator | hERG Inhibition, Automated Voltage Clamp ($IC_{50}$ μM) |
|---|---|
| C4 | 1.16 |

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

The invention claimed is:

1. A compound represented by formula (I) or a pharmaceutically acceptable salt thereof:

(I)

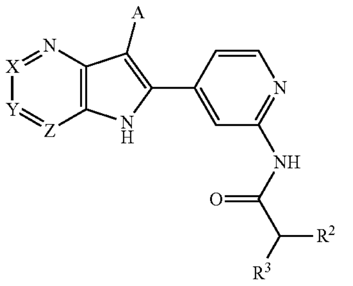

wherein,

A is optionally substituted heteroaryl;

X, Y and Z are each independently N or $CR^1$, wherein at most one of X, Y and Z is N;

each $R^1$ is independently H, alkyl, alkoxy, haloalkoxy, halo, nitrile, amino or aminoalkyl;

$R^2$ is haloalkyl, aryl or hydrogen; and $R^3$ is optionally substituted heteroaryl.

2. The compound of claim 1, wherein X, Y and Z are each $CR^1$.

3. The compound of claim 2, wherein each $R^1$ is H.

4. The compound of claim 1, wherein A is a 5- or 6-membered heteroaryl.

5. The compound of claim 4, wherein A is pyridyl.

6. The compound of claim 5, wherein A is

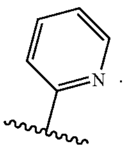 [SMILES: *c1ccccn1]

7. The compound of claim 6, wherein the compound is represented by formula (II):

(II)

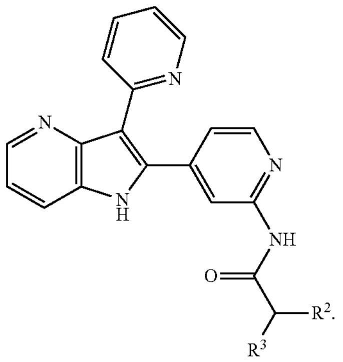

8. The compound of claim 1, wherein $R^2$ is hydrogen, haloalkyl, or fluorophenyl.

9. The compound of claim 8, wherein $R^2$ is hydrogen.

10. The compound of claim 1, wherein $R^3$ is a 5-membered heteroaryl, a 6-membered heteroaryl, a fused [5.6] heteroaryl, or a fused [6.6] heteroaryl.

11. The compound of claim 1, wherein $R^3$ comprises at least one N.

12. The compound of claim 1, wherein $R^3$ comprises at least two heteroatoms.

13. The compound of claim 1, wherein $R^3$ is a substituted heteroaryl.

14. The compound of claim 13, wherein $R^3$ is substituted with one or more groups independently selected from alkyl, cycloalkyl, haloalkyl, hydroxy, alkoxy, haloalkoxy, halo, amino, and aminoalkyl.

15. The compound of claim 14, wherein $R^3$ is substituted with one or more groups independently selected from methyl, isopropyl, cyclopropyl, trifluoromethyl and 2,2-difluoroethyl.

16. The compound of claim 1, wherein the compound is selected from:

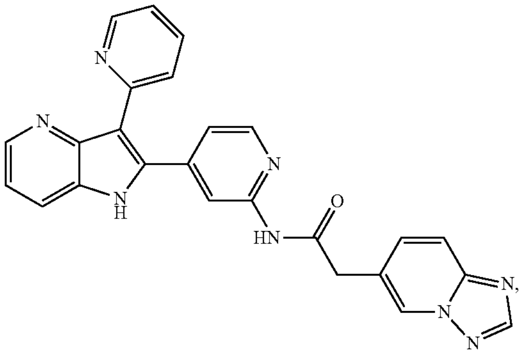

-continued
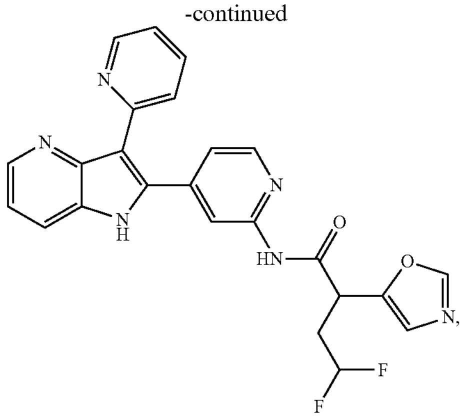
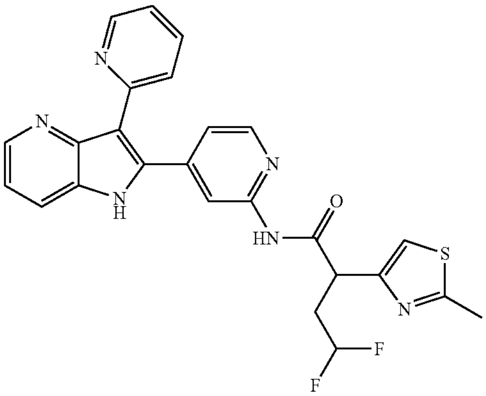
,
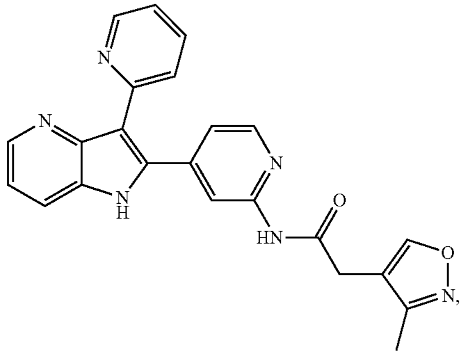
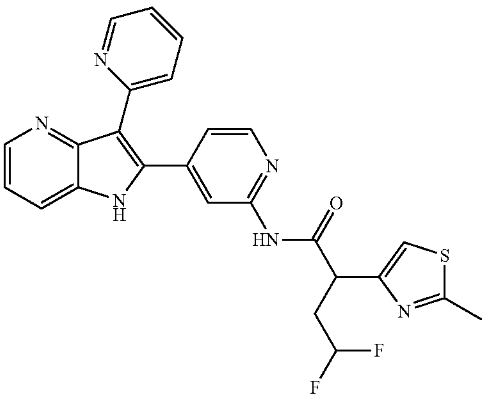
,
-continued
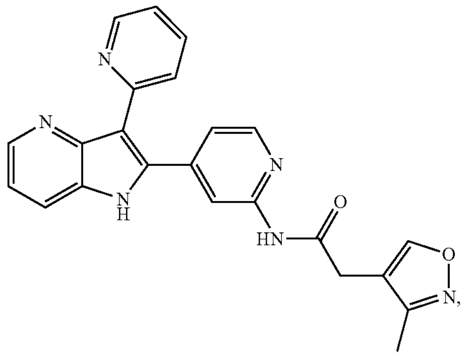
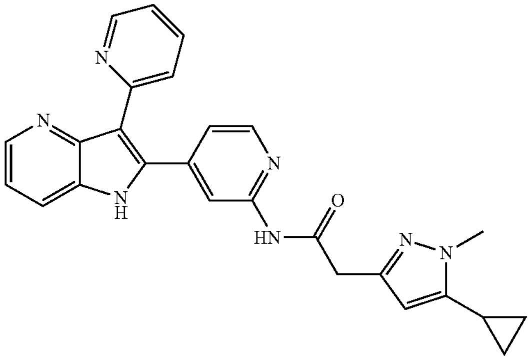
,
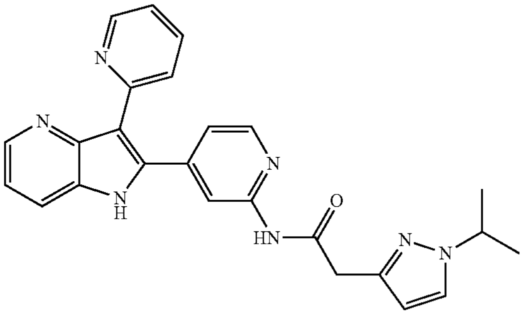
,
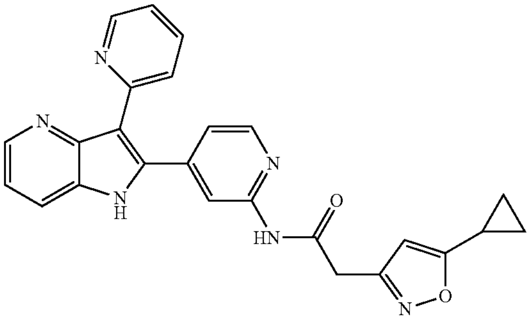
,
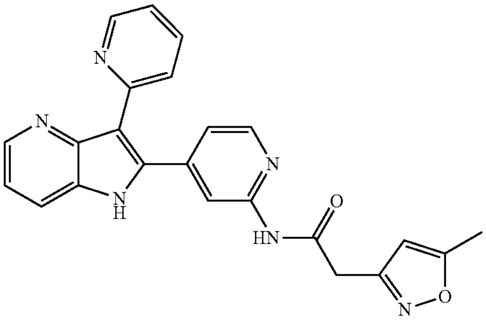
, -continued
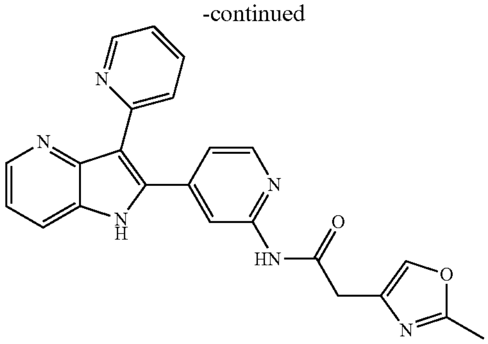
,
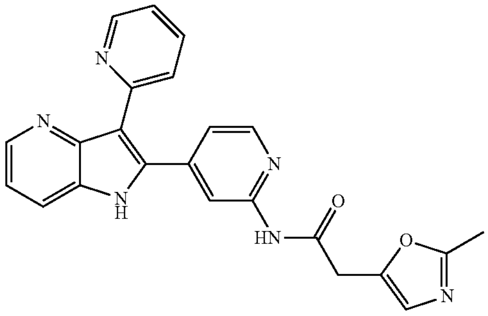
,
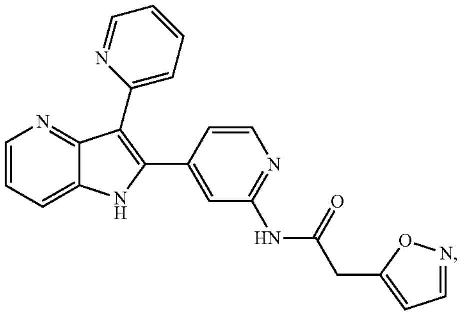
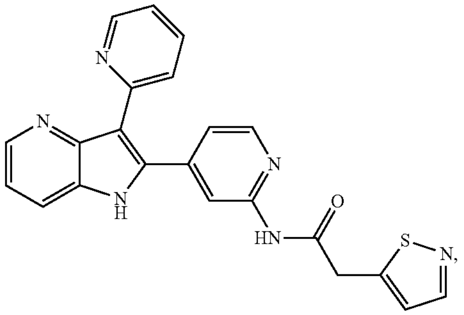
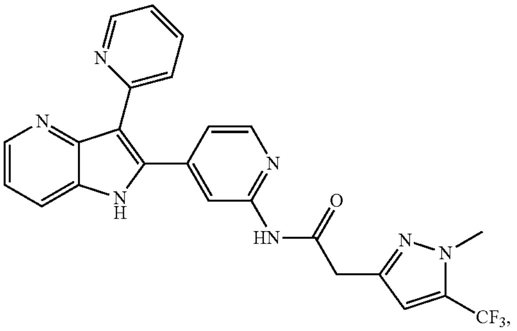
-continued
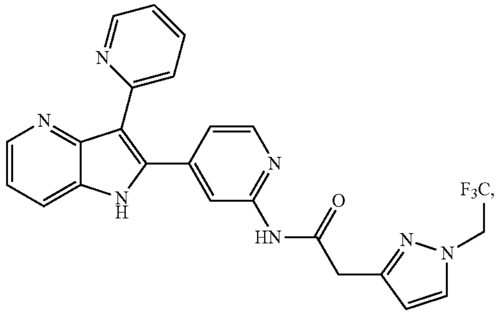
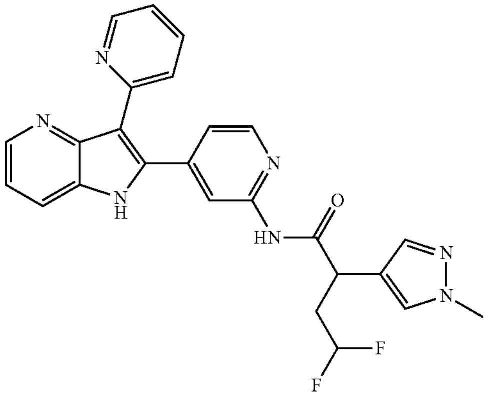
,
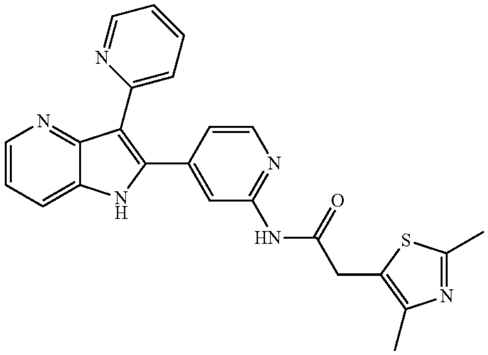
,
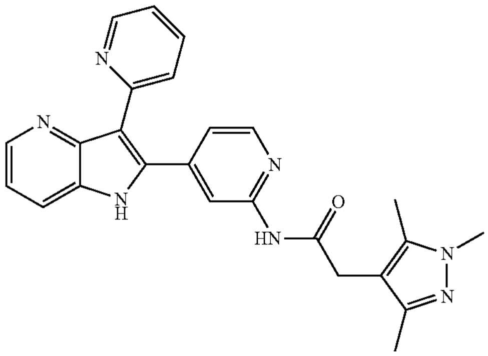
, -continued
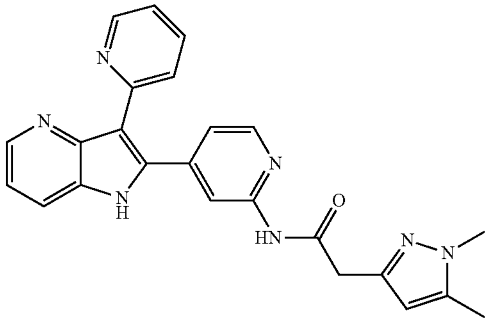
,
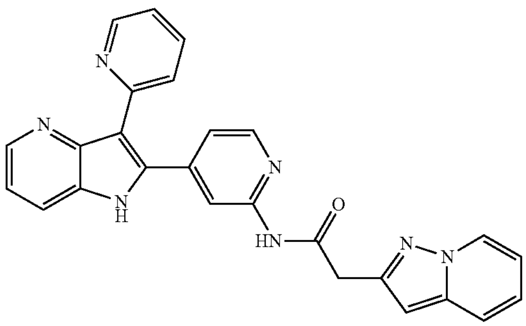
,
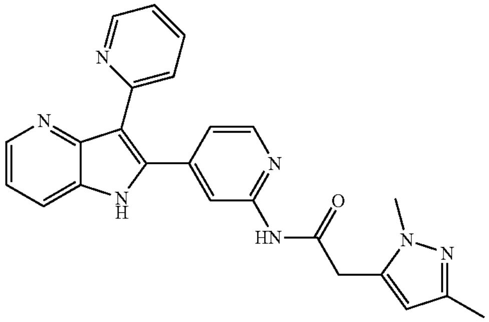
,
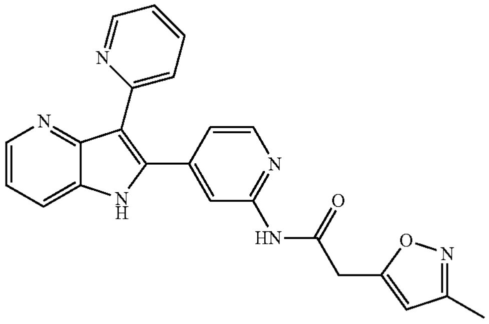
,
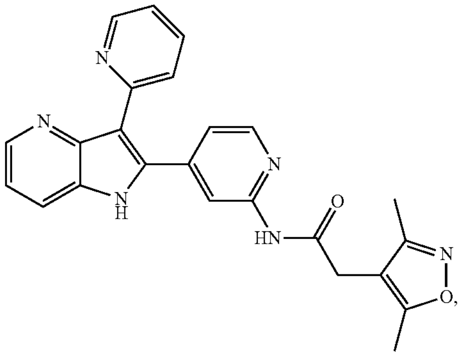
-continued
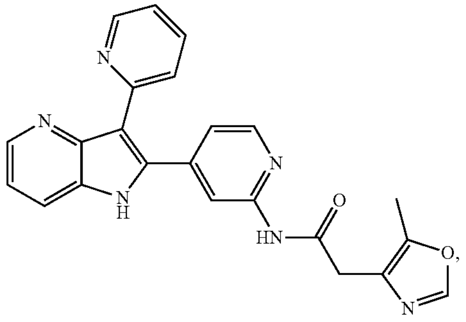
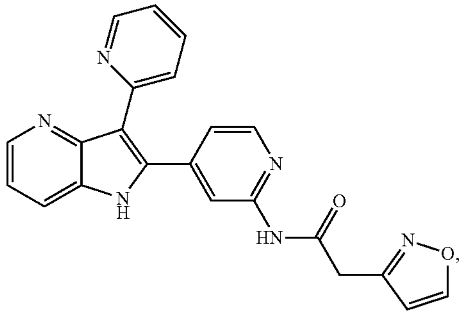
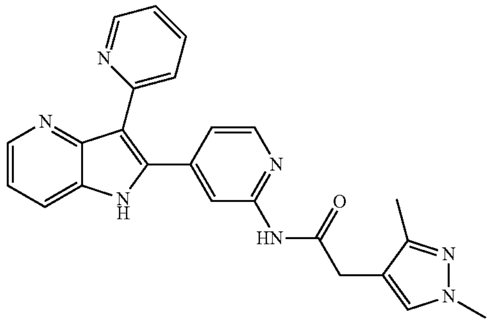
,
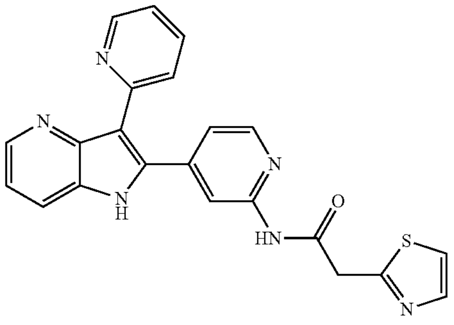
,
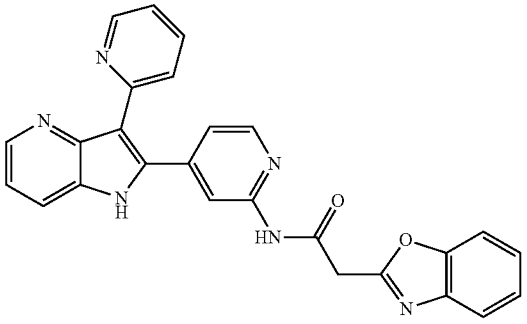
, -continued
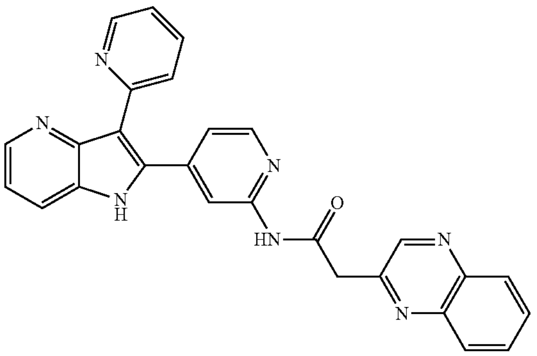
,
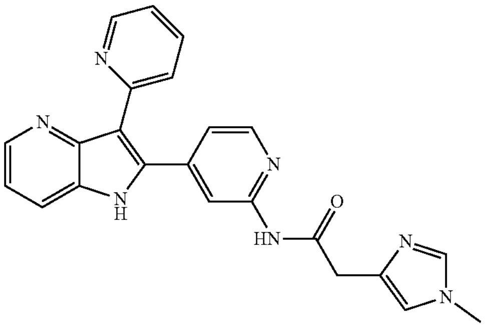
,
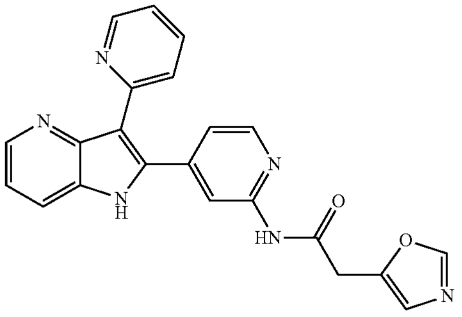
,
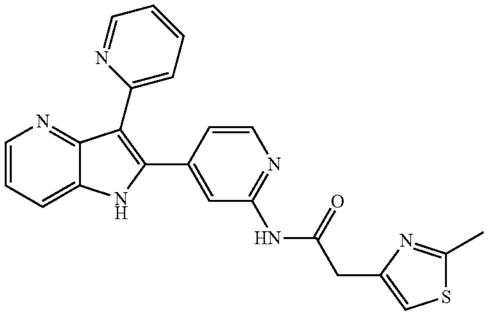
,
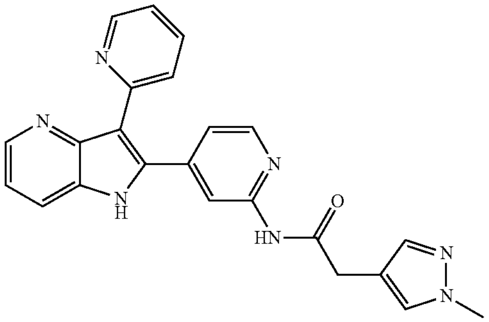
,
-continued
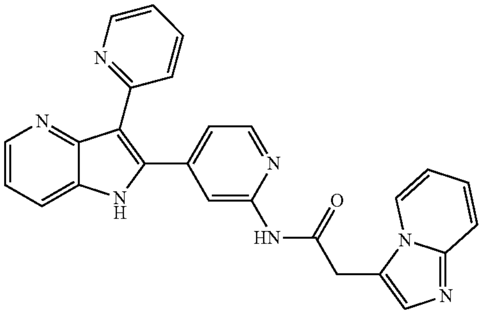
,
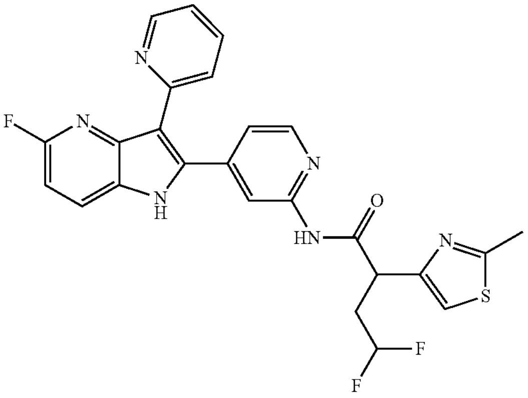
,
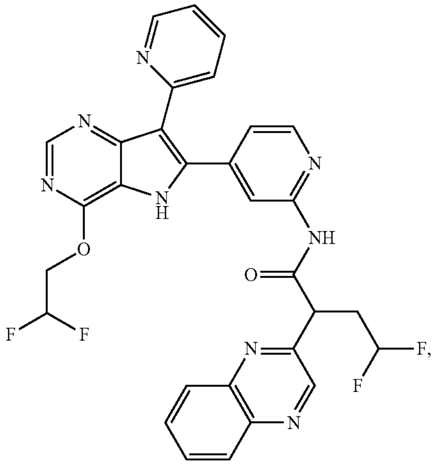
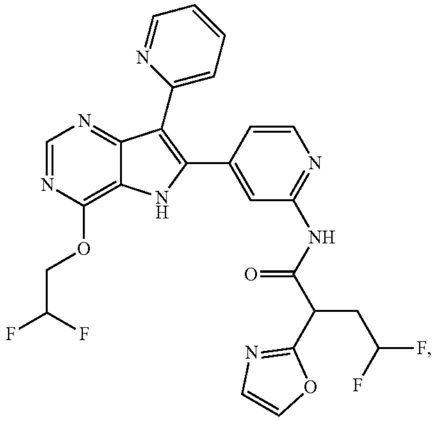

-continued
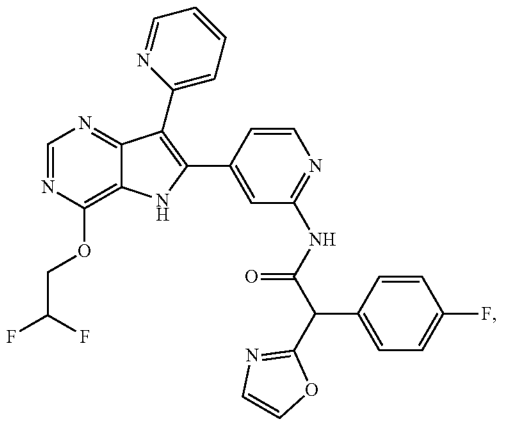
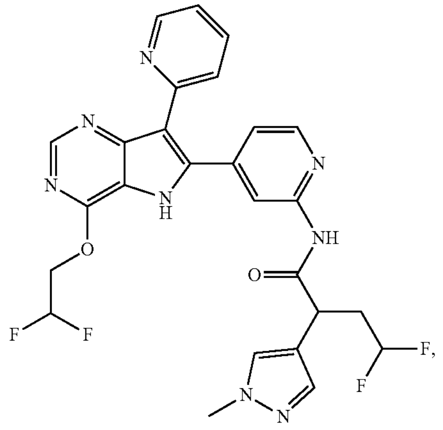
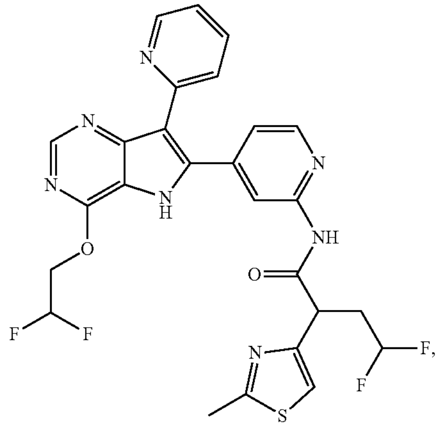
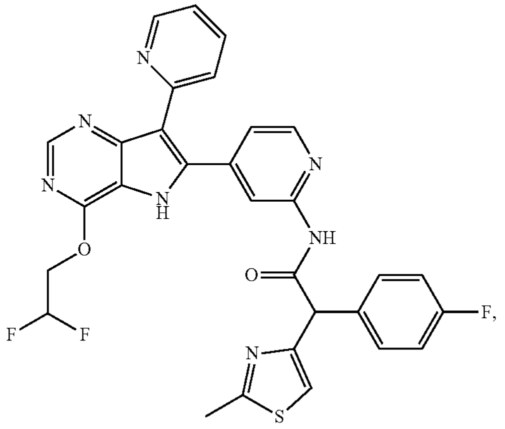
-continued
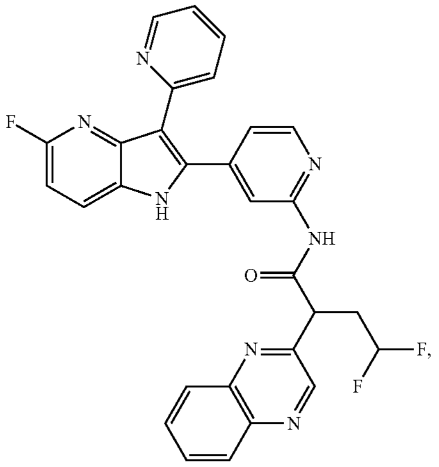
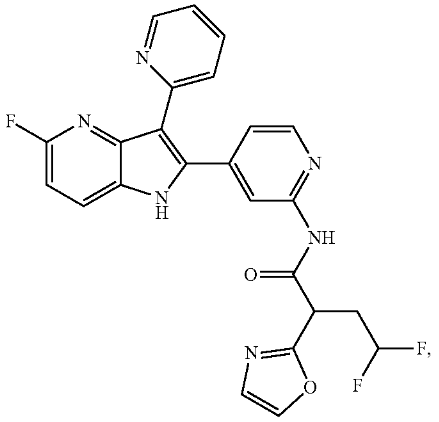
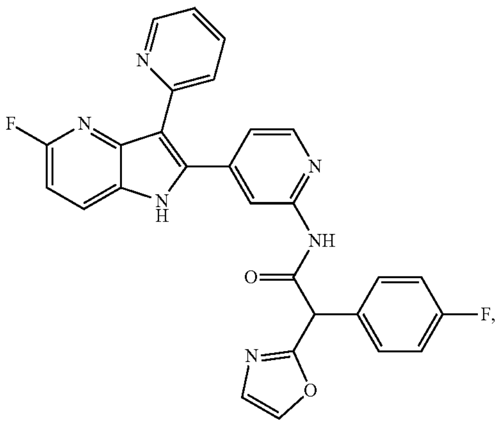

-continued

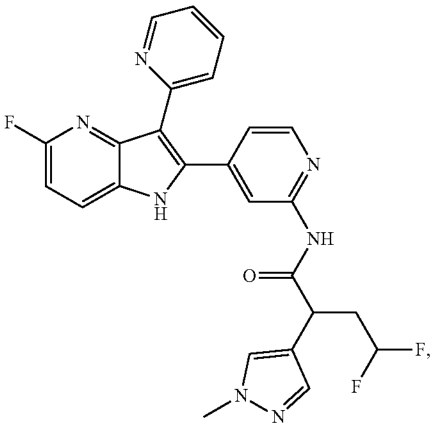

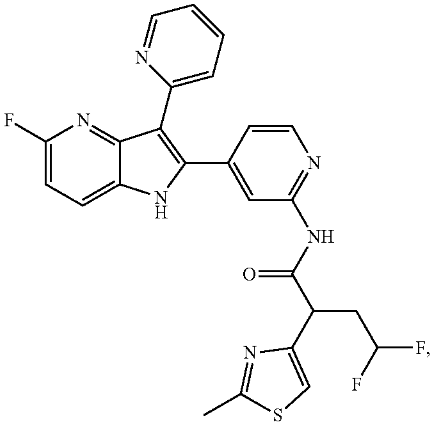

and

-continued

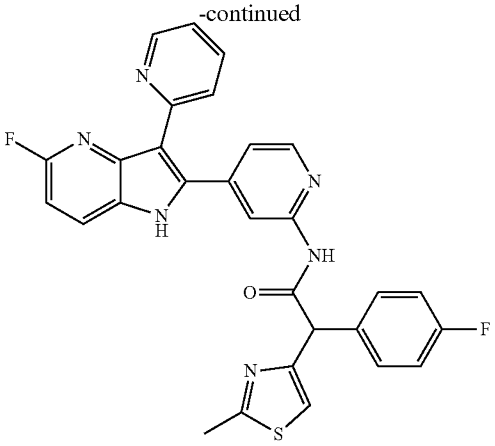

or a pharmaceutically acceptable salt thereof.

17. A pharmaceutical composition comprising a compound of claim 1 and a pharmaceutically acceptable excipient.

18. A method of treating a hyperproliferative disease or disorder responsive to induction of cell death comprising administering a compound of claim 1.

19. The method of claim 18, wherein the hyperproliferative disease or disorder is a haematological tumor, solid tumor, or metastases thereof.

20. The method of claim 19, wherein the solid tumor is a cervical tumor, a lung tumor, a colon tumor, a head and neck squamous cell carcinoma, a gastric tumor, an esophageal tumor, a bladder tumor, a urinary tract tumor, or metastases thereof.

21. The method of claim 19, wherein the haematological tumor is a lymphoma or metastases thereof.

22. The method of claim 21, wherein the lymphoma is diffuse large B-cell lymphoma or metastases thereof.

* * * * *